(12) United States Patent
Chan et al.

(10) Patent No.: US 11,129,877 B2
(45) Date of Patent: Sep. 28, 2021

(54) COMPOSITIONS IN THE FORM OF AN INJECTABLE AQUEOUS SOLUTION COMPRISING AMYLIN, AN AMYLIN AGONIST RECEPTOR OR AN AMYLIN ANALOGUE AND A CO-POLYAMINO ACID

(71) Applicant: ADOCIA, Lyons (FR)

(72) Inventors: You-Ping Chan, Ternay (FR);
Alexandre Geissler, Lyons (FR);
Romain Noel, Villeurbanne (FR);
Richard Charvet, Rillieux la Pape (FR); Nicolas Laurent, Miribel (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/213,865

(22) Filed: Dec. 7, 2018

(65) Prior Publication Data
US 2019/0328842 A1    Oct. 31, 2019

Related U.S. Application Data

(60) Provisional application No. 62/606,139, filed on Dec. 7, 2017.

(30) Foreign Application Priority Data

Dec. 7, 2017  (FR) .................................... 17/61808
Jun. 29, 2018 (FR) .................................... 18/55943

(51) Int. Cl.
| | | |
|---|---|---|
| A61K 38/00 | (2006.01) |
| A61K 38/22 | (2006.01) |
| A61K 9/00 | (2006.01) |
| A61K 47/34 | (2017.01) |

(52) U.S. Cl.
CPC ............ A61K 38/22 (2013.01); A61K 9/0019 (2013.01); A61K 47/34 (2013.01)

(58) Field of Classification Search
CPC .............................. A61K 38/22; A61K 9/0019
See application file for complete search history.

(56) References Cited

U.S. PATENT DOCUMENTS

| | | | |
|---|---|---|---|
| 5,124,314 A | 6/1992 | Cooper | |
| 5,234,906 A | 8/1993 | Young et al. | |
| 5,686,411 A | 11/1997 | Gaeta et al. | |
| 6,114,304 A | 9/2000 | Kolterman et al. | |
| 6,410,511 B2 | 6/2002 | L'Italien et al. | |
| 8,084,493 B1 * | 12/2011 | Sung ...................... | A61K 31/13 514/469 |
| 2001/0043934 A1 | 11/2001 | L'Italien et al. | |
| 2011/0082080 A1 | 4/2011 | Levetan | |
| 2015/0320876 A1 | 11/2015 | Chen et al. | |
| 2016/0001002 A1 | 1/2016 | Yodfat et al. | |

FOREIGN PATENT DOCUMENTS

| | | |
|---|---|---|
| EP | 0 347 724 A1 | 12/1989 |
| EP | 0 499 521 A1 | 8/1992 |
| FR | 2801226 A1 | 5/2001 |
| FR | 2 840 614 A1 | 12/2003 |
| FR | 2 855 521 A1 | 12/2004 |
| FR | 2 910 318 A1 | 6/2008 |
| FR | 2 985 428 A1 | 7/2013 |
| FR | 2 985 429 A1 | 7/2013 |
| WO | 03/101395 A2 | 12/2003 |
| WO | 2007/104786 A1 | 9/2007 |
| WO | 2009/077844 A2 | 6/2009 |
| WO | 2009/089506 A1 | 7/2009 |
| WO | 2013/067022 A1 | 5/2013 |
| WO | 2013/104861 A1 | 7/2013 |
| WO | 2015/114171 A1 | 8/2015 |
| WO | 2017/211916 A1 | 12/2017 |
| WO | 2017/211918 A1 | 12/2017 |
| WO | 2018/122278 A1 | 7/2018 |

OTHER PUBLICATIONS

Goldsbury CS, et al.; "Polymorphic Fibrillar Assembly of Human Amylin". J. Struct. Biol., vol. 119, pp. 17-27, 1997.
Annex 1; Summary of Product Characteristics of ADIPRA®.
Bhatnagar, Pradip et al. "Structure-Activity Relationships of Novel Hematoregulatory Peptides" . J. Med. Chem., vol. 39, pp. 3814-3819, 1996.
Hoppmann, Christian et al.; "Intramolecular bridges formed by photoswitchable click amino acids;" Beilstein J. Org. Chem., vol. 8, pp. 884-889, 2012.
Burnett, Christina et al.; "Safety Assessment of Amino Acid Alkyl Amides as Used in Cosmetics;" International Journal of Toxicology, vol. 36, No. 1, pp. 17S-56S, 2017.
Wu, Chuanliu et al. "Interplay of Chemical Microenvironment and Redox Environment on Thiol-Disulfide Exchange Kinetics;" Chem. Eur. J., vol. 17, pp. 10064-10070, 2011.

(Continued)

Primary Examiner — Jeanette M Lieb
(74) Attorney, Agent, or Firm — Oliff PLC

(57) ABSTRACT

A composition in the form of an injectable aqueous solution, for which the pH is comprised from 6.0 to 8.0, includes at least:
a) amylin, an amylin receptor agonist or an amylin analogue;
b) a co-polyamino acid bearing carboxylate charges and hydrophobic radicals Hy, said co-polyamino acid being constituted of glutamic or aspartic units and said hydrophobic radicals Hy chosen according to formula X as defined below:
c)

Formula X

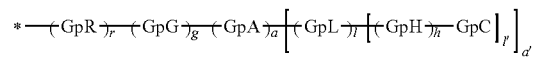

characterized in that the composition does not include basal insulin for which the isoelectric point IP is comprised from 5.8 to 8.5. The composition also includes a prandial insulin.

13 Claims, 1 Drawing Sheet

(56) References Cited

OTHER PUBLICATIONS

Liang, Jiang et al. "Distinct optical and kinetic responses from E/Z isomers of caspase probes with aggregation-induced emission characteristics;" J. Mater. Chem. B., vol. 2, pp. 4363-4370, 2014.
Liu, Jixiang et al.; "Fluorescent Molecular Probes V: A Sensitive Caspase-3 Substrate for Fluorometric Assays;" Bioorganic & Medicinal Chemistry Letters; vol. 9, pp. 3231-3236, 1999.
Leishman, Emma et al.; "Lipidomics profile of a NAPE-PLD KO mouse provides evidence of a broader role of this enzyme in lipid metabolism in the brain" . Biochimica et Biophysica Acta; vol. 1861, pp. 491-500, 2016.
Schlitzer, Martin et al.; "Non-peptidic, Non-prenylic Bisubstrate Farnesyltransferase Inhibitors, 4. Effect on Farnesyltransferase Inhibitory Activity of Conformational Restrictions in the Central Group;" Pharm. Pharmacol. Commun. vol. 5, pp. 117-124, 2000.
Gerich, John. "Control of Glycaemia". Bailliere's Clinical Endocrinology and Metabolism; vol. 7, No. 3, pp. 551-586, 1993.
Schmitz, Ole et al. "Amylin Agonists: A Novel Approach in the Treatment of Diabetes;" Diabetes, vol. 53, No. 3, pp. S233-S238, 2004.
Yan, Li-Mei et al. "Design of a mimic of nonamyloidogenic and bioactive human islet amyloid polypeptide (IAPP) as nanomolar affinity inhibitor of IAPP cytotoxic fibrillogenesis". PNAS, vol. 103, No. 7, pp. 2046-2051, 2006.
Niaiki, Hironobu et al. "Fluorometric Determination of Amyloid Fibrils in Vitro Using the Fluorescent Dye, Thioflavine T1" Analytical Biochemistry; vol. 177, pp. 244-249; 1989.
Levine III, Harry. "Quantifications of β-Sheet Amyloid Fibril Structures with Thioflavin T". Methods in Enzymology; vol. 309, pp. 274-284; 1999.
Feb. 12, 2019 Search Report issued in International Patent Application No. PCT/EP2018/083964.
Feb. 15, 2019 Search Report issued in International Patent Application No. PCT/EP2018/083943.
Deming, Timothy "Polypeptide and Polypeptide Hybrid Copolymer Synthesis via NCA Polymerization;" Adv. Polym. Sci, vol. 202, pp. 1-18, 2006.
Deming, Timothy. "Facile synthesis of block copolypeptides of defined architecture". Nature, vol. 390, pp. 386-389, 1997.
Lu, Hua et al. "Hexamethyldisilazane-Mediated Controlled Polymerization of α-Amino Acid N-Carboxyanhydrides". J. Am. Chem. Soc.vol. 129, pp. 14114-14115, 2007.
Lu, Hua et al. "N-Trimethylsilyl Amines for Controlled Ring-Opening Polymerization of Amino Acid N-Carboxyanhydrides and Facile End Group Functionalization of Polypeptides" . J. Am. Chem. Soc, vol. 130., pp. 12562-12563 and S1-S8, 2008.
Mar. 8, 2019 Search Report issued in International Application No. PCT/EP2018/084063.
U.S. Appl. No. 16/213,776, filed Dec. 7, 2018 in the name of Chan et al.
U.S. Appl. No. 16/213,881, filed Dec. 7, 2018 in the name of Geissler.
Gonzalez, Jose Vicente et al. "Polypeptides and polyaminoacids in drug delivery." Expert Opinion, vol. 9 No. 2, pp. 183-201, 2012.
Nov. 27, 2020 Office Action issued in U.S. Appl. No. 16/213,776.

* cited by examiner

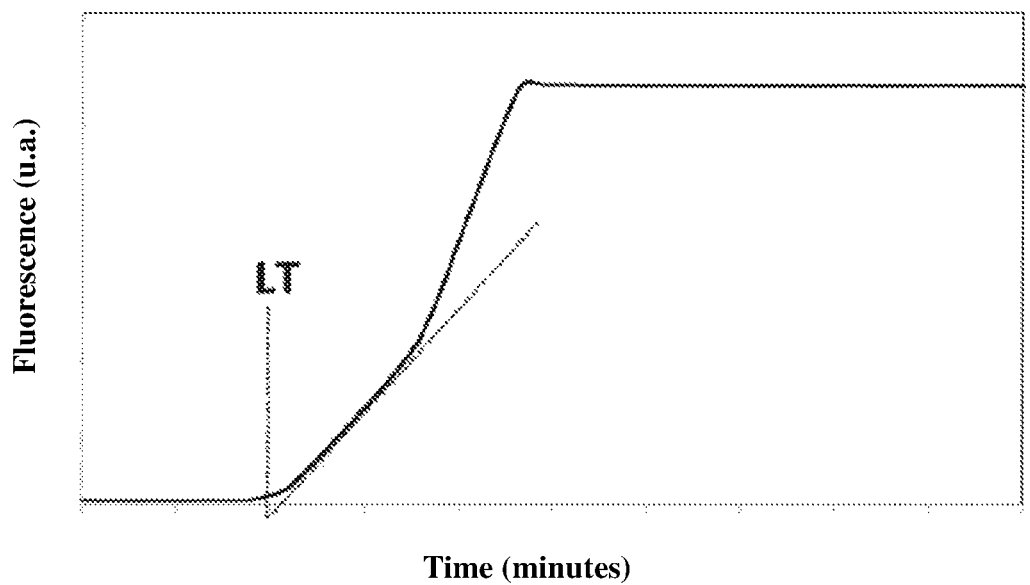

COMPOSITIONS IN THE FORM OF AN INJECTABLE AQUEOUS SOLUTION COMPRISING AMYLIN, AN AMYLIN AGONIST RECEPTOR OR AN AMYLIN ANALOGUE AND A CO-POLYAMINO ACID

The invention relates to amylin injection therapies, amylin agonist receptor or to an amylin analogue for the treatment of diabetes.

The invention relates to a composition in the form of an injectable aqueous solution, for which the pH is comprised from 6.0 to 8.0, comprising at least amylin, an amylin agonist receptor or an amylin analogue and a co-polyamino acid bearing carboxylate charges and hydrophobic radicals according to the invention and compositions comprising, in addition, an insulin (excluding basal insulins for which the isoelectric point pI is comprised from 5.8 to 8.5). The invention also relates to pharmaceutical formulations comprising the compositions according to the invention. Finally, the invention also relates to a use of co-polyamino acids bearing carboxylate charges and hydrophobic radicals according to the invention, in order to stabilize compositions of amylin, of amylin agonist receptors or of amylin analogue as well as amylin, amylin receptor agonist or amylin analog compositions further comprising an insulin.

Diabetes type 1 is an autoimmune disease leading to the destruction of the pancreas beta cells. These cells are known to produce insulin, the principal role of which is to regulate the use of glucose in peripheral tissues (Gerich 1993, Control of glycaemia). As a result, patients affected by type 1 diabetes suffer chronic hyperglycemia and must self-administer exogenous insulin in order to control this hyperglycemia. Insulin therapy makes it possible to drastically change the life expectancy of these patients. However, the control of glycemia provided by exogenous insulin is not optimal, in particular after ingesting a meal. This is linked to the fact that these patients produce glucagon after ingesting a meal, which leads to the release of a portion of the glucose stored in the liver, which is not the case in a healthy person. This glucagon-mediated glucose production worsens the glycemia regulation problem for these patients.

It has been demonstrated that amylin, another hormone produced by the beta cells of the pancreas, and therefore also deficient in type 1 diabetes patients, plays a key role in the regulation of post-prandial glycemia. Amylin, also known as "islet amyloid polypeptide", or IAPP, is a peptide of 37 amino acids which is stored and co-secreted with insulin (Schmitz 2004 Amylin Agonists). This peptide is described as blocking the production of glucagon by the alpha cells of the pancreas. Thus, insulin and amylin have complementary and synergistic roles, since insulin makes it possible to reduce the concentration of glucose in the blood, while amylin makes it possible to reduce the entry of endogenous glucose into the blood by inhibiting the production (secretion) of endogenous glucagon.

This problem of post-prandial glycemia regulation is quite similar for patients with type 2 diabetes taken up with insulin insofar as their disease has led to a very significant loss of their mass of beta cells and, as a result, of their ability to produce insulin and amylin.

Human amylin has properties which are not compatible with pharmaceutical requirements in terms of solubility and stability (Goldsbury C S, Cooper G J, Goldie K N, Muller S A, Saafi E L, Gruijters W T, Misur M P, Engel A, Aebi U, Kistler J: Polymorphic fibrillar assembly of human amylin. J Struct Biol 119:17-27, 1997). Amylin is known to form amyloid fibrils which lead to the formation of plaques which are not soluble in water. Even though it is a natural hormone, it was necessary to develop an analogue in order to solve these solubility problems.

The physicochemical properties of amylin thus make its use impossible: amylin is only stable for about fifteen minutes at acidic pH, and less than a minute at neutral pH.

The company Amylin developed an amylin analogue, pramlintide, to moderate the lack of stability of human amylin. This product, marketed under the name Symlin, was approved in 2005 by the FDA for the treatment of type 1 and type 2 diabetics. It must be administered subcutaneously three times a day, within an hour prior to the meal, in order to improve control of post-prandial glycemia. This peptide is formulated at acidic pH and is described as fibrillating when the pH of the solution is greater than 5.5. Analogue variants are described in U.S. Pat. No. 5,686,411.

This analogue is thus not satisfactory in terms of stability when a formulation at neutral pH is envisaged.

To date, there is no means making it possible to stabilize human amylin in order to make a pharmaceutical product. However, it would be beneficial for patients to have access to the human form of this physiological hormone. It would also be beneficial to be able to formulate an analogue or agonist of pH neutral amylin receptor.

In addition, there would be an interest in being able to mix an aqueous amylin solution, an amylin analogue, or an amylin agonist receptor, with a prandial insulin, since these two products are to be administered before the meal. This would further make it possible to mimic the physiology since these two hormones are co-secreted by the beta cells in response to a meal in order to improve the control of post-prandial glycemia.

However, given the fact that solutions of prandial insulins have a pH that is close to neutral for reasons of chemical stability, it is not possible to obtain an aqueous solution that meets the pharmaceutical requirements in terms of solubility and stability.

For this reason, patent application US2016/001002 from ROCHE describes a pump containing two separate reservoirs in order to make possible the co-administration of these two hormones with a single medical device. However, this patent does not solve the problem of mixing these two hormones in solution which would make it possible to administer them with conventional pumps already on the market which contain only one reservoir.

Patent application WO2013067022 from XERIS provides a solution to the problem of amylin stability and to its compatibility with insulin by employing an organic solvent instead of water. The absence of water seems to solve the stability problems, but the use of an organic solvent poses problems in terms of long-term safety of use for diabetic patients and also compatibility problems with standard medical devices, related to tubing, connections and the plasticizers used.

Patent application WO2007104786 from NOVO NORDISK describes a method making it possible to stabilize a solution of pramlintide, which is an amylin analogue, and of insulin by the addition of a phospholipid, derived from glycerophosphoglycerol, in particular from dimyristoyl glycerophosphoglycerol (DMPG). However, this solution requires the use of significant quantities of DMPG which can pose a problem with local tolerance. Furthermore, DMPG leads to compositions presenting relatively poor physical stabilities at 0-4° C., as described in the application WO2018122278.

To the applicant's knowledge, there is no satisfactory means which makes it possible to combine a prandial insulin and human amylin, an amylin agonist receptor or an amylin analogue in an aqueous solution, so as to be able to be administered with conventional devices.

The acidic formulation pH and the rapid fibrillation are obstacles to obtain a pharmaceutical formulation at neutral pH based on amylin and pramlintide, but also an obstacle to combine amylin or pramlintide with other pharmaceutical active ingredients, in particular, peptides or proteins.

The applicant observed that, surprisingly, the co-polyamino acids according to the invention stabilize compositions of amylin, of amylin agonist receptor or amylin analogue at a pH from 6.0 to 8.0. In fact, compositions comprising amylin, amylin agonist receptor or amylin analogue in combination with a co-polyamino acid according to the invention exhibit an increased stability over time, which is of great interest for pharmaceutical development.

The applicant has also reported that co-polyamino acids according to the invention make it possible, in addition, to obtain a composition comprising prandial insulin and amylin, amylin agonist receptor or amylin analogue, with said composition being clear and having an enhanced stability toward fibrillation.

A classical method for measuring the stabilities of proteins or peptides consists of measuring the formation of fibrils using Thioflavin T, also called ThT. This method makes it possible to measure the latency time before the formation of fibrils by measuring the increase in fluorescence, and to do so under temperature and stirring conditions that make an acceleration of the phenomenon possible. Compositions according to the invention have a latency period before the formation of fibrils that is clearly greater than that of amylin, of an amylin agonist receptor or of an amylin analogue at the pH of interest.

Compositions according to the invention have a physical stability, and possibly a chemical stability, at the desired pH.

In one embodiment, the invention relates to a composition in the form of an injectable aqueous solution, for which the pH is comprised from 6.0 to 8.0, comprising at least:
a) Amylin, an amylin receptor agonist and an amylin analogue;
b) A co-polyamino acid bearing carboxylate charges and hydrophobic radicals Hy, said co-polyamino acid being constituted of glutamic or aspartic units and said hydrophobic radicals -Hy chosen among the radicals according to formula X as defined below:

Formula X

In which
GpR is chosen among the radicals according to formulas VII, VII' or VII":

Formula VII

Formula VII'

Formula VII";

Identical or different GpG and GpH are chosen among the radicals according to formulas XI or XI';

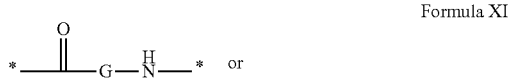

Formula XI

Formula XI'

GpA is chosen among the radicals according to formula VIII

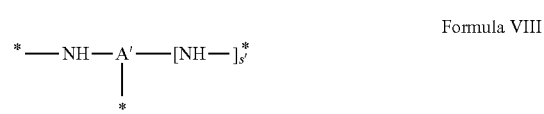

Formula VIII

In which A' is chosen among the radicals according to formulas VIII', VIII" or VIII'"

Formula VIII'

Formula VIII"

Formula VIII'"

GpL is chosen among the radicals according to formula XII

Formula XII

GpC is a radical according to formula IX:

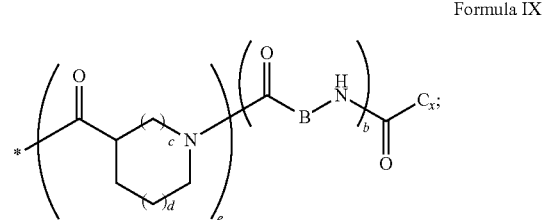

Formula IX

* indicate the attachment sites of the different groups bound by amide functions;

a is an integer equal to 0 or to 1 and a'=1 if a=0 and a'=1, 2 or 3 if a=1;

a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g, h or l is different from 0;
l is an integer equal to 0 or to 1 and l'=1 if l=0 and l'=2 if l=1;
r is an integer equal to 0, 1 or to 2, and
s' is an integer equal to 0 or to 1;
And if e is different from 0, then at least one of g, h or l is different from 0;
And if a=0, then l=0;
A, $A_1$, $A_2$ and $A_3$ identical or different, are linear or branched alkyl radicals comprising from 1 to 8 carbon atoms and, optionally, substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms.
$C_x$ is a monovalent, linear or branched, alkyl radical optionally comprising a cyclic part, in which x indicates the number of carbon atoms, and:
When the hydrophobic radical -Hy bears 1 -GpC, then $9 \leq x \leq 25$,
When the hydrophobic radical -Hy bears 2 -GpC, then $9 \leq x \leq 15$,
When the hydrophobic radical -Hy bears 3 -GpC, then $7 \leq x \leq 13$,
When the hydrophobic radical -Hy bears 4 -GpC, then $7 \leq x \leq 11$,
When the hydrophobic radical -Hy bears at least 5 -GpC, then $6 \leq x \leq 11$,
G is a linear or branched divalent alkyl radical of 1 to 8 carbon atoms, said alkyl radical bearing one or more free carboxylic acid functions.
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms.
The hydrophobic radicals -Hy according to formula X being bound to the PLG:
via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG.
The ratio M between the number of hydrophobic radicals and the number of glutamic or aspartic unites being between $0<M \leq 0.5$;

When several hydrophobic radicals are borne by a co-polyamino acid, then they are identical or different,
The degree of polymerization DP in glutamic or aspartic units for the PLG chains is comprised from 5 to 250;
Free carboxylic acids being in the form of an alkaline cation salt chosen from the group consisting of $Na^+$ and $K^+$.

In one embodiment, the composition is characterized in that the composition does not comprise basal insulin for which the isoelectric point pI is comprised from 5.8 to 8.5.

In one embodiment, the composition is characterized in that the composition does not comprise GLP-1, a GLP-1 analogue or GLP-1 receptors agonist, currently called GLP-1 RA.

In one embodiment, the composition is characterized in that the composition does not comprise either basal insulin, with an isoelectric point pI from 5.8 and 8.5, nor GLP-1, a GLP-1 analogue or GLP-1 receptors agonist, currently called GLP-1 RA.

In one embodiment, the invention relates to a composition, free of basal insulin, for which the isoelectric point pI is comprised from 5.8 to 8.5, in the form of an injectable aqueous solution, for which the pH is comprised from 6.0 to 8.0, comprising at least:
a) Amylin, an amylin receptor agonist and an amylin analogue;
b) A co-polyamino acid bearing carboxylate charges and hydrophobic radicals Hy, said co-polyamino acid being constituted of glutamic or aspartic units and said hydrophobic radicals -Hy chosen among the radicals according to formula X as defined below:

Formula X

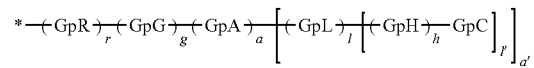

in which
GpR is chosen among the radicals according to formulas VII, VII' or VII":

Formula VII
or

Formula VII'
or

Formula VII"
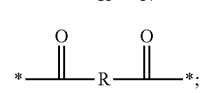

Identical or different GpG and GpH are chosen among the radicals according to formulas XI or XI';

Formula XI
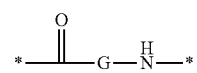

Formula XI'
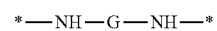

GpA is chosen among the radicals according to formula VIII

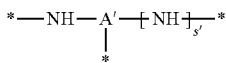

Formula VIII

In which A' is chosen among the radicals according to formulas VIII', VIII" or VIII'''

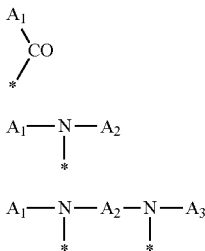

Formula VIII'

Formula VIII"

Formula VIII'''

-GpL is chosen among the radicals according to formula XII

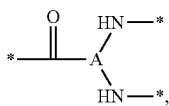

Formula XII

GpC is a radical according to formula IX:

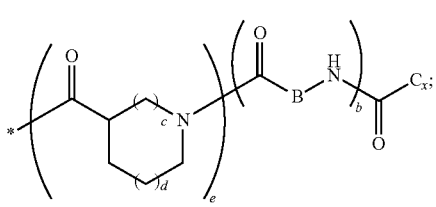

Formula IX

* indicate the attachment sites of the different groups bound by amide functions;
a is an integer equal to 0 or to 1 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g, h or l is different from 0;
l is an integer equal to 0 or to 1 and l'=1 if l=0 and l'=2 if l=1;
r is an integer equal to 0, to 1 or to 2, and
s' is an integer equal to 0 or to 1;
And if e is different from 0, then at least one of g, h or l is different from 0;
And if a=0, then l=0;
A, $A_1$, $A_2$ and $A_3$ identical or different, are linear or branched alkyl radicals comprising from 1 to 8 carbon atoms and, optionally, substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms.
$C_x$ is a monovalent, linear or branched, alkyl radical optionally comprising a cyclic part, in which x indicates the number of carbon atoms, and:
When the hydrophobic radical -Hy bears 1 -GpC, then $9 \leq x \leq 25$,
When the hydrophobic radical -Hy bears 2 -GpC, then $9 \leq x \leq 15$,
When the hydrophobic radical -Hy bears 3 -GpC, then $7 \leq x \leq 13$,
When the hydrophobic radical -Hy bears 4 -GpC, then $7 \leq x \leq 11$,
When the hydrophobic radical -Hy bears at least 5 -GpC, then $6 \leq x \leq 11$,
G is a linear or branched divalent alkyl radical of 1 to 8 carbon atoms, said alkyl radical bearing one or more free carboxylic acid functions.
R is a radical chosen from the group consisting of a divalent, linear or branched alkyl radical comprising from 1 to 12 carbon atoms, a divalent, linear or branched alkyl radical comprising from 1 to 12 carbon atoms bearing one or more $-CONH_2$ functions or an unsubstituted ether or polyether radical comprising from 4 to 14 carbon atoms and 1 to 5 oxygen atoms.
The hydrophobic radicals -Hy according to formula X being bound to the PLG:
via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG.
The ratio M between the number of hydrophobic radicals and the number of glutamic or aspartic unites being between $0 < M \leq 0.5$;
When several hydrophobic radicals are borne by a co-polyamino acid, then they are identical or different,
The degree of polymerization DP in glutamic or aspartic units for the PLG chains is comprised from 5 to 250;
Free carboxylic acids being in the form of an alkaline cation salt chosen from the group consisting of $Na^+$ and $K^+$.
By "alkyl radical" is meant a linear or branched carbon chain which does not comprise a heteroatom.
The co-polyamino acid is a statistical co-polyamino acid in the chain of glutamic and/or aspartic units.
Said co-polyamino acid bearing carboxylate charges and hydrophobic radicals Hy is soluble in aqueous solution at a pH from 6.0 to 8.0, at a temperature of 25° C. and at a concentration of less than 100 mg/ml.
The compositions in the form of an injectable aqueous solution according to the invention are clear solutions. By "clear solution", is meant compositions which meet the criteria described in the American and European pharmacopoeias regarding injectable solutions. In the US pharmacopoeia, the solutions are defined in section <1151> referring to injection (<1>) (referring to <788> according to USP 35 and specified in <788> according to USP 35 and in <787>, <788> and <790> USP 38 (beginning with Aug. 1, 2014), according to USP 38). In the European pharmacopoeia, injectable solutions must meet the criteria given in sections 2.9.19 ans 2.9.20.

By "soluble" is meant, suitable for the preparation of a clear solution, free of particles, at a concentration of less than 100 mg/ml in distilled water at 25° C.

By basal insulin with an isoelectric point from 5.8 to 8.5 is meant an insulin insoluble at pH 7 and for which the duration of action is comprised from 8 to 24 hours, or greater than 24 hours in standard diabetes models.

The * in formulas indicate the attachment sites of the various elements represented.

In one embodiment, Hy comprises more than 30 carbon atoms.

In one embodiment, the composition according to the invention is characterized in that Hy comprises from 15 to 100 carbon atoms.

In one embodiment, the composition according to the invention is characterized in that Hy comprises from 30 to 70 carbon atoms.

In one embodiment, the composition according to the invention is characterized in that Hy comprises from 40 to 60 carbon atoms.

In one embodiment, the composition according to the invention is characterized in that Hy comprises from 20 to 30 carbon atoms.

In one embodiment, when a'=1, x is comprised from 11 to 25 ($11 \leq x \leq 25$). Specifically, when x is comprised from 15 and 16 (x=15 or 16), then r=1 and R is an ether or polyether radical and when x is greater than 17 ($x \geq 17$), then r=1 and R is an ether or polyether radical.

In one embodiment, when a'=2, x is comprised from 9 and 15 ($9 \leq x \leq 15$).

In one embodiment, the composition is characterized in that the pH is comprised from 6.6 to 7.8.

In one embodiment, the composition is characterized in that the pH is comprised from 7.0 to 7.8.

In one embodiment, the composition is characterized in that the pH is comprised from 6.8 to 7.4.

In one embodiment, when r=2, then the GpR group bound to the PLG is chosen among the GpR according to formula VII.

In one embodiment, when r=2, then the GpR group bound to the PLG is chosen among the GpR according to formula VII and the second GpR is chosen among the GpR according to formula VII".

In one embodiment, when r=2, then the GpR group bound to the PLG is chosen among the GpR according to formula VII".

In one embodiment, when r=2, then the GpR group bound to the PLG is chosen among the GpR according to formula VII" and the second GpR is chosen among the GpR according to formula VII.

In one embodiment, at least one of g, h or l is different from 0.

In one embodiment, at most one of g, h or l is different from 0.

In one embodiment, at least one of g and his equal to 1.
In one embodiment, a=1 and l=1.

In one embodiment, if l=0, at least one of g or h is equal to 0.

In one embodiment, if l=1, at least one of g and his equal to 0.

In one embodiment, g=h=0, a=1, GpA is a radical according to formula VIII with s'=1 and A' according to formula VIII' or VIII", and l=1.

In one embodiment, at least one of g and his equal to 1.

In one embodiment, a=0.

In one embodiment, $g+h \geq 2$.

In one embodiment, g is greater than or equal to 2 ($g \geq 2$).

In one embodiment, h is greater than or equal to 2 ($g \geq 2$).

In one embodiment, $g+h \geq 2$ and 1 is equal to 0 (a=l=0).

In one embodiment, $g+h \geq 2$ and b is equal to 0 (b=0).

In one embodiment, g or h is greater than or equal to 2 ($g \geq 2$) and b is equal to 0.

In one embodiment, $g+h \geq 2$, b is equal to 0 (b=0) and e is equal to 1 (e=1).

In one embodiment, g or h is greater than or equal to 2 ($g \geq 2$) b is equal to 0 (b=0) and e is equal to 1 (e=1).

In one embodiment, said at least one hydrophobic radical -Hy is chosen among the radicals according to formula X in which r=2 according to formula Xc', as defined below:

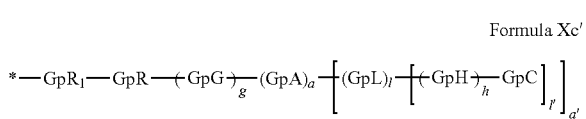

Formula Xc' in which $GpR_1$ is a radical according to formula VII.

Formula VII in which GpR, GpG, GpA, GpL, GpH, GpC, R, a, a', g, h, l and l' have the definitions given above.

In one embodiment, said hydrophobic radical -Hy is chosen among the radicals according to formula X in which r=2 according to formula Xc', as defined below:

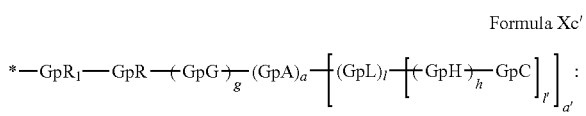

Formula Xc' in which $GpR_1$ is a radical according to formula VII".

Formula VII"

In which GpR, GpG, GpA, GpL, GpH, GpC, R, a, a', g, h, l and l' have the definitions given above.

In one embodiment, said hydrophobic radical -Hy is chosen among the radicals according to formula X in which l=0, according to formula Xd as defined below.

Formula Xd

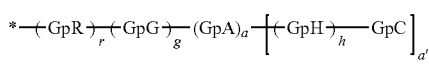

in which
GpR is chosen among the radicals according to formulas VII, VII' or VII":

Formula VII

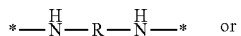  or

Formula VII'

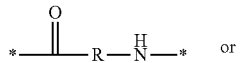  or

Formula VII"

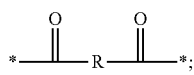;

GpG is chosen among the radicals according to formulas XI or XI':

Formula XI

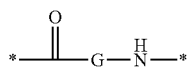

Formula XI'

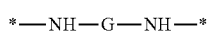

GpA is chosen among the radicals according to formula VIII in which s'=1 represented by formula VIIIa or formula VIII in which and s'=0 represented by formula VIIIb:

Formula VIIIa

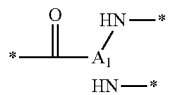

Formula VIIIb

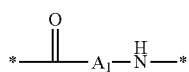

GpC is a radical according to formula IX:

Formula IX

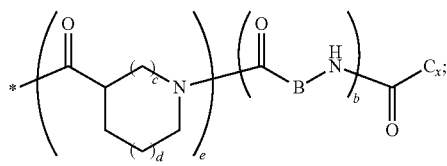

\* indicate the attachment sites of the different groups bound by amide functions;
a is an integer equal to 0 or to 1 and a'=1' if a=0 and a'=1 or a'=2 if a=1;
a' is an integer equal to 1 or to 2 and;
  If a' is equal to 1 then a is equal to 0 or to 1 and GpA is a radical according to formula VIIIb and,
  If a' is equal to 2 then a is equal to 1 and GpA is a radical according to formula VIIIa;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g or h is different from 0;
r is an integer equal to 0, 1 or to 2, and
s' is an integer equal to 0 or to 1;
And if e is different from 0, then at least one of g, h or l is different from 0;
And if a=0, then l=0;
$A_1$ is a linear or branched alkyl radical comprising from 1 to 8 carbon atoms and, optionally, substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms;
$C_x$ is a monovalent, linear or branched, alkyl radical optionally comprising a cyclic part, in which x indicates the number of carbon atoms, and:
  When the hydrophobic radical -Hy bears 1 -GpC, then $9 \leq x \leq 25$,
  When the hydrophobic radical -Hy bears 2 -GpC, then $9 \leq x \leq 15$,
  When the hydrophobic radical -Hy bears 3 -GpC, then $7 \leq x \leq 13$,
  When the hydrophobic radical -Hy bears 4 -GpC, then $7 \leq x \leq 11$,
  When the hydrophobic radical -Hy bears at least 5 -GpC, then $6 \leq x \leq 11$,
G is a alkyl radical of 1 to 8 carbon atoms, said alkyl radical bearing one or more free carboxylic acid functions.
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms.
The hydrophobic radical(s) Hy according to formula X being bound to the PLG:
  via a covalent bond between a carbonyl of the hydrophobic radical -Hy and a nitrogen atom borne by the PLG, thus forming an amide function resulting from the reaction of an amine function borne by the PLG and an acid function borne by the -Hy precursor of the hydrophobic radical, and
  via a covalent bond between a nitrogen atom of the hydrophobic radical -Hy and a carbonyl borne by the PLG. thus forming an amide function resulting from the reaction of an amine function of the -Hy precursor of the hydrophobic radical and an acid function borne by the PLG.
The ratio M between the number of hydrophobic radicals and the number of glutamic or aspartic unites being comprised from $0 < M \leq 0.5$;

When several hydrophobic radicals are borne by a co-polyamino acid, then they are identical or different, Free carboxylic acids being in the form of an alkaline cation salt chosen from the group consisting of Na+ and K+.

In one embodiment said hydrophobe -Hy is chosen among the radicals according to formula X, as defined below, in which l=0, GpA is chosen among the radicals according to formula VIII in which s'=1 and A' is chosen among the radicals according to formulas VIII" or VIII'";

Formula Xd in which

GpR is chosen among the radicals according to formulas VII, VII' or VII":

Formula VII

Formula VII'

Formula VII"

GpG is chosen among the radicals according to formulas XI or XI':

Formula XI

Formula XI'

GpA is chosen among the radicals according to formulas VIIIc or VIIId:

Formula VIIIc

Formula VIIId

GpC is a radical according to formula IX:

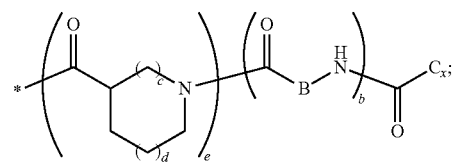

Formula IX

* indicate the attachment sites of the different groups bound by amide functions;
a is an integer equal to 0 or to 1 and a'=1 if a=0 or 2 or 3, if a=1;
a' is an integer equal to 2 or to 3 and;
  if a' is equal to 1 then a is equal to 0 and
  if a' is equal to 2 or 3, then a is equal to 1 and GpA is a radical according to formula VIIIc or VIIId;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 1, to 2, to 3, to 4, to 5 or to 6;
h is an integer equal to 0, to 1, to 2, to 3, to 4, to 5 or to 6, and at least one of g or h is different from 0;
r is an integer equal to 0, 1 or to 2, and
s' is an integer equal to 1;
And if e is different from 0, then at least one of g, h or l is different from 0;
And if a=0, then l=0;
$A_1$, $A_2$, $A_3$, identical or different, are linear or branched alkyl radicals comprising from 1 to 8 carbon atoms and, optionally, substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms;
$C_x$ is a monovalent, linear or branched, alkyl radical optionally comprising a cyclic part, in which x indicates the number of carbon atoms, and:
  When the hydrophobic radical -Hy bears 1 -GpC, then $9 \leq x \leq 25$,
  When the hydrophobic radical -Hy bears 2 -GpC, then $9 \leq x \leq 15$,
  When the hydrophobic radical -Hy bears 3 -GpC, then $7 \leq x \leq 13$,
  When the hydrophobic radical -Hy bears 4 -GpC, then $7 \leq x \leq 11$,
  When the hydrophobic radical -Hy bears at least 5 -GpC, then $6 \leq x \leq 11$,
The hydrophobic radical(s) Hy according to formula X being bound to the PLG:
  via a covalent bond between a carbonyl of the hydrophobic radical and a nitrogen atom borne by the PLG, thus forming an amide function resulting from the reaction of an amine function borne by the PLG and an acid function borne by the precursor -Hy' of the hydrophobic radical, and
  via a covalent bond between a nitrogen atom of the hydrophobic radical and a carbonyl borne by the PLG, thus forming an amide function resulting from the reaction of an amine function of the -Hy precursor of the hydrophobic radical and an acid function borne by the PLG.

G is a alkyl radical of 1 to 8 carbon atoms, said alkyl radical bearing one or more free carboxylic acid functions.

R is a radical chosen from the group consisting of a divalent, linear or branched alkyl radical comprising from 1 to 12 carbon atoms, a divalent, linear or branched alkyl radical comprising from 1 to 12 carbon atoms bearing one or more —CONH₂ functions or an unsubstituted ether or polyether radical comprising from 4 to 14 carbon atoms and 1 to 5 oxygen atoms.

the ratio M between the number of hydrophobic radicals and the number of glutamic or aspartic unites being between 0<M≤0.5;

When several hydrophobic radicals are borne by a co-polyamino acid, then they are identical or different, Free carboxylic acids being in the form of an alkaline cation salt chosen from the group consisting of Na⁺ and K⁺.

In one embodiment, r=0 and the hydrophobic radical according to formula X is bound to the PLG via a covalent bond between a carbonyl of the hydrophobic radical and a nitrogen atom borne by the PLG, thus forming an amide function resulting from the reaction of an amine function borne by the PLG precursor and an acid function borne by the precursor Hy' of the hydrophobic radical, and In one embodiment, r=1 and the hydrophobic radical according to formula X is bound to the PLG:
via a covalent bond between a nitrogen atom of the hydrophobic radical and a carbonyl borne by the PLG, thus forming an amide function resulting from the reaction of an amine function of the precursor -Hy' of the hydrophobic radical and an acid function borne by the PLG, or
via a covalent bond between a carbonyl of the hydrophobic radical function resulting from the reaction of an acid function of the precursor -Hy' of the hydrophobic radical -Hy and an amine function borne by the PLG.

In one embodiment, if GpA is a radical according to formula VIIIc and r=1 or 2, then:
the GpC are bound, directly or indirectly, to N┌₁ and N┌┌ and the PLG is bound, directly or indirectly, via GpR to N ┘┘, or
the GpC are bound, directly or indirectly, to N└└ and N└└ and the PLG is bound, directly or indirectly, via GpR to N ┐┐; or
the GpC are bound, directly or indirectly, to N ┌┌ and N┌┌ and the PLG is bound, directly or indirectly, via GpR to N ┘┘.

In one embodiment, if GpA is a radical according to formula VIIIc and r=0, then:
the GpC are bound, directly or indirectly, to N└└ and N└└ and the PLG is bound, directly or indirectly, to N ┌┌; or
the GpC are bound, directly or indirectly, to N ┌┌ and N┌┌ and the PLG is bound, directly or indirectly, to N└└; or
the GpC are bound, directly or indirectly, to N└└ and N└└, and the PLG is bound, directly or indirectly, to N ┌┌.

In one embodiment, if GpA is a radical according to formula VIIId and r=1 or 2, then
the GpC are bound, directly or indirectly, to N ┐┐, N└└ and N┌┐ and the PLG is bound directly or indirectly, via GpR to N└└; or the GpC are bound, directly or indirectly, to N ┐┐, N ┌┌ and N ┌┐ and the PLG, directly or indirectly, is bound via GpR to N└└; or
the GpC are bound, directly or indirectly, to N └└, N ┘┘ and N__ and the PLG, directly or indirectly, is bound via GpR to N ┐┐; or
the GpC are bound, directly or indirectly, to N ┐┐, N ┐┐ and N-- and the PLG is bound, directly or indirectly, via GpR to N ┘┘.

In one embodiment, if GpA is a radical according to formula VIIId and r=0, then
the GpC are bound, directly or indirectly, to N ┘┘, N ┘┘ and N__ and PLG is bound directly or indirectly, to N ┐┐; or
the GpC are bound, directly or indirectly, to N ┘┘, N ┘┘ and N-- and PLG is bound directly or indirectly, to N ┘┘; or
the GpC are bound, directly or indirectly, to N ┘└, N ┘┘ and N__ and the PLG is bound, directly or indirectly, to N └┘; or
the GpC are bound, directly or indirectly, to N ┘└, N└└ and N ┘┘ and the PLG is bound, directly or indirectly, to N ┘┘

In one embodiment, said at least one hydrophobic radical -Hy is chosen among the radicals according to formula X in which a=1 and a'=1 according to formula Xa, as defined below:

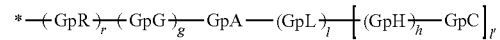

Formula Xa in which GpA is a radical according to formula VIII and A' is chosen among the radicals according to formula VIII' with s'=0 and GpA is a radical according to formula VIIIb.

Formula VIIIb and GpR, GpG, GpL, GpH, GpC, A₁, r, g, h, l and l' have the definitions given above.

In one embodiment, said at least one hydrophobic radical -Hy is chosen among the radicals according to formula X in which a=1 according to formula Xb, as defined below:

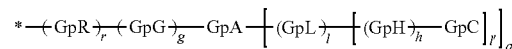

Formula Xb in which GpA is a radical according to formula VIII and A' is chosen among the radicals according to formula VIII' with s'=1 and GpA is a radical according to formula VIIIa.

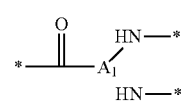

Formula VIIIa

And GpR, GpG, GpL, GpH, GpC, $A_1$, a', r, g, h, l and l' have the definitions given above.

In one embodiment, said at least one hydrophobic radical -Hy is chosen among the radicals according to formula X in which a=1 as defined below:

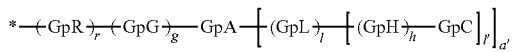

Formula Xb in which GpA is a radical according to formula VIII and A is chosen among the radicals according to formula VIII''' with s'=1 and GpA is a radical according to formula VIIIc.

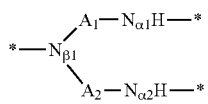

Formula VIIIc

And GpR, GpG, GpL, GpH, GpC, $A_1$, $A_2$, r, g, h, a', l and l' have the definitions given above.

In one embodiment, said at least one hydrophobic radical -Hy is chosen among the radicals according to formula X in which a=1 as defined below:

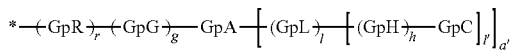

Formula Xb in which GpA is a radical according to formula VIII and A is chosen among the radicals according to formula VIII''' with s'=1, and GpA is a radical according to formula VIIId.

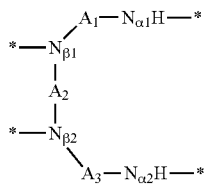

Formula VIIId

And GpR, GpG, GpL, GpH, GpC, $A_1$, $A_2$, $A_3$, a', r, g, h, l and l' have the definitions given above.

In one embodiment, said at least one hydrophobic radical -Hy is chosen among the radicals according to formula X in which r=1 according to formula Xc, as defined below:

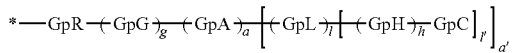

Formula Xc in which GpR is a radical according to formula VII.

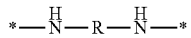

Formula VII

And GpR, GpA, GpL, GpH, GpC, R, a, g, h, l, a' and l' have the definitions given above.

In one embodiment, said at least one hydrophobic radical -Hy is chosen among the radicals according to formula X in which r=1 according to formula Xc, as defined below:

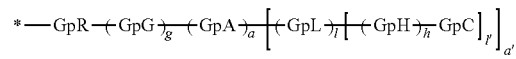

Formula Xc in which GpR is a radical according to formula VII'.

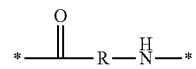

Formula VII'

And GpR, GpA, GpL, GpH, GpC, R, a, g, h, l, a' and l' have the definitions given above.

In one embodiment, said at least one hydrophobic radical -Hy is chosen among the radicals according to formula X in which r=1 according to formula Xc, as defined below:

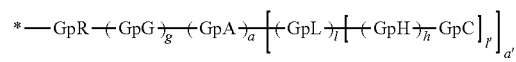

Formula Xc in which GpR is a radical according to formula VII''.

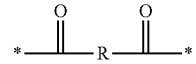

Formula VII''

And GpR, GpA, GpL, GpH, GpC, R, a, g, h, l, a' and l' have the definitions given above.

In one embodiment, said at least one hydrophobic radical -Hy is chosen among the radicals according to formula X as defined below:

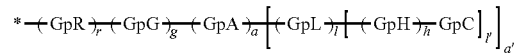

Formula X in which GpC is a radical according to formula IX in which e=0 and GpC is a radical according to formula IXa'.

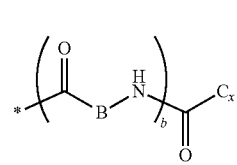

Formula IXa'

In one embodiment, said at least one hydrophobic radical -Hy is chosen among the radicals according to formula X as defined below:

Formula X

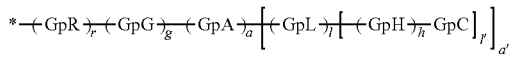

in which GpC is a radical according to formula IX in which e=1, b=0 and GpC is a radical according to formula IXd'.

Formula IXb'

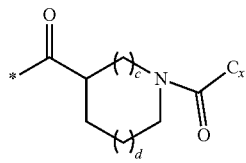

In one embodiment, said at least one hydrophobic radical -Hy is chosen among the radicals according to formula X as defined below:

Formula X

in which GpC is a radical according to formula IX in which e=1 and GpC is a radical according to formula IXd'.

Formula IXd'

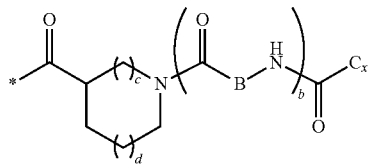

In one embodiment, said at least one hydrophobic radical -Hy is chosen among the radicals according to formula X in which r, g, a, l, h are equal to 0, according to formula Xd' as defined below:

*-GpC  Formula Xd'.

In one embodiment, said at least one hydrophobic radical -Hy is chosen among the radicals according to formula X in which r, g, a, l, h are equal to 0, according to formula Xd' as defined below:

*-GpC  Formula Xd' in which GpC is a radical according to formula IX in which e=0, b=0 and GpC is a radical according to formula IXc'.

IXc'

In one embodiment, the composition according to the invention is characterized in that said hydrophobic radicals are chosen among the hydrophobic radicals according to formula X in which GpA is a radical according to formula VIIIb, a'=1 and l=0.

Formula Xe

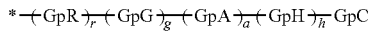

GpR, GpG, GpA, GpH, GpC, r, g, hand a have the definitions given above.

In one embodiment, the composition according to the invention is characterized in that said hydrophobic radicals are chosen among the hydrophobic radicals according to formula X in which a'=2 and a=1 and l=0 represented by formula Xf below:

Formula Xf

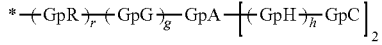

GpR, GpG, GpA, GpH, GpC, r, g and h have the definitions given above.

In one embodiment, the composition according to the invention is characterized in that said hydrophobic radicals are chosen among the hydrophobic radicals according to formula X in which h=0, l=0 and l'=1 represented by formula Xg below:

Formula Xg

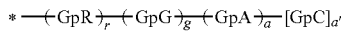

GpR, GpG, GpA, GpC, r, g, a and a' have the definitions given above.

In one embodiment, the composition according to the invention is characterized in that said hydrophobic radicals are chosen among the hydrophobic radicals according to formula X in which h=0, a'=1 represented by formula Xh below:

Formula Xh

GpR, GpG, GpA, GpC, r, a and g have the definitions given above.

In one embodiment, the composition according to the invention is characterized in that said hydrophobic radicals are chosen among the hydrophobic radicals according to formula X in which h=0, a'=2 and a=1 represented by formula Xi below:

Formula Xi

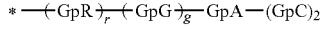

GpR, GpG, GpA, GpC, r and g have the definitions given above.

In one embodiment, a=0.,
In one embodiment, h=1 and g=0,
In one embodiment, h=0 and g=1,
In one embodiment, r,=0, g=1 and h=0.
In one embodiment, r=1 and GpR is chosen among the radicals according to formula VII' or VII" and h=0.
In one embodiment, r=1, g=0 and GpR is a radical according to formula VII' and h=0.
In one embodiment, r=1, g=0 and GpR is a radical according to formula VII' and h=1.
In one embodiment, r=1, g=0, GpR is a radical according to formula VII', GpA is chosen among the radicals according to formula VIIIa or VIIIb, and h=0.
In one embodiment, r=1, g=0, GpR is a radical according to formula VII', GpA is chosen among the radicals according to formula VIIa' or VIIIb and h=1.
In one embodiment, r=1, g=0 and GpR is a radical according to formula VII', GpA is a radical according to formula VIIIa and h=0.
In one embodiment, r=1, g=0, GpR is a radical according to formula VII', GpA is a radical according to formula VIIIa and h=1.
In one embodiment, r=1, g=0, GpR is a radical according to formula VII', GpA is a radical according to formula VIIIb and h=0.
In one embodiment, r=1, g=0, GpR is a radical according to formula VII', GpA is a radical according to formula VIIIb and h=1.
In one embodiment, r=0 and GpA is chosen among the radicals according to formulas VIIIa and VIIIb.
In one embodiment, r=0, g=0 and GpA is chosen among the radicals according to formulas VIIIa and VIIIb.
In one embodiment, r=0, GpA is chosen among the radicals according to formula VIIIa and VIIIb and h=0.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 12 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 6 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 6 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 4 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 4 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising 2 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 1 to 11 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 1 to 6 carbon atoms.
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 5 carbon atoms and bearing or more amide functions (—CONH2).
In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising from 2 to 5 carbon atoms and bearing or more amide functions (—CONH2).
In one embodiment, the composition is characterized in that the hydrophobic radical according to formulas X, Xc', Xa, Xb, Xc, Xd, Xe, Xf, Xg, Xh and Xi is a radical in which R is a is a radical chosen from the group consisting of the radicals represented by the formulas below:

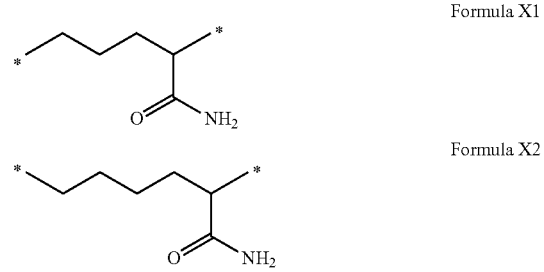

Formula X1

Formula X2

In one embodiment, the composition is characterized in that the hydrophobic radical according to formulas X, Xc', Xa, Xb, Xc, Xd, Xe, Xf, Xg, Xh and Xi is a radical in which R is a radical according to formula X1.
In one embodiment, the composition is characterized in that the hydrophobic radical according to formulas X, Xc', Xa, Xb, Xc, Xd, Xe, Xf, Xg, Xh and Xi is a radical in which R is a radical according to formula X2.
In one embodiment, the composition is characterized in that the hydrophobic radical according to formula X is a radical in which R is bound to the co-polyamino acid via an amide function borne by the carbon in delta or epsilon position (or in position 4 or 5) with respect to the amide function (—CONH2).
In one embodiment, the composition is characterized in that the hydrophobic radical according to formulas X, Xc', Xa, Xb, Xc, Xd, Xe, Xf, Xg, Xh and Xi is a radical in which R is an unsubstituted linear ether or polyether radical comprising from 4 to 14 carbon atoms and from 1 to 5 oxygen atoms.
In one embodiment, the composition is characterized in that the hydrophobic radical according to formulas X, Xc', Xa, Xb, Xc, Xd, Xe, Xf, Xg, Xh and Xi is a radical in which R is an ether radical.
In one embodiment, the composition is characterized in that the hydrophobic radical according to formulas X, Xc', Xa, Xb, Xc, Xd, Xe, Xf, Xg, Xh and Xi is a radical in which R is an ether radical comprising from 4 to 6 carbon atoms.

In one embodiment, the composition is characterized in that the hydrophobic radical according to formulas X, Xc', Xa, Xb, Xc, Xd, Xe, Xf, Xg, Xh and Xi is a radical in which R is a divalent, linear alkyl radical comprising 6 carbon atoms.

In one embodiment, the composition is characterized in that the hydrophobic radical according to formulas X, Xc', Xa, Xb, Xc, Xd, Xe, Xf, Xg, Xh and Xi is a radical in which R is an ether radical represented by formula

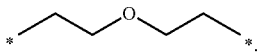

In one embodiment, the composition is characterized in that the hydrophobic radical according to formulas X, Xc', Xa, Xb, Xc, Xd, Xe, Xf, Xg, Xh and Xi is a radical in which R is a polyether radical.

In one embodiment, the composition is characterized in that the hydrophobic radical according to formulas X, Xc', Xa, Xb, Xc, Xd, Xe, Xf, Xg, Xh and Xi is a radical in which R is a linear polyether radical comprising from 6 to 10 carbon atoms and from 2 to 3 oxygen atoms.

In one embodiment, the composition is characterized in that the hydrophobic radical according to formulas X, Xc', Xa, Xb, Xc, Xd, Xe, Xf, Xg, Xh and Xi is a radical in which R is a is a polyether radical chosen from the group consisting of the radicals represented by the formulas below:

Formula X3

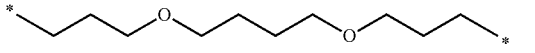

Formula X4

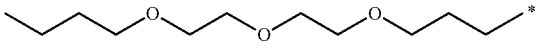

Formula X5

Formula X6

In one embodiment, the composition is characterized in that the hydrophobic radical according to formulas X, Xc', Xa, Xb, Xc, Xd, Xe, Xf, Xg, Xh and Xi is a radical in which R is a radical according to formula X3.

In one embodiment, the composition is characterized in that the hydrophobic radical according to formulas X, Xc', Xa, Xb, Xc, Xd, Xe, Xf, Xg, Xh and Xi is a radical in which R is a radical according to formula X4.

In one embodiment, the composition is characterized in that the hydrophobic radical according to formulas X, Xc', Xa, Xb, Xc, Xd, Xe, Xf, Xg, Xh and Xi is a radical in which R is a is a polyether radical chosen from the group consisting of the radicals represented by the formulas X5 and X6 below:

In one embodiment, the composition is characterized in that the hydrophobic radical according to formulas X, Xc', Xa, Xb, Xc, Xd, Xe, Xf, Xg, Xh and Xi is a radical in which R is a polyether radical according to formula X5.

In one embodiment, the composition is characterized in that the hydrophobic radical according to formulas X, Xc', Xa, Xb, Xc, Xd, Xe, Xf, Xg, Xh and Xi is a radical in which R is a polyether radical according to formula X6.

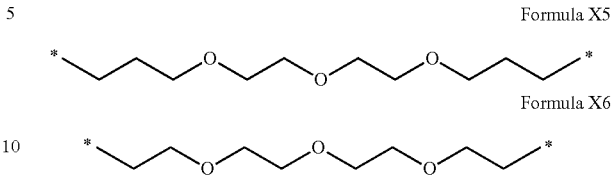

Formula X5

Formula X6

In one embodiment, the composition is characterized in that the hydrophobic radical according to formulas X, Xc', Xa, Xb, Xc, Xd, Xe, Xf, Xg, Xh and Xi is a radical in which the GpG and/or GpH radical is according to formula XI' in which G is an alkyl radical comprising 6 carbon atoms represented by formula Z below:

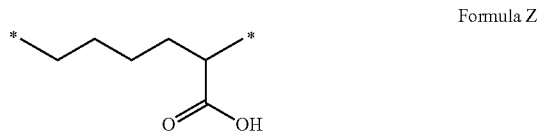

Formula Z

In one embodiment, the composition is characterized in that the hydrophobic radical according to formulas X, Xc', Xa, Xb, Xc, Xd, Xe, Xf, Xg, Xh and Xi is a radical in which the GpG and/or GpH is comprised according to formula XI in which G is an alkyl radical comprising 4 carbon atoms represented by formula Z below:

Formula Z'

In one embodiment, the composition is characterized in that the hydrophobic radical according to formulas X, Xc', Xa, Xb, Xc, Xd, Xe, Xf, Xg, Xh and Xi is a radical in which the GpG and/or GpH radical is comprised according to formula XI in which G is an alkyl radical comprising 4 carbon atoms represented by —(CH2)2-CH(COOH)—.

In one embodiment, the composition is characterized in that the hydrophobic radical according to formulas X, Xc', Xa, Xb, Xc, Xd, Xe, Xf, Xg, Xh and Xi is a radical in which the GpG and/or GpH radical is comprised according to formula XI which G is an alkyl radical comprising 4 carbon atoms represented by —CH((CH2)2COOH)—.

In one embodiment, the composition is characterized in that the hydrophobic radical according to formulas X, Xc', Xa, Xb, Xc, Xd, Xe, Xf, Xg, Xh and Xi is a radical in which the GpG and/or GpH radical is comprised according to formula XI in which G is an alkly radical comprising 3 carbon atoms represented by formula —CH2-CH—(COOH).

In one embodiment, the composition is characterized in that the hydrophobic radical according to formulas X, Xc', Xa, Xb, Xc, Xd, Xe, Xf, Xg, Xh and Xi is a radical in which the GpG and/or GpH is comprised according to formula XI in which G radical is an alkly radical comprising 3 carbon atoms represented by —CH(CH2)COOH)—.

In one embodiment, the composition is characterized in that the hydrophobic radical according to formulas X, Xc', Xa, Xb, Xc, Xd, Xe, Xf, Xg, Xh and Xi is a radical in which GpA radical is comprised according to formula VIII and in which $A_1$, $A_2$ or $A_3$ is chosen from the group consisting of the radicals represented by the formulas below:

Formula Y1

Formula Y2

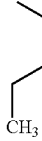

Formula Y3

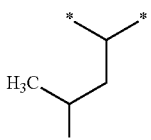

Formula Y4

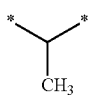

Formula Y5

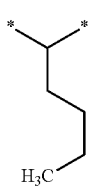

Formula Y6

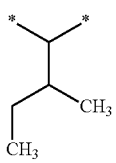

Formula Y7

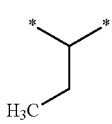

Formula Y8

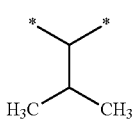

Formula Y9

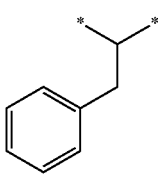

Formula Y10

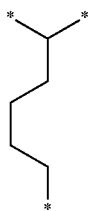

In one embodiment, the composition is characterized in that the hydrophobic radical according to formulas X, Xc', Xd, Xa, Xb, Xd', Xc, Xe, Xf, Xg, Xh and Xi is a radical in which the radical GpC according to formula IX is chosen from the group consisting of the radicals of formulas IXe, IXf or IXg represented below:

Formula IXe

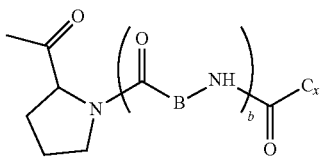

Formula IXf

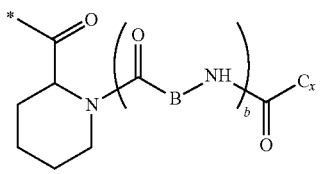

Formula IXg

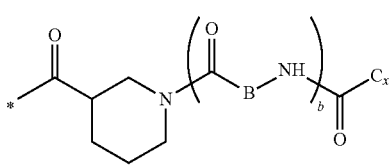

In one embodiment, the composition is characterized in that the hydrophobic radical according to formulas X, Xc', Xd, Xa, Xb, Xd', Xc, Xe, Xf, Xg, Xh and Xi is a radical in which the radical GpC according to formula IX is chosen from the group consisting of the radicals of formulas IXe, IXf or IXg, in which b is equal to 0, responding respectively to formulas IXh, IXi and IXj represented below:

Formula IXh

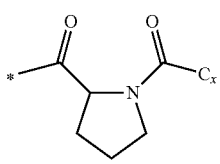

Formula IXi

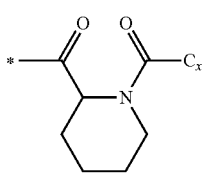

-continued

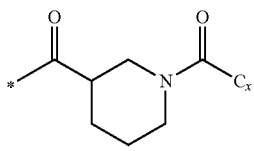

Formula IXj

In one embodiment, the composition is characterized in that the hydrophobic radical according to formulas X, Xc', Xd, Xa, Xb, Xd', Xc, Xe, Xf, Xg, Xh and Xi is a radical in which the GpC radical responds to the formula IX or IXe, in which b=0 and responds to the formula IXh.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the linear alkyl radicals.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the branched alkyl radicals.

In one embodiment, the composition is characterized in that the hydrophobic radical according to formulas X, Xc', Xd, Xa, Xb, Xd', Xc, Xd, Xe, Xf, Xg, Xh and Xi is a radical in which Cx is chosen from the group consisting of the alkyl radicals comprising from 19 to 14 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the radicals represented by the formulas below:

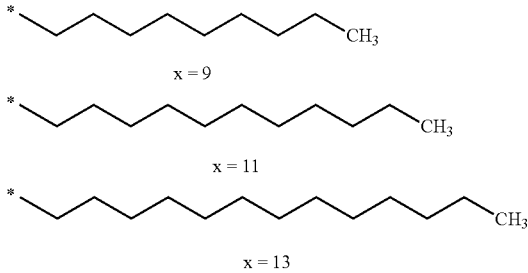

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals comprising from 15 to 16 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the radicals represented by the formulas below:

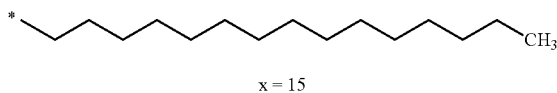 [SMILES: CCCCCCCCCCCCCCCC]

x = 15

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the radicals represented by the formulas below:

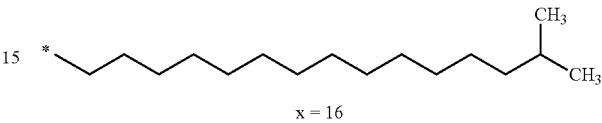

x = 16

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals comprising from 17 and 25 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals comprising from 17 and 18 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals represented by the formulas below:

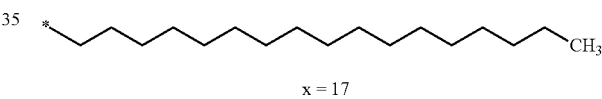

x = 17

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals comprising from 18 and 25 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which Cx is chosen from the group consisting of the alkyl radicals represented by the formulas below:

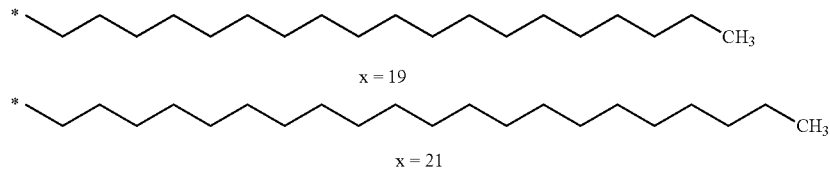

In one embodiment, the composition is characterized in that the hydrophobic radical according to formulas X, Xc', Xd, Xa, Xb, Xd', Xc, Xe, Xf, Xg, Xh and Xi in which the GpC radical according to formula IX is chosen from the group consisting of the radicals in which Cx is chosen from the group consisting of alkyl radicals comprising from 14 to 15 carbon atoms.

In one embodiment, the composition is characterized in that the hydrophobic radical according to formulas X, Xc', Xd, Xa, Xb, Xd', Xc, Xe, Xf, Xg, Xh and Xi is a radical in which GpC radical according to formula IX is chosen from the group consisting of the radicals in which Cx is chosen from the group consisting of the radicals represented by the formulas below:

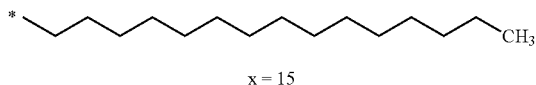 [SMILES: CCCCCCCCCCCCCCCC]

x = 15

In one embodiment, the co-polyamino acid is chosen from the co-polyamino acids fro formula XXXb in which the hydrophobic radical -Hy is chosen from the group of hydrophobic radicals according to formulas X, Xc', Xd Xa, Xb, Xc, Xe, Xg et Xh in which a'=1 and l'=1 and GpC is a radical according to formula IXe.

In one embodiment, the co-polyamino acid is chosen from the co-polyamino acids fro formula XXXb in which the hydrophobic radical -Hy is chosen from the group of hydrophobic radicals according to formulas X, Xc', Xd, Xa, Xb, Xc, Xe, Xg et Xh in which a'=1 and l'=1 and GpC is a radical according to formula IX in which e=0.

In one embodiment, the co-polyamino acid is chosen from the co-polyamino acids fro formula XXXb in which the hydrophobic radical -Hy is chosen from the group of hydrophobic radicals according to formulas X, Xc', Xd, Xa, Xb, Xc, Xf, Xg et Xi in which a'=2 or l'=2 and GpC is a radical according to formula IXe.

In one embodiment, the co-polyamino acid is chosen from the co-polyamino acids fro formula XXXb in which the hydrophobic radical -Hy is chosen from the group of hydrophobic radicals according to formulas X, Xc', Xd, Xa, Xb, Xc, Xf, Xg et Xi in which a'=2 and l'=2 and GpC is a radical according to formula IX in which e=0.

In one embodiment, the co-polyamino acid is chosen from the co-polyamino acids fro formula XXXa in which the hydrophobic radical -Hy is chosen from the group of hydrophobic radicals according to formulas X, Xc', Xd, Xa, Xb, Xc, Xe, Xg et Xh in which a'=1 and l'=1 and GpC is a radical according to formula IXe.

In one embodiment, the co-polyamino acid is chosen from the co-polyamino acids according to formula XXXa in which the hydrophobic radical -Hy is chosen from the group of hydrophobic radicals according to formulas X, Xc', Xd, Xa, Xb, Xc, Xf, Xg et Xi in which a'=2 or l'=2 and GpC is a radical according to formula IXe.

In one embodiment, the co-polyamino acid is chosen from the group of co-polyamino acids according to formula X, in which GpR is a radical according to formula VII, GpH is a radical according to formula XI and GpC is a radical according to formula IX in which e=1 and b=0.

In one embodiment, the co-polyamino acid is chosen from the group of co-polyamino acids according to formula X, in which GpR is a radical according to formula VII, GpH is a radical according to formula XI and GpC is a radical according to formula IX in which e=1 and b=0 and x=13.

In one embodiment, the co-polyamino acid is a poly-L-sodium glutamate, modified at one of its extremities according to the formula represented below, described in example B1.

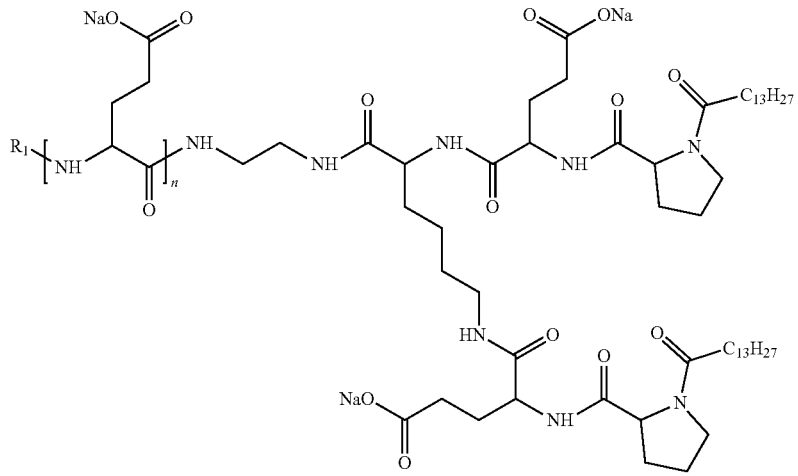

i = 0.038, DP = 26
R₁ = H or pyroglutamate

In one embodiment, the co-polyamino acid is a poly-L-sodium glutamate, modified at one of its extremities according to the formula represented below, described in example B18.

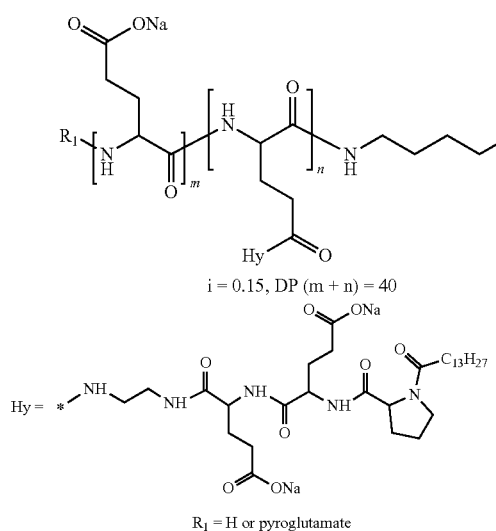

B18 i = 0.15, DP (m + n) = 40

$R_1$ = H or pyroglutamate

In the formulas, the * indicate the attachment sites of the hydrophobic radicals to the PLG or between the different groups GpR, GpG, GpA, GpL and GpC to form amide functions.

The Hy radicals are attached to the PLG via amide functions.

The Hy, GpR, GpG, GpA, GpL and GpC radicals are each independently identical or different from one residue to another.

In one embodiment, the composition is characterized in that the co-polyamino acid bearing carboxylate charges and hydrophobic radicals is chosen among the co-polyamino acids according to formula XXX below:

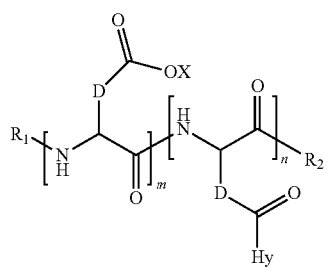

Formula XXX in which,
D represents, independently, either a —$CH_2$— group (aspartic unit) of a —$CH_2$—$CH_2$— group (glutamic unit), Hy is a hydrophobic radical chosen among the hydrophobic radicals according to formulas X, $R_1$ is a hydrophobic radical chosen among the hydrophobic radicals according to formulas X in which r=0 or r=1 and GpR is a radical according to formula VII' or VII", or a radical chosen from the group constituted by an H, a linear acyl group in C2 to C10, a branched acyl group in C3 to C10, a benzyl, an end "amino acid" unit and a pyroglutamate, $R_2$ is a hydrophobic radical chosen among the hydrophobic radicals according to formulas X or an —NR'R", R' and R" radical, identical or different, being chosen from the group consisting of H, the linear, branched or cyclic alkyls in C2 to C10, benzyl and said R' and R" alkyls which may form together one or more carbon saturated, unsaturated and/or aromatic rings and/or may comprise heteroatoms, chosen from the group consisting of O, N and S, X represents a H or a cationic entity chosen from the group comprising the metallic cations;

n+m represents The degree of polymerization DP of the co-polyamino acid, that is the average number of monomeric units per co-polyamino acid chain and $5 \leq n+m \leq 250$.

The co-polyamino acid bearing carboxylate charges and at least one hydrophobic radical according to formula X may also be called "co-polyamino acid" in this description.

We call "statistical co-polyamino acid" a co-polyamino acid bearing corboxylate charges and at least one hydrophobic radical a co-polyamino acid according to formula XXXa.

In one embodiment, the composition is characterized in that the co-polyamino acid bearing carboxylate charges and hydrophobic radicals is chosen among the co-polyamino acids according to formulas XXX, in which $R_1$=$R'_1$ and $R_2$=$R'_2$, according to formula XXXa below:

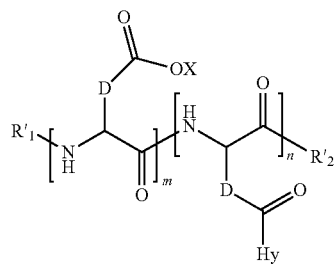

Formula XXXa in which,
m, n, X, D and Hy have the definitions given above, $R'_1$ is a radical chosen from the group consisting of a H, a linear acyl group in C2 to C10, a branched acyl group in C3 to C10, a benzyl, a terminal "amino acid" unit and a pyroglutamate, $R'_2$ is a hydrophobic radical chosen the group consisting of H, the linear, branched or cyclic alkyls in C2 to C10, benzyl and said R' and R" alkyls which may form together one or more carbon saturated, unsaturated and/or aromatic rings and/or may comprise heteroatoms, chosen from the group consisting of O, N and S, We call "statistical co-polyamino acid" a co-polyamino acid bearing corboxylate charges and at least one hydrophobic radical a co-polyamino acid according to formula XXXb.

In one embodiment, the composition is characterized in that the co-polyamino acid bearing carboxylate charges and hydrophobic radicals is chosen among the co-polyamino acids according to formulas XXX, in which n=0, according to formula XXXb below:

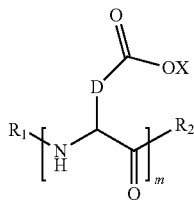

Formula XXXb in which m, X, D, $R_1$ and $R_2$ have the definitions given above and at least $R_1$ or $R_2$ is a hydrophobic radical according to formula X.

In one embodiment, the composition is characterized in that the co-polyamino acid bearing carboxylate charges and hydrophobic radicals is chosen among the co-polyamino acids according to formula XXX, in which n=0, according to formula XXXb and $R_1$ or $R_2$ is a hydrophobic radical according to formula X.

In one embodiment, the composition is characterized in that the co-polyamino acid bearing carboxylate charges and hydrophobic radicals is chosen among the co-polyamino acids according to formula XXXb in which $R_1$ is a hydrophobic radical according to formula X in which r=0, or r=1 and GpR is comprised according to formula VII'.

In one embodiment, the composition is characterized in that the co-polyamino acid bearing carboxylate charges and hydrophobic radicals is chosen among the co-polyamino acids according to formulas XXXb, in which $R_1$ is a hydrophobic radical according to formula X in which r=0 or r=1 and GpR is comprised according to formula VII".

In one embodiment, the composition is characterized in that the co-polyamino acid bearing carboxylate charges and hydrophobic radicals is chosen among the co-polyamino acids according to formula XXXb, in which $R_2$ is a hydrophobic radical according to formula X.

In one embodiment, the composition is characterized in that $R_1$ is a radical chosen from the group consisting of a linear acyl group in $C_2$ à $C_{10}$, a branched acyl group in $C_3$ to $C_{10}$, a benzyl, an end "amino acid" unit and a pyroglutamate.

In one embodiment, the composition is characterized in that $R_1$ is a radical chosen from the group consisting of a linear acyl group in $C_2$ à $C_{10}$, or a branched acyl group in $C_3$ to $C_{10}$.

In one embodiment, the composition is characterized in that the co-polyamino acid bearing carboxylate charges and hydrophobic radicals is chosen among the co-polyamino acids according to formulas XXX, XXXa or XXXb, in which the D group is a —$CH_2$— group (aspartic unit).

In one embodiment, the composition is characterized in that the co-polyamino acid bearing carboxylate charges and hydrophobic radicals is chosen among the co-polyamino acids according to formulas XXX, XXXa or XXXb, in which the D group is a —$CH_2$—$CH_2$— group (glutamic unit).

In one embodiment, the composition is characterized in that the M ratio between the number of hydrophobic radicals and the number of glutamic or aspartic units is comprised from 0.007 to 0.3.

In one embodiment, the composition is characterized in that the M ratio between the number of hydrophobic radicals and the number of glutamic or aspartic units is comprised from 0.01 to 0.3.

In one embodiment, the composition is characterized in that the M ratio between the number of hydrophobic radicals and the number of glutamic or aspartic units is comprised from 0.02 to 0.2.

In one embodiment, the composition according to the invention is characterized in that n+m is comprised from 10 to 250.

In one embodiment, the composition is characterized in that n+m is comprised from 10 to 200.

In one embodiment, the composition is characterized in that n+m is comprised from 15 ato 150.

In one embodiment, the composition is characterized in that n+m is comprised from 15 to 100.

In one embodiment, the composition is characterized in that n+m is comprised from 15 to 80.

In one embodiment, the composition is characterized in that n+m is comprised from 15 to 65.

In one embodiment, the composition is characterized in that n+m is comprised from 20 to 60.

In one embodiment, the composition is characterized in that n+m is comprised from 20 to 50.

In one embodiment, the composition is characterized in that n+m is comprised from 20 to 40.

The invention also relates to a co-polyamino acid bearing carboxylate charges and hydrophobic radicals Hy, said co-polyamino acid being constituted of glutamic or aspartic units and said hydrophobic radicals -Hy chosen among the radicals according to formula X as defined below:

Formula X

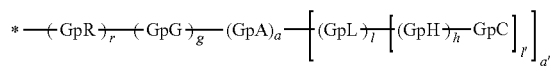

in which

GpR is chosen among the radicals according to formulas VII, VII' or VII":

Formula VII

 or

Formula VII'

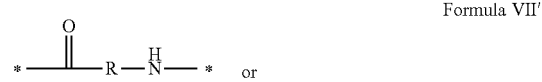 or

Formula VII"

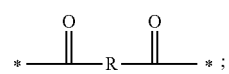 ;

Identical or different GpG and GpH are chosen among the radicals according to formulas XI or XI';

Formula XI

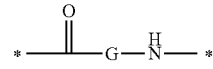

Formula XI'

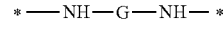

GpA is chosen among the radicals according to formulas VIII

Formula VIII

In which A' is chosen among the radicals according to formulas VIII', VIII" or VIII'''

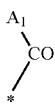
Formula VIII'

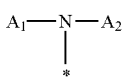
Formula VIII"

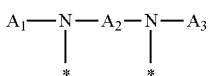
Formula VIII'''

-GpL is chosen among the radicals according to formula XII

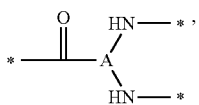
Formula XII

GpC is a radical according to formula IX:

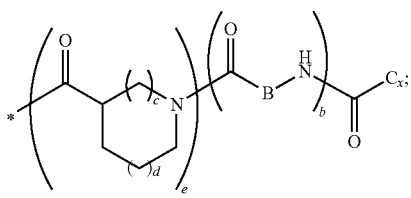
Formula IX

* indicate the attachment sites of the different groups bound by amide functions;

a is an integer equal to 0 or to 1 and a'=1, 2 or 3 if a=1;

a' is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g, h or l is different from 0;

l is an integer equal to 0 or to 1 and l'=1 if l=0 and l'=2 if l=1;

r is an integer equal to 0, 1 or to 2, and s' is an integer equal to 0 or to 1;

And if e is different from 0, then at least one of g, h or l is different from 0;

And if a=0, then l=0;

A, $A_1$, $A_2$ and $A_3$ identical or different, are linear or branched alkyl radicals comprising from 1 to 8 carbon atoms and, optionally, substituted by a radical from a saturated, unsaturated or aromatic ring;

B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms.

$C_x$ is a monovalent, linear or branched, alkyl radical optionally comprising a cyclic part, in which x indicates the number of carbon atoms, and:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC, then $6 \leq x \leq 11$, G is a linear or branched divalent alkyl radical of 1 to 8 carbon atoms, said alkyl radical bearing one or more free carboxylic acid functions.

R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms.

The hydrophobic radicals -Hy according to formula X being bound to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG.

The ratio M between the number of hydrophobic radicals and the number of glutamic or aspartic unites being between $0 < M \leq 0.5$;

When several hydrophobic radicals are borne by a copolyamino acid, then they are identical or different, The degree of polymerization DP in glutamic or aspartic units for the PLG chains is comprised from 5 to 250;

Free carboxylic acids being in the form of an alkaline cation salt chosen from the group consisting of $Na^+$ and $K^+$.

The invention also relates to the precursor Hy' of the hydrophobic radical -Hy according to formula X' as defined below:

Formula X'

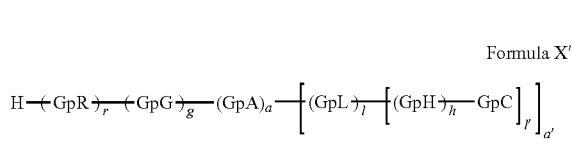

in which

GpR is chosen among the radicals according to formulas VII, VII' or VII'":

Formula VII

 or

Formula VII'

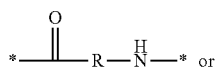 or

Formula VII"

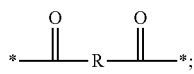;

Identical or different GpG and GpH are chosen among the radicals according to formulas XI or XI';

Formula XI

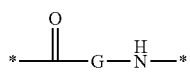

Formula XI'

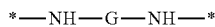

GpA is chosen among the radicals according to formula VIII

Formula VIII

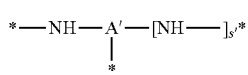

In which A' is chosen among the radicals according to formulas VIII', VIII" or VIII'"

Formula VIII'

Formula VIII"

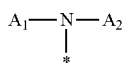

Formula VIII'"

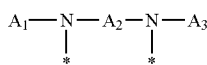

-GpL is chosen among the radicals according to formula XII

Formula XII

,

GpC is a radical according to formula IX:

Formula IX

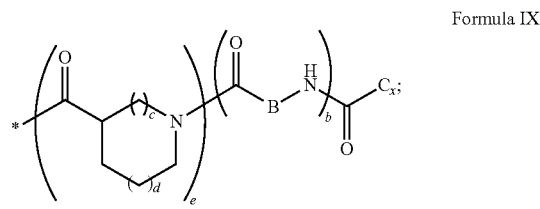

* indicate the attachment sites of the different groups bound by amide functions;
a is an integer equal to 0 or to 1 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g, h or l is different from 0;
l is an integer equal to 0 or to 1 and l'=0 and l'=2 if l=1;
r is an integer equal to 0, 1 or to 2, and
s' is an integer equal to 0 or to 1;
And if e is different from 0, then at least one of g, h or l is different from 0;
And if a=0, then l=0;
A, $A_1$, $A_2$ and $A_3$ identical or different, are linear or branched alkyl radicals comprising from 1 to 8 carbon atoms and, optionally, substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical, optionally comprising an aromatic ring, comprising from 1 to 9 carbon atoms.
$C_x$ is a monovalent, linear or branched, alkyl radical optionally comprising a cyclic part, in which x indicates the number of carbon atoms, and:
When the hydrophobic radical -Hy bears 1 -GpC, then $9 \leq x \leq 25$,
When the hydrophobic radical -Hy bears 2 -GpC, then $9 \leq x \leq 15$,
When the hydrophobic radical -Hy bears 3 -GpC, then $7 \leq x \leq 13$,
When the hydrophobic radical -Hy bears 4 -GpC, then $7 \leq x \leq 11$,
When the hydrophobic radical -Hy bears at least 5 -GpC, then $6 \leq x \leq 11$,
G is a linear or branched divalent alkyl radical of 1 to 8 carbon atoms, said alkyl radical bearing one or more free carboxylic acid functions.
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms.

The hydrophobic radicals -Hy according to formula X being bound to the PLG:
- via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and
- via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG.

The ratio M between the number of hydrophobic radicals and the number of glutamic or aspartic unites being between $0<M\leq0.5$;

When several hydrophobic radicals are borne by a co-polyamino acid, then they are identical or different, Free carboxylic acids being in the form of an alkaline cation salt chosen from the group consisting of $Na^+$ and $K^+$.

Amylin, or islet amyloid polypeptide (IAPP), is a peptide hormone of 37 residues. It is co-secreted with insulin from pancreatic beta cells in a ratio of about 100:1. Amylin plays a role in glycemic regulation by halting the secretion of the endogen glucagon and by slowing down gastric emptying and supporting satiety, thus reducing post-prandial glycemic excursions in blood sugar.

IAPP is taken up using a coding sequence of 89 residues. The amyloid polypeptide Proislet (proIAPP, proamylin, proislet protein) is produced in the pancreatic beta cells in the form of a 67 amino acids deRSO pro-peptide, 7404 Dalton, and undergoes post-translational modifications comprising protease cleavage in order to produce amylin.

In this application, amylin as cited refers to the compounds described in the U.S. Pat. Nos. 5,124,314 and 5,234,906.

By "analogue", when it is used to refer to a peptide or a protein, is meant a peptide or a protein in which one or more amino acid residues constituting the primary sequence have been substituted by other amino acid residues and/or in which one or more constituting amino acid residues have been added. The percentage of homology allowed for this definition of an analogue is 50%. In the case of amylin, an analogue may, for example, be derived from the primary amylin amino acid sequence by substituting one or more natural or non-natural or peptidomimetic acids.

By "derived", when used in reference to a peptide or a protein, is meant a peptide or a protein or an analogue chemically modified by a substitute which is not present in the cited peptide or protein or analogue, that is, a peptide or a protein which was modified by creation of covalent bonds, in order to introduce non-amino acid type substitutes.

An amylin receptor agonist refers to a compound which imitates one or more characteristics of the action of amylin.

Amylin derivatives are described in the article, Yan et al., PNAS, vol. 103, no. 7, p. 2046-2051, 2006.

In one embodiment, the substitute is chosen from the group consisting of fatty chains.

Amylin analogues are described in U.S. Pat. Nos. 5,686,411, 6,114,304 or 6,410,511.

In one embodiment, the composition is characterized in that the amylin, the amylin receptor agonist or amylin analogue is amylin.

In one embodiment, the amylin receptor agonist is amylin.

In one embodiment, the composition is characterized in that the amylin analogue or the amylin receptor agonist is pramlintide (Symlin) marketed by the company ASTRAZENECA AB.

In one embodiment, the co-polyamino acid/amylin molar ratios, amylin receptor agonist or amylin analogue are greater than or equal to 1.

In one embodiment, the co-polyamino acid/amylin molar ratios, amylin receptor agonist or amylin analogue are comprised from 1.5 to 75.

In one embodiment, the co-polyamino acid/amylin molar ratios, amylin receptor agonist or amylin analogue are comprised from 1.8 to 50.

In one embodiment, the co-polyamino acid/amylin molar ratios, amylin receptor agonist or amylin analogue are comprised from 2 to 35.

In one embodiment, the co-polyamino acid/amylin molar ratios, amylin receptor agonist or amylin analogue are comprised from 2.5 to 30.

In one embodiment, the co-polyamino acid/amylin molar ratios, amylin receptor agonist or amylin analogue are comprised from 3 to 30.

In one embodiment, the co-polyamino acid/amylin molar ratios, amylin receptor agonist or amylin analogue are comprised from 3.5 to 30.

In one embodiment, the co-polyamino acid/amylin molar ratios, amylin receptor agonist or amylin analogue are comprised from 4 to 30.

In one embodiment, the co-polyamino acid/amylin molar ratios, amylin receptor agonist or amylin analogue are comprised from 5 to 30.

In one embodiment, the co-polyamino acid/amylin molar ratios, amylin receptor agonist or amylin analogue are comprised from 7 to 30.

In one embodiment, the co-polyamino acid/amylin molar ratios, amylin receptor agonist or amylin analogue are comprised from 9 to 30.

In one embodiment, the co-polyamino acid/amylin molar ratios are comprised from 3 to 75.

In one embodiment, the co-polyamino acid/amylin molar ratios are comprised from 7 to 50.

In one embodiment, the co-polyamino acid/amylin molar ratios are comprised from 10 to 30.

In one embodiment, the co-polyamino acid/amylin molar ratios are comprised from 15 to 30

In one embodiment, the co-polyamino acid/pramlintide molar ratios are comprised from 1.5 to 75.

In one embodiment, the co-polyamino acid/pramlintide molar ratios are comprised from 2 to 50.

In one embodiment, the co-polyamino acid/pramlintide molar ratios are comprised from 3 to 30.

In one embodiment, the co-polyamino acid/pramlintide molar ratios are comprised from 4 to 30.

In one embodiment, the co-polyamino acid/pramlintide molar ratios are comprised from 5 to 30.

In one embodiment, the co-polyamino acid/pramlintide molar ratios are comprised from 8 to 30.

In one embodiment, the co-polyamino acid/pramlintide molar ratios are comprised from 10 to 30.

In one embodiment, the hydrophobic radical Hy/amylin molar ratios, amylin receptor agonist or amylin analogue are comprised from 1.5 to 150.

In one embodiment, the hydrophobic radical Hy/amylin molar ratios, amylin receptor agonist or amylin analogue are comprised from 1.8 to 100.

In one embodiment, the hydrophobic radical Hy/amylin molar ratios, amylin receptor agonist or amylin analogue are comprised from 2 to 70.

In one embodiment, the hydrophobic radical Hy/amylin molar ratios, amylin receptor agonist or amylin analogue are comprised from 2.5 to 60.

In one embodiment, the hydrophobic radical Hy/amylin molar ratios, amylin receptor agonist or amylin analogue are comprised from 3 to 60.

In one embodiment, the hydrophobic radical Hy/amylin molar ratios, amylin receptor agonist or amylin analogue are comprised from 3.5 to 60.

In one embodiment, the hydrophobic radical Hy/amylin molar ratios, amylin receptor agonist or amylin analogue are comprised from 4 to 60.

In one embodiment, the hydrophobic radical Hy/amylin molar ratios, amylin receptor agonist or amylin analogue are comprised from 5 to 60.

In one embodiment, the hydrophobic radical Hy/amylin molar ratios, amylin receptor agonist or amylin analogue are comprised from 7 to 60.

In one embodiment, the hydrophobic radical Hy/amylin molar ratios, amylin receptor agonist or amylin analogue are comprised from 9 to 60.

In one embodiment, the hydrophobic radical Hy/amylin molar ratios are comprised from 5 to 60.

In one embodiment, the hydrophobic radical Hy/amylin molar ratios are comprised from 10 to 60.

In one embodiment, the hydrophobic radical Hy/amylin molar ratios are comprised from are comprised from 15 to 60.

In one embodiment, the hydrophobic radical Hy/pramlintide molar ratios are comprised from are comprised from 1.5 to 60.

In one embodiment, the hydrophobic radical Hy/pramlintide molar ratios are comprised from are comprised from 2 to 60.

In one embodiment, the hydrophobic radical Hy/pramlintide molar ratios are comprised from 3 to 60.

In one embodiment, the hydrophobic radical Hy/pramlintide molar ratios are comprised from 4 to 60.

In one embodiment, the hydrophobic radical Hy/pramlintide molar ratios are comprised from 5 to 60.

In one embodiment, the hydrophobic radical Hy/pramlintide molar ratios are comprised from 8 to 60.

In one embodiment, the hydrophobic radical Hy/pramlintide molar ratios are comprised from 10 to 60.

In one embodiment, the co-polyamino acid/amylin mass ratios, amylin receptor agonist or amylin analogue are comprised from 1.0 to 70.

In one embodiment, the co-polyamino acid/amylin mass ratios, amylin receptor agonist or amylin analogue are comprised from 1.2 to 45.

In one embodiment, the co-polyamino acid/amylin mass ratios, amylin receptor agonist or amylin analogue are comprised from 1.3 to 30.

In one embodiment, the co-polyamino acid/amylin mass ratios, amylin receptor agonist or amylin analogue are comprised from 1.7 to 27.

In one embodiment, the co-polyamino acid/amylin mass ratios, amylin receptor agonist or amylin analogue are comprised from 2.0 to 27.

In one embodiment, the co-polyamino acid/amylin mass ratios, amylin receptor agonist or amylin analogue are comprised from 2.3 to 27.

In one embodiment, the co-polyamino acid/amylin mass ratios, amylin receptor agonist or amylin analogue are comprised from 2.7 to 27.

In one embodiment, the co-polyamino acid/amylin mass ratios, amylin receptor agonist or amylin analogue are comprised from 3.3 to 27.

In one embodiment, the co-polyamino acid/amylin mass ratios, amylin receptor agonist or amylin analogue are comprised from 4.7 to 27.

In one embodiment, the co-polyamino acid/amylin mass ratios, amylin receptor agonist or amylin analogue are comprised from 6.0 to 27.

In one embodiment, the co-polyamino acid/amylin mass ratios are comprised from 2.0 to 67.

In one embodiment, the co-polyamino acid/amylin mass ratios are comprised from 4.7 to 27.

In one embodiment, the co-polyamino acid/amylin mass ratios are comprised from 6.7 to 27.

In one embodiment, the co-polyamino acid/amylin mass ratios are comprised from 10 to 27.

In one embodiment, the co-polyamino acid/pramlintide mass ratios are comprised from 1.0 to 67.

In one embodiment, the co-polyamino acid/pramlintide mass ratios are comprised from 1.3 to 45.

In one embodiment, the co-polyamino acid/pramlintide mass ratios are comprised from 2.7 to 27.

In one embodiment, the co-polyamino acid/pramlintide mass ratios are comprised from 3.3 to 27.

In one embodiment, the co-polyamino acid/pramlintide mass ratios are comprised from 5.3 to 27.

In one embodiment, the co-polyamino acid/pramlintide mass ratios are comprised from 6.7 to 27.

In one embodiment, the composition is characterized in that it also comprises insulin.

In one embodiment, the composition is characterized in that the insulin is a prandial insulin. Prandial insulins are soluble at pH 7.

Prandial insulin designates a so-called rapid or "regular" insulin.

So-called rapid prandial insulins are insulins which must meet the needs triggered by the ingestion of proteins and glucides during a meal; they must act in less than 30 minutes.

In one embodiment, the so-called "regular" prandial insulin is human insulin.

In one embodiment, the prandial insulin is recombinant human insulin as described in European and American pharmacopoeias.

Human insulin is, for example, marketed under the brands Humulin® (ELI LILLY) and Novolin® (NOVO NORDISK).

So-called rapid (fast acting) prandial insulins are insulins that are obtained by recombination and for which the primary sequence has been modified to reduce their duration of action.

In one embodiment, the so-called fast acting prandial insulins are chosen from the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

The insulins recommended by the pharmacopoeias for the insulins are presented in the table below with their corresponding amounts in mg:

| Insulin | Pharmacopoeia EP 8.0 (2014) | Pharmacopoeia US - USP38 (2015) |
|---|---|---|
| Aspart | 1 U = 0.0350 mg insulin aspart | 1 USP = 0.0350 mg insulin aspart |
| Lispro | 1 U = 0.0347 mg insulin lispro | 1 USP = 0.0347 mg insulin lispro |
| Human | 1 UI = 0.0347 mg human insulin | 1 USP = 0.0347 mg human insulin |

In the case of insulin glulisine, 100U=3.49 mg of insulin glulisine (according to "Annex 1—Summary of product characteristics" relative to ADIPRA®).

Nevertheless, in the rest of the text, U is systematically used indifferently for the quantities and concentrations of all insulins. The respective, corresponding values in mg are those given above for values expressed in U, UI or USP.

In one embodiment, it relates to a pharmaceutical formulation characterized in that the concentration of insulin is comprised from 240 to 3000 µM (40 to 500 U/mL).

In one embodiment, it relates to a pharmaceutical formulation characterized in that the concentration of insulin is comprised from 600 to 3000 µM (100 to 500 U/mL).

In one embodiment, it relates to a pharmaceutical formulation characterized in that the concentration of insulin is comprised from 600 to 2400 µM (100 to 400 U/mL).

In one embodiment, it relates to a pharmaceutical formulation characterized in that the concentration of insulin is comprised from 600 to 1800 µM (100 to 300 U/mL).

In one embodiment, it relates to a pharmaceutical formulation characterized in that the concentration of insulin is comprised from 600 to 1200 µM (100 to 200 U/mL).

In one embodiment, it relates to a pharmaceutical formulation characterized in that the concentration of insulin is 600 µM (100 U/mL).

In one embodiment, it relates to a pharmaceutical formulation characterized in that the concentration of insulin is 1200 µM (200 U/mL).

In one embodiment, it relates to a pharmaceutical formulation characterized in that the concentration of insulin is 1800 µM (300 U/mL).

In one embodiment, it relates to a pharmaceutical formulation characterized in that the concentration of insulin is 2400 µM (400 U/mL).

In one embodiment, it relates to a pharmaceutical formulation characterized in that the concentration of insulin is 3000 µM (500 U/mL).

In one embodiment, the co-polyamino acid/amylin molar ratio, amylin receptor agonist or amylin analogue is greater than or equal to 1.

In one embodiment, comprising prandial insulin, the co-polyamino acid/amylin molar ratios, amylin receptor agonist or amylin analogue are comprised from 1.5 to 75.

In one embodiment, comprising prandial insulin, the co-polyamino acid/amylin molar ratios, amylin receptor agonist or amylin analogue are comprised from 1.8 to 50.

In one embodiment, comprising prandial insulin, the co-polyamino acid/amylin molar ratios, amylin receptor agonist or amylin analogue are comprised from 2 to 35.

In one embodiment, comprising prandial insulin, the co-polyamino acid/amylin molar ratios, amylin receptor agonist or amylin analogue are comprised from 2.5 to 30.

In one embodiment, comprising prandial insulin, the co-polyamino acid/amylin molar ratios, amylin receptor agonist or amylin analogue are comprised from 3 to 30.

In one embodiment, comprising prandial insulin, the co-polyamino acid/amylin molar ratios, amylin receptor agonist or amylin analogue are comprised from 3.5 to 30.

In one embodiment, comprising prandial insulin, the co-polyamino acid/amylin molar ratios, amylin receptor agonist or amylin analogue are comprised from 4 to 30.

In one embodiment, comprising prandial insulin, the co-polyamino acid/amylin molar ratios, amylin receptor agonist or amylin analogue are comprised from 5 to 30.

In one embodiment, comprising prandial insulin, the co-polyamino acid/amylin molar ratios, amylin receptor agonist or amylin analogue are comprised from 7 to 30.

In one embodiment, comprising prandial insulin, the co-polyamino acid/amylin molar ratios, amylin receptor agonist or amylin analogue are comprised from 9 to 30.

In one embodiment, comprising prandial insulin, the co-polyamino acid/amylin molar ratios are comprised from 5 to 75.

In one embodiment, comprising prandial insulin, the co-polyamino acid/amylin molar ratios are comprised from 10 to 50.

In one embodiment, comprising prandial insulin, the co-polyamino acid/amylin molar ratios are comprised from 15 to 30.

In one embodiment, the co-polyamino acid/pramlintide molar ratio is greater than or equal to 1.

In one embodiment, comprising prandial insulin, the co-polyamino acid/pramlintide molar ratios are comprised from 1.5 to 75.

In one embodiment, comprising prandial insulin, the co-polyamino acid/pramlintide molar ratios are comprised from 2 to 50.

In one embodiment, comprising prandial insulin, the co-polyamino acid/pramlintide molar ratios are comprised from 3 to 30.

In one embodiment, comprising prandial insulin, the co-polyamino acid/pramlintide molar ratios are comprised from 4 to 30.

In one embodiment, comprising prandial insulin, the co-polyamino acid/pramlintide molar ratios are comprised from 5 to 30.

In one embodiment, comprising prandial insulin, the co-polyamino acid/pramlintide molar ratios are comprised from 8 to 30.

In one embodiment, comprising prandial insulin, the co-polyamino acid/pramlintide molar ratios are comprised from 10 to 30.

In one embodiment, comprising prandial insulin, the hydrophobic radical Hy/amylin, amylin receptor agonist or amylin analogue molar ratios are comprised from 1.5 to 150.

In one embodiment, comprising prandial insulin, the hydrophobic radical Hy/amylin, amylin receptor agonist or amylin analogue molar ratios are comprised from 1.8 to 100.

In one embodiment, comprising prandial insulin, the hydrophobic radical Hy/amylin, amylin receptor agonist or amylin analogue molar ratios are comprised from 2 to 70.

In one embodiment, comprising prandial insulin, the hydrophobic radical Hy/amylin, amylin receptor agonist or amylin analogue molar ratios are comprised from 2.5 to 60.

In one embodiment, comprising prandial insulin, the hydrophobic radical Hy/amylin, amylin receptor agonist or amylin analogue molar ratios are comprised from 3 to 60.

In one embodiment, comprising prandial insulin, the hydrophobic radical Hy/amylin, amylin receptor agonist or amylin analogue molar ratios are comprised from 3.5 to 60.

In one embodiment, comprising prandial insulin, the hydrophobic radical Hy/amylin, amylin receptor agonist or amylin analogue molar ratios are comprised from 4 to 60.

In one embodiment, comprising prandial insulin, the hydrophobic radical Hy/amylin, amylin receptor agonist or amylin analogue molar ratios are comprised from 5 to 60.

In one embodiment, comprising prandial insulin, the hydrophobic radical Hy/amylin, amylin receptor agonist or amylin analogue molar ratios are comprised from 7 to 60.

In one embodiment, comprising prandial insulin, the hydrophobic radical Hy/amylin, amylin receptor agonist or amylin analogue molar ratios are comprised from 9 to 60.

In one embodiment, comprising prandial insulin, the hydrophobic radical Hy/amylin molar ratios are comprised from 5 to 60.

In one embodiment, comprising prandial insulin, the hydrophobic radical Hy/amylin molar ratios are comprised from 10 to 60.

In one embodiment, comprising prandial insulin, the hydrophobic radical Hy/amylin molar ratios are comprised from 15 to 60.

In one embodiment, comprising prandial insulin, the hydrophobic radical Hy/pramlintide molar ratios are comprised from 1.5 to 60.

In one embodiment, comprising prandial insulin, the hydrophobic radical Hy/pramlintide molar ratios are comprised from 2 to 60.

In one embodiment, comprising prandial insulin, the hydrophobic radical Hy/pramlintide molar ratios are comprised from 3 to 60.

In one embodiment, comprising prandial insulin, the hydrophobic radical Hy/pramlintide molar ratios are comprised from 4 to 60.

In one embodiment, comprising prandial insulin, the hydrophobic radical Hy/pramlintide molar ratios are comprised from 5 to 60.

In one embodiment, comprising prandial insulin, the hydrophobic radical Hy/pramlintide molar ratios are comprised from 8 to 60.

In one embodiment, comprising prandial insulin, the hydrophobic radical Hy/pramlintide molar ratios are comprised from 10 and 60.

In one embodiment, comprising prandial insulin, the co-polyamino acid/amylin, amylin receptor agonist or amylin analogue mass ratios are comprised from 1.0 to 70.

In one embodiment, comprising prandial insulin, the co-polyamino acid/amylin, amylin receptor agonist or amylin analogue mass ratios are comprised from 1.2 to 45.

In one embodiment, comprising prandial insulin, the co-polyamino acid/amylin, amylin receptor agonist or amylin analogue mass ratios are comprised from 1.3 to 30.

In one embodiment, comprising prandial insulin, the co-polyamino acid/amylin, amylin receptor agonist or amylin analogue mass ratios are comprised from 1.7 to 27.

In one embodiment, comprising prandial insulin, the co-polyamino acid/amylin, amylin receptor agonist or amylin analogue mass ratios are comprised from 2.0 to 27.

In one embodiment, comprising prandial insulin, the co-polyamino acid/amylin, amylin receptor agonist or amylin analogue mass ratios are comprised from 2.3 to 27.

In one embodiment, comprising prandial insulin, the co-polyamino acid/amylin, amylin receptor agonist or amylin analogue mass ratios are comprised from 2.7 to 27.

In one embodiment, comprising prandial insulin, the co-polyamino acid/amylin, amylin receptor agonist or amylin analogue mass ratios are comprised from 3.3 to 27.

In one embodiment, comprising prandial insulin, the co-polyamino acid/amylin, amylin receptor agonist or amylin analogue mass ratios are comprised from 4.7 to 27.

In one embodiment, comprising prandial insulin, the co-polyamino acid/amylin, amylin receptor agonist or amylin analogue mass ratios are comprised from 6.0 to 27.

In one embodiment, comprising prandial insulin, the co-polyamino acid/amylin mass ratios are comprised from 3.3 to 67.

In one embodiment, comprising prandial insulin, the co-polyamino acid/amylin mass ratios are comprised from 6.6 to 27.

In one embodiment, comprising prandial insulin, the co-polyamino acid/amylin mass ratios are comprised from 10 to 27.

In one embodiment, comprising prandial insulin, the co-polyamino acid/pramlintide mass ratios are comprised from 1.0 to 67.

In one embodiment, comprising prandial insulin, the co-polyamino acid/pramlintide mass ratios are comprised from 1.2 to 45.

In one embodiment, comprising prandial insulin, the co-polyamino acid/pramlintide mass ratios are comprised from 1.3 to 27.

In one embodiment, comprising prandial insulin, the co-polyamino acid/pramlintide mass ratios are comprised from 1.7 to 27.

In one embodiment, comprising prandial insulin, the co-polyamino acid/pramlintide mass ratios are comprised from 2.0 to 27.

In one embodiment, comprising prandial insulin, the co-polyamino acid/pramlintide mass ratios are comprised from 2.3 to 27.

In one embodiment, comprising prandial insulin, the co-polyamino acid/pramlintide mass ratios are comprised from 2.7 to 27.

In one embodiment, comprising prandial insulin, the co-polyamino acid/pramlintide mass ratios are comprised from 3.3 to 27.

In one embodiment, comprising prandial insulin, the co-polyamino acid/pramlintide mass ratios are comprised from 4.7 to 27.

In one embodiment, comprising prandial insulin, the co-polyamino acid/pramlintide mass ratios are comprised from 6.0 to 27.

Furthermore, it is particularly advantageous to combine amylin, an amylin receptor agonist or an amylin analogue, in combination or not with a prandial insulin, with GLP-1, GLP-1 analogues, GLP-1 receptor agonists, which are commonly called GLP-1 RA. This specifically makes it possible to potentiate the effect of insulin and is recommended in certain types of diabetes treatment.

In one embodiment, the GLP-1, GLP-1 analogues or GLP-1 RA are called "fast acting". By "fast acting" is meant GLP-1s, GLP-1 analogues or GLP-1RAs for which the apparent elimination half-life after subcutaneous injection in humans is less than 8 hours, in particular, less than 5 hours, preferentially less than 4 hours, or even less than 3 hours, such as, for example, exenatide and lixisenatide.

In one embodiment, GLP-1s, GLP-1 analogues or GLP-1RAs are chosen from the group consisting of exenatide or Byetta® (ASTRA-ZENECA), lixisenatide or Lyxumia® (SANOFI), their analogues or derivatives and their pharmaceutically acceptable salts.

In one embodiment, the GLP-1, GLP-1 analogue or GLP-1RA is exenatide or Byetta®, their analogues or derivatives and their pharmaceutically acceptable salts.

In one embodiment, the GLP-1, GLP-1 analogue or GLP-1RA is lixisenatide or Lyxumia®, their analogues or derivatives and their pharmaceutically acceptable salts.

In one embodiment, the concentration of exenatide, its analogues or derivatives and their pharmaceutically acceptable salts are comprised within an interval from 0.01 to 1.0 mg per 100 U of insulin.

In one embodiment, the concentration of exenatide, its analogues or derivatives and their pharmaceutically acceptable salts is from 0.01 to 0.5 mg per 100 U of insulin.

In one embodiment, the concentration of exenatide, its analogues or derivatives and their pharmaceutically acceptable salts is from 0.02 to 0.4 mg per 100 U of insulin.

In one embodiment, the concentration of exenatide, its analogues or derivatives and their pharmaceutically acceptable salts is from 0.03 to 0.3 mg per 100 U of insulin.

In one embodiment, the concentration of exenatide, its analogues or derivatives and their pharmaceutically acceptable salts is from 0.04 to 0.2 mg per 100 U of insulin.

In one embodiment, the concentration of exenatide, its analogues or derivatives and their pharmaceutically acceptable salts is from 0.04 to 0.15 mg per 100 U of insulin.

In one embodiment, the concentration of lixisenatide, its analogues or derivatives and their pharmaceutically acceptable salts are comprised from within an interval from 0.01 to 1 mg per 100 U of insulin.

In one embodiment, the concentration of lixisenatide, its analogues or derivatives and their pharmaceutically acceptable salts is from 0.01 to 0.5 mg per 100 U of insulin.

In one embodiment, the concentration of lixisenatide, its analogues or derivatives and their pharmaceutically acceptable salts is from 0.02 to 0.4 mg per 100 U of insulin.

In one embodiment, the concentration of lixisenatide, its analogues or derivatives and their pharmaceutically acceptable salts is from 0.03 to 0.3 mg per 100 U of insulin.

In one embodiment, the concentration of lixisenatide, its analogues or derivatives and their pharmaceutically acceptable salts is from 0.04 to 0.2 mg per 100 U of insulin.

In one embodiment, the concentration of lixisenatide, its analogues or derivatives and their pharmaceutically acceptable salts is from 0.04 to 0.15 mg per 100 U of insulin.

In one embodiment, the compositions according to the invention are executed by mixing solutions of amylin and commercial solutions of GLP-1, GLP-1 analogue or GLP-1 RA receptors agonist in volume ratios included in an interval from 10/90 to 90/10, in the presence of a co-polyamino acid.

In one embodiment, the composition according to the invention is free of a prandial insulin.

In one embodiment, the composition according to the invention does not comprise GLP-1, a GLP-1 analogue or GLP-1 receptors agonist, currently called GLP-1 RA.

The invention also relates to compositions which also comprise ionic species, said ionic species making it possible to improve the stability of the compositions.

The invention also relates to the use of ionic species chosen from the group of anions, cations and/or zwitterions to improve the physical-chemical stability of the compositions.

In one embodiment, the ionic species comprise more than 10 carbon atoms.

Said ionic species are chosen from the group of anions, cations and/or zwitterions. By zwitterion is meant a species bearing at least one positive charge and at least one negative charge on two non-adjacent atoms.

Said ionic species are used alone or in mixture and preferably in mixture.

In one embodiment, the anions are chosen among organic anions.

In one embodiment, the organic anions comprise less than 10 carbon atoms.

In one embodiment, the organic anions are chosen from the group consisting of acetate, citrate and succinate.

In one embodiment, the anions are chosen among anions of mineral origin.

In one embodiment, the anions of mineral origin are chosen from the group consisting of sulfates, phosphates and halides, specifically the chlorides.

In one embodiment, the cations are chosen among organic cations.

In one embodiment, the organic cations comprise less than 10 carbon atoms.

In one embodiment, the organic cations are chosen from the group consisting of ammoniums, for example, 2-Amino-2-(hydroxymethyl)propane-1,3-diol, where the amine is in ammonium form.

In one embodiment, the cations are chosen among cations of mineral origin.

In one embodiment, the cations of mineral origin are chosen from the group consisting of zinc, in particular $Zn^{2+}$ and the alkaline metals, in particular $Na^+$ et $K^+$.

In one embodiment, the zwitterions are chosen among zwitterions of organic origin.

In one embodiment, the zwitterions are chosen among the amino acids.

In one embodiment, the amino acids are chosen among the alphatic amino acids in the group consisting of glycine, alanine, valine, isoleucine and leucine.

In one embodiment, the amino acids are chosen among the cyclic amino acids in the group consisting of proline.

In one embodiment, the amino acids are chosen among the hydroxyl or sulfur amino acids in the group consisting of cysteine, serine, threonine and methionine.

In one embodiment, the amino acids are chosen among the aromatic amino acids in the group consisting of phenylaline, tyrosine and tryptophane.

In one embodiment, the amino acids are chosen among the amino acids for which the carboxyl function of the lateral chain is amidified in the group consisting of asparagine and glutamine.

In one embodiment, the zwitterions of organic origin are chosen from the group consisting of amino acids with an un-charged lateral chain.

In one embodiment, the zwitterions of organic origin are chosen from the group consisting of the diacids or acidic amino acids.

In one embodiment, the amino acids are chosen from the group consisting of glutamic acid and aspartic acid, optionally in the form of salts.

In one embodiment, the zwitterions of organic origin are chosen from the group consisting of basic amino acids, or so-called cationic amino acids.

In one embodiment, the so-called "cationic" amino acids are chosen among arginine, histidine and lysine, in particular arginine and lysine.

Very particularly, the zwitterions comprising as many negative charges as positive charges and therefore, an overall nil charge at the isoelectric point and/or at a pH from 6.0 to 8.0.

Said ionic species are introduced into the compositions in the form of salts. The introduction of these may be done in solid form before putting them into solution in the compositions, or in the form of solution, in particular, of concentrated solution.

For example, cations of mineral origin are added in the form of salts chosen among sodium chloride, zinc chloride, sodium phosphate, sodium sulfate, etc.

For example, anions of organic origin are added in the form of salts chosen among sodium citrate or sodium potassium or sodium acetate.

For example, amino acids are added in the form of salts chosen among arginine hydrochloride, histidine hydrochloride or in non-salt form such as, for example, histidine or arginine.

In one embodiment, the total molar concentration of ionic species in the composition is greater than or equal to 10 mM.

In one embodiment, the total molar concentration of ionic species in the composition is greater than or equal to 20 mM.

In one embodiment, the total molar concentration of ionic species in the composition is greater than or equal to 30 mM.

In one embodiment, the total molar concentration of ionic species in the composition is greater than or equal to 50 mM.

In one embodiment, the total molar concentration of ionic species in the composition is greater than or equal to 75 mM.

In one embodiment, the total molar concentration of ionic species in the composition is greater than or equal to 100 mM.

In one embodiment, the total molar concentration of ionic species in the composition is greater than or equal to 200 mM.

In one embodiment, the total molar concentration of ionic species in the composition is greater than or equal to 300 mM.

In one embodiment, the total molar concentration of ionic species in the composition is greater than or equal to 500 mM.

In one embodiment, the total molar concentration of ionic species in the composition is greater than or equal to 600 mM.

In one embodiment, the total molar concentration of ionic species in the composition is greater than or equal to 700 mM.

In one embodiment, the total molar concentration of ionic species in the composition is greater than or equal to 800 mM.

In one embodiment, the total molar concentration of ionic species in the composition is greater than or equal to 900 mM.

In one embodiment, the total molar concentration of ionic species in the composition is less than or equal to 1000 mM.

In one embodiment, the total molar concentration of ionic species in the composition is less than or equal to 1500 mM.

In one embodiment, the total molar concentration of ionic species in the composition is less than or equal to 1200 mM.

In one embodiment, the total molar concentration of ionic species in the composition is less than or equal to 1000 mM.

In one embodiment, the total molar concentration of ionic species in the composition is less than or equal to 900 mM.

In one embodiment, the total molar concentration of ionic species in the composition is less than or equal to 800 mM.

In one embodiment, the total molar concentration of ionic species in the composition is less than or equal to 700 mM.

In one embodiment, the total molar concentration of ionic species in the composition is less than or equal to 600 mM.

In one embodiment, the total molar concentration of ionic species in the composition is less than or equal to 500 mM.

In one embodiment, the total molar concentration of ionic species in the composition is less than or equal to 400 mM.

In one embodiment, the total molar concentration of ionic species in the composition is less than or equal to 300 mM.

In one embodiment, the total molar concentration of ionic species in the composition is less than or equal to 200 mM.

In one embodiment, the total molar concentration of ionic species in the composition is less than or equal to 100 mM.

In one embodiment, the total molar concentration of ionic species in the composition is comprised from 10 to 1000 mM.

In one embodiment, the total molar concentration of ionic species in the composition is comprised from 20 to 1000 mM.

In one embodiment, the total molar concentration of ionic species in the composition is comprised from 30 to 1000 mM.

In one embodiment, the total molar concentration of ionic species in the composition is comprised from 50 to 1000 mM.

In one embodiment, the total molar concentration of ionic species in the composition is comprised from 75 to 1000 mM.

In one embodiment, the total molar concentration of ionic species in the composition is comprised from 100 to 1000 mM.

In one embodiment, the total molar concentration of ionic species in the composition is comprised from 200 to 1000 mM.

In one embodiment, the total molar concentration of ionic species in the composition is comprised from 300 to 1000 mM.

In one embodiment, the total molar concentration of ionic species in the composition is comprised from 400 to 1000 mM.

In one embodiment, the total molar concentration of ionic species in the composition is comprised from 500 to 1000 mM.

In one embodiment, the total molar concentration of ionic species in the composition is comprised from 600 to 1000 mM.

In one embodiment, the total molar concentration of ionic species in the composition is comprised from 10 to 900 mM.

In one embodiment, the total molar concentration of ionic species in the composition is comprised from 20 to 900 mM.

In one embodiment, the total molar concentration of ionic species in the composition is comprised from 30 to 900 mM.

In one embodiment, the total molar concentration of ionic species in the composition is comprised from 50 to 900 mM.

In one embodiment, the total molar concentration of ionic species in the composition is comprised from 75 to 900 mM.

In one embodiment, the total molar concentration of ionic species in the composition is comprised from 100 to 900 mM.

In one embodiment, the total molar concentration of ionic species in the composition is comprised from 200 to 900 mM.

In one embodiment, the total molar concentration of ionic species in the composition is comprised from 300 to 900 mM.

In one embodiment, the total molar concentration of ionic species in the composition is comprised from 400 to 900 mM.

In one embodiment, the total molar concentration of ionic species in the composition is comprised from 500 to 900 mM.

In one embodiment, the total molar concentration of ionic species in the composition is comprised from 600 to 900 mM.

In one embodiment, the total molar concentration of ionic species in the composition is comprised from 10 to 800 mM.

In one embodiment, the total molar concentration of ionic species in the composition is comprised from 20 to 800 mM.

In one embodiment, the total molar concentration of ionic species in the composition is comprised from 30 to 800 mM.

In one embodiment, the total molar concentration of ionic species in the composition is comprised from 50 to 800 mM.

In one embodiment, the total molar concentration of ionic species in the composition is comprised from 75 to 800 mM.

In one embodiment, the total molar concentration of ionic species in the composition is comprised from 100 to 800 mM.

In one embodiment, the total molar concentration of ionic species in the composition is comprised from 200 to 800 mM.

In one embodiment, the total molar concentration of ionic species in the composition is comprised from 300 to 800 mM.

In one embodiment, the total molar concentration of ionic species in the composition is comprised from 400 to 800 mM.

In one embodiment, the total molar concentration of ionic species in the composition is comprised from 500 to 800 mM.

In one embodiment, the total molar concentration of ionic species in the composition is comprised from 600 to 800 mM.

In one embodiment, the total molar concentration of ionic species in the composition is comprised from 10 to 700 mM.

In one embodiment, the total molar concentration of ionic species in the composition is comprised from 20 to 700 mM.

In one embodiment, the total molar concentration of ionic species in the composition is comprised from 30 to 700 mM.

In one embodiment, the total molar concentration of ionic species in the composition is comprised from 50 to 700 mM.

In one embodiment, the total molar concentration of ionic species in the composition is comprised from 75 to 700 mM.

In one embodiment, the total molar concentration of ionic species in the composition is comprised from 100 to 700 mM.

In one embodiment, the total molar concentration of ionic species in the composition is comprised from 200 to 700 mM.

In one embodiment, the total molar concentration of ionic species in the composition is comprised from 300 to 700 mM.

In one embodiment, the total molar concentration of ionic species in the composition is comprised from 400 to 700 mM.

In one embodiment, the total molar concentration of ionic species in the composition is comprised from 500 to 700 mM.

In one embodiment, the total molar concentration of ionic species in the composition is comprised from 600 to 700 mM.

In one embodiment, the total molar concentration of ionic species in the composition is comprised from 10 to 600 mM.

In one embodiment, the total molar concentration of ionic species in the composition is comprised from 20 to 600 mM.

In one embodiment, the total molar concentration of ionic species in the composition is comprised from 30 to 600 mM.

In one embodiment, the total molar concentration of ionic species in the composition is comprised from 50 to 600 mM.

In one embodiment, the total molar concentration of ionic species in the composition is comprised from 75 to 600 mM.

In one embodiment, the total molar concentration of ionic species in the composition is comprised from 100 to 600 mM.

In one embodiment, the total molar concentration of ionic species in the composition is comprised from 200 to 600 mM.

In one embodiment, the total molar concentration of ionic species in the composition is comprised from 300 to 600 mM.

In one embodiment, the total molar concentration of ionic species in the composition is comprised from 400 to 600 mM.

In one embodiment, the total molar concentration of ionic species in the composition is comprised from 500 to 600 mM.

In one embodiment, the total molar concentration of ionic species in the composition is comprised from 10 to 500 mM.

In one embodiment, the total molar concentration of ionic species in the composition is comprised from 20 to 500 mM.

In one embodiment, the total molar concentration of ionic species in the composition is comprised from 30 to 500 mM.

In one embodiment, the total molar concentration of ionic species in the composition is comprised from 50 to 500 mM.

In one embodiment, the total molar concentration of ionic species in the composition is comprised from 75 to 500 mM.

In one embodiment, the total molar concentration of ionic species in the composition is comprised from 100 to 500 mM.

In one embodiment, the total molar concentration of ionic species in the composition is comprised from 200 to 500 mM.

In one embodiment, the total molar concentration of ionic species in the composition is comprised from 300 to 500 mM.

In one embodiment, the total molar concentration of ionic species in the composition is comprised from 400 to 500 mM.

In one embodiment, the total molar concentration of ionic species in the composition is comprised from 10 to 400 mM.

In one embodiment, the total molar concentration of ionic species in the composition is comprised from 20 to 400 mM.

In one embodiment, the total molar concentration of ionic species in the composition is comprised from 30 to 400 mM.

In one embodiment, the total molar concentration of ionic species in the composition is comprised from 50 to 400 mM.

In one embodiment, the total molar concentration of ionic species in the composition is comprised from 75 to 400 mM.

In one embodiment, the total molar concentration of ionic species in the composition is comprised from 100 to 400 mM.

In one embodiment, the total molar concentration of ionic species in the composition is comprised from 200 to 400 mM.

In one embodiment, the total molar concentration of ionic species in the composition is comprised from 300 to 400 mM.

In one embodiment, the total molar concentration of ionic species in the composition is comprised from 10 to 300 mM.

In one embodiment, the total molar concentration of ionic species in the composition is comprised from 20 to 300 mM.

In one embodiment, the total molar concentration of ionic species in the composition is comprised from 30 to 300 mM.

In one embodiment, the total molar concentration of ionic species in the composition is comprised from 50 to 300 mM.

In one embodiment, the total molar concentration of ionic species in the composition is comprised from 75 to 300 mM.

In one embodiment, the total molar concentration of ionic species in the composition is comprised from 100 to 300 mM.

In one embodiment, the total molar concentration of ionic species in the composition is comprised from 200 to 300 mM.

In one embodiment, the total molar concentration of ionic species in the composition is comprised from 10 to 200 mM.

In one embodiment, the total molar concentration of ionic species in the composition is comprised from 20 to 200 mM.

In one embodiment, the total molar concentration of ionic species in the composition is comprised from 30 to 200 mM.

In one embodiment, the total molar concentration of ionic species in the composition is comprised from 50 to 200 mM.

In one embodiment, the total molar concentration of ionic species in the composition is comprised from 75 to 200 mM.

In one embodiment, the total molar concentration of ionic species in the composition is comprised from 100 to 200 mM.

In one embodiment, the total molar concentration of ionic species in the composition is comprised from 10 to 100 mM.

In one embodiment, the total molar concentration of ionic species in the composition is comprised from 20 to 100 mM.

In one embodiment, the total molar concentration of ionic species in the composition is comprised from 30 to 100 mM.

In one embodiment, the total molar concentration of ionic species in the composition is comprised from 50 to 100 mM.

In one embodiment, the total molar concentration of ionic species in the composition is comprised from 75 to 100 mM.

In one embodiment, the total molar concentration of ionic species in the composition is comprised from 10 to 75 mM.

In one embodiment, the total molar concentration of ionic species in the composition is comprised from 20 to 75 mM.

In one embodiment, the total molar concentration of ionic species in the composition is comprised from 30 to 75 mM.

In one embodiment, the total molar concentration of ionic species in the composition is comprised from 50 to 75 mM.

In one embodiment, the total molar concentration of ionic species in the composition is comprised from 10 to 50 mM.

In one embodiment, the total molar concentration of ionic species in the composition is comprised from 20 to 50 mM.

In one embodiment, the total molar concentration of ionic species in the composition is comprised from 30 to 50 mM.

In one embodiment, said ionic species are present in a concentration from 5 to 400 mM.

In one embodiment, said ionic species are present in a concentration from 5 to 300 mM.

In one embodiment, said ionic species are present in a concentration from 5 to 200 mM.

In one embodiment, said ionic species are present in a concentration from 5 to 100 mM.

In one embodiment, said ionic species are present in a concentration from 5 to 75 mM.

In one embodiment, said ionic species are present in a concentration from 5 to 50 mM.

In one embodiment, said ionic species are present in a concentration from 5 to 25 mM.

In one embodiment, said ionic species are present in a concentration from 5 to 20 mM.

In one embodiment, said ionic species are present in a concentration from 5 to 10 mM.

In one embodiment, said ionic species are present in a concentration from 10 to 400 mM.

In one embodiment, said ionic species are present in a concentration from 10 to 300 mM.

In one embodiment, said ionic species are present in a concentration from 10 to 200 mM.

In one embodiment, said ionic species are present in a concentration from 10 to 100 mM.

In one embodiment, said ionic species are present in a concentration from 10 to 75 mM.

In one embodiment, said ionic species are present in a concentration from 10 to 50 mM.

In one embodiment, said ionic species are present in a concentration from 10 to 25 mM.

In one embodiment, said ionic species are present in a concentration from 10 to 20 mM.

In one embodiment, said ionic species are present in a concentration from 20 to 300 mM.

In one embodiment, said ionic species are present in a concentration from 20 to 200 mM.

In one embodiment, said ionic species are present in a concentration from 20 to 100 mM.

In one embodiment, said ionic species are present in a concentration from 20 to 75 mM.

In one embodiment, said ionic species are present in a concentration from 20 to 50 mM.

In one embodiment, said ionic species are present in a concentration from 20 to 25 mM.

In one embodiment, said ionic species are present in a concentration from 50 to 300 mM.

In one embodiment, said ionic species are present in a concentration from 50 to 200 mM.

In one embodiment, said ionic species are present in a concentration from 50 to 100 mM.

In one embodiment, said ionic species are present in a concentration from 50 to 75 mM.

Regarding cations of mineral origin and, in particular, $Zn^{2+}$, its molar concentration in the composition may be comprised from 0.25 to 20 mM, in particular, from 0.25 to 10 mM or from 0.25 to 5 mM.

In one embodiment, the composition comprises zinc.

In one embodiment, the composition comprises from 0.2 to 2 mM of zinc.

In one embodiment, the composition comprises NaCl.

In one embodiment, the composition comprises from 10 to 250 mM of NaCl.

In one embodiment, the composition comprises from 15 to 200 mM of NaCl.

In one embodiment, the composition comprises from 20 to 150 mM of NaCl.

In one embodiment, the composition comprises from 25 to 100 mM of NaCl.

In one embodiment, the compositions according to the invention also comprise zinc salts in a concentration from 0 to 500 µM per 100 U of insulin.

In one embodiment, the compositions according to the invention also comprise zinc salts in a concentration from 0 to 400 µM per 100 U of insulin.

In one embodiment, the compositions according to the invention also comprise zinc salts in a concentration from 0 to 300 µM per 100 U of insulin.

In one embodiment, the compositions according to the invention also comprise zinc salts in a concentration from 0 to 200 µM per 100 U of insulin.

In one embodiment, the compositions according to the invention also comprise zinc salts in a concentration from 0 to 100 µM per 100 U of insulin.

In one embodiment, the compositions according to the invention also comprise buffers.

In one embodiment, the compositions according to the invention comprise buffers in a concentration from 0 to 100 mM.

In one embodiment, the compositions according to the invention comprise buffers in a concentration from 15 to 50 mM.

In one embodiment, the compositions according to the invention comprise a buffer chosen from the group consisting of a phosphate buffer, Tris (trishydroxymethylaminomethane), and sodium citrate.

In one embodiment, the buffer is sodium phosphate.

In one embodiment, the buffer is Tris (trishydroxymethylaminomethane).

In one embodiment, the buffer is sodium citrate.

In one embodiment, the compositions according to the invention also comprise preservatives.

In one embodiment, the preservatives are chosen from the group consisting of m-cresol and phenol, alone or in mixture.

In one embodiment, the concentration of preservatives is comprised from 10 to 50 mM.

In one embodiment, the concentration of preservatives is comprised from 10 to 40 mM.

In one embodiment, the compositions according to the invention also comprise a surfactant.

In one embodiment, the tensioactive is chosen from the group consisting of propylene glycol and polysorbate.

The compositions according to the invention also comprise additives such as tonicity agents.

In one embodiment, the tonicity agents are chosen from the group consisting of glycerin, sodium chloride, mannitol and glycine.

Compositions according to the invention may also comprise all of the excipients in compliance with the pharmacopoeias and compatible with the insulins used at customary concentrations.

The invention also relates to a pharmaceutical formulation according to the invention characterized in that it is obtained by drying and/or lyophilization.

In the case of local and systemic releases, the envisaged routes of administration are intravenous, subcutaneous, intradermal or intramuscular.

Transdermal, oral, nasal, vaginal, ocular, mouth and pulmonary means of administration are also envisaged.

The invention also relates to a pump, implantable or transportable, comprising a composition according to the invention.

The invention also relates to the use of a composition according to the invention intended to be placed in an implantable or transportable pump.

The invention also relates to formulations at a pH from 6.0 to 8.0, comprising amylin, an amylin agonist receptor or an amylin analogue and a co-polyamino acid according to the invention.

The invention also relates to single-dose formulations at a pH from 6.0 to 8.0 comprising amylin, an amylin agonist receptor or an amylin analogue, a co-polyamino acid according to the invention and a GLP-1, a GLP-1 analogue or a GLP-1 RA as defined above.

The invention also relates to formulations at a pH from 6.6 to 7.8, comprising amylin, an amylin agonist receptor or an amylin analogue and a co-polyamino acid according to the invention.

The invention also relates to single-dose formulations at a pH from 6.6 to 7.8, comprising amylin, an amylin agonist receptor or an amylin analogue and a co-polyamino acid according to the invention, and a prandial insulin as defined above.

The invention also relates to formulations a a pH from 6.6 to 7.6, comprising amylin, an amylin agonist receptor or an amylin analogue and a co-polyamino acid according to the invention.

The invention also relates to single-dose formulations at a pH from 6.6 to 7.6, comprising amylin, an amylin agonist receptor or an amylin analogue and a co-polyamino acid according to the invention, and a prandial insulin as defined above.

In one embodiment, the single-dose formulations also comprise a co-polyamino acid as defined above.

In one embodiment, the formulations are in the form of an injectable solution.

The preparation of a composition according to the invention offers the advantage of being able to be prepared by simply mixingan aqueous solution of amylin, an amylin agonist receptor or an amylin analogue, and a co-polyamino acid bearing carboxylate charges and at least one hydrophobic radical according to the invention, in aqueous solution or in lyophilized form. If necessary, the pH of the preparation is adjusted to a pH from 6.0 to 8.0.

The preparation of a composition according to the invention offers the advantage of being able to be prepared by simply mixing an aqueous solution of amylin, an amylin agonist receptor or an amylin analogue, prandial insulin and a co-polyamino acid bearing carboxylate charges and at least one hydrophobic radical according to the invention, in aqueous solution or in lyophilized form. If necessary, the pH of the preparation is adjusted to a pH from 6.0 to 8.0.

In one embodiment, the mixture of prandial insulin and co-polyamino acid is concentrated by ultrafiltration.

If necessary, the composition of the mixture is adjusted with excipients such as glycerin, m-cresol, zinc chloride and polysorbate (Tween) by the addition of concentrated solutions of these excipients to the mixture. If necessary, the pH of the preparation is adjusted to a pH from 6.0 to 8.0.

In one embodiment, the compositions are characterized in that said compositions have a stability measured by ThT greater than that of a reference composition comprising amylin, an amylin receptor agonist and an amylin analogue, but not comprising a co-polyamino acid bearing carboxylate charges and hydrophobic radicals Hy.

In one embodiment, the compositions are characterized in that said compositions have a stability measured in ThT greater than that of a reference composition comprising amylin receptor agonist and an amylin analogue; in combination with an insulin but not comprising a co-polyamino acid bearing carboxylate charges and hydrophobic radicals Hy.

In one embodiment, the compositions are characterized in that said compositions have a stability measured by ThT greater than that of a reference composition comprising amylin, an amylin receptor agonist and an amylin analogue, in combination with a GLP-1, a GLP-1 analogue or a GLP-1 receptor agonist, but not comprising a co-polyamino acid bearing carboxylate charges and hydrophobic radicals Hy.

In one embodiment, the compositions are characterized in that said compositions have a stability measured by ThT greater than that of a reference composition comprising amylin, an amylin receptor agonist and an amylin analogue, with a GLP-1, a GLP-1 analogue or a GLP-1 receptor agonist, but not comprising a co-polyamino acid bearing carboxylate charges and hydrophobic radicals Hy.

The invention also relates to the use of a co-polyamino acid bearing carboxylate charges and hydrophobic radicals Hy to stabilize a composition comprising amylin receptor agonist and an amylin analogue.

The invention also concerns a use of a co-polyamino acid bearing carboxylate charges and hydrophobic radicals Hy to stabilize a composition comprising amylin receptor agonist and an amylin analogue and a prandial insulin, and possibly a GLP-1, a GLP-1 analogue or a GLP-1 receptor agonist.

The invention also concerns a method for stabilization of a composition amylin, and amylin receptor agonist and an amylin analogue or a method for stabilizing a composition comprising amylin receptor agonist and an amylin analogue and a prandial insulin, and possibly a GLP-1, a GLP-1 analogue or a GLP-1 receptor agonist.

The following examples describe this application without, however, being limitative.

DESCRIPTION OF THE FIGURES

FIG. 1:

This FIGURE graphically represents the determination of the latency time (LT) by fluorescent monitoring of Thioflavin T, on a curve with the value of the fluorescence on the ordinate axis (in u.a., arbitrary units) and the time in minutes on the abscissa.

PART A—SYNTHESIS OF INTERMEDIATE HYDROPHOBIC HYD FOR OBTAINING THE RADICALS -HY

| No. | INTERMEDIATE HYDROPHOBIC COMPOUNDS |
|-----|-------------------------------------|
| A1  | 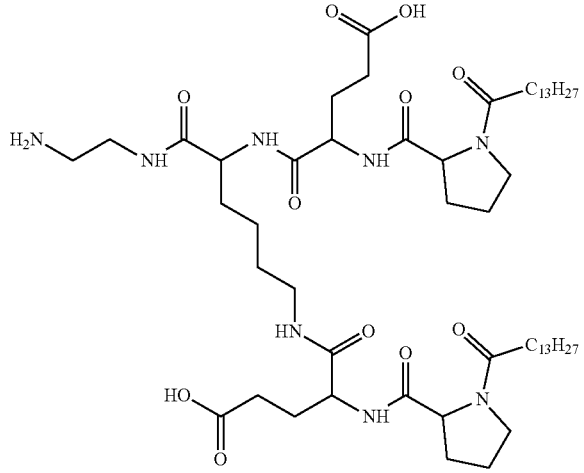 |
| A2  | 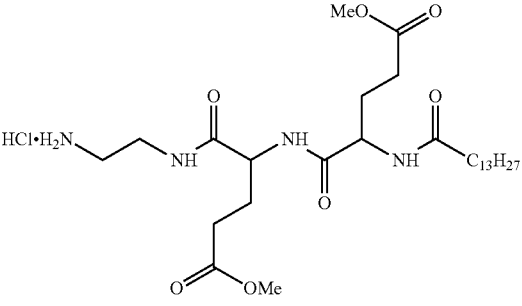 |
| A3  | 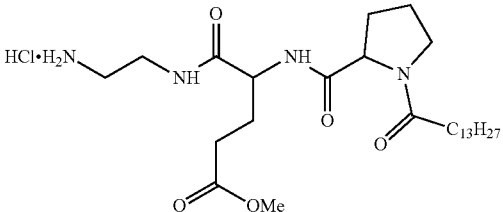 |
| A4  | 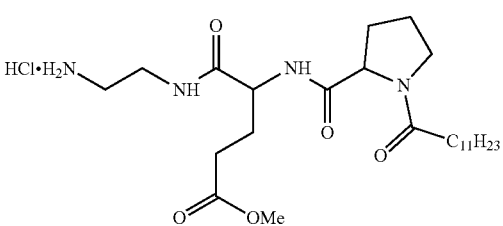 |

-continued
| No. | INTERMEDIATE HYDROPHOBIC COMPOUNDS |
|---|---|
| A5 | 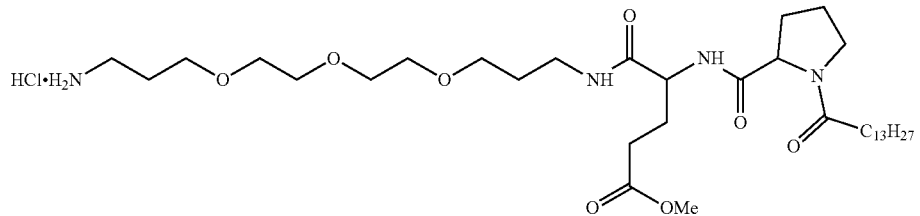 |
| A7 | 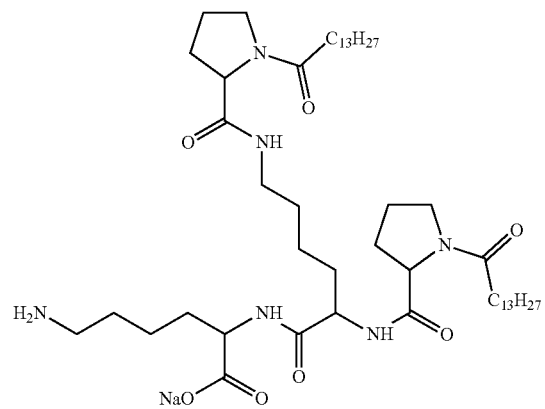 |
| A5a | 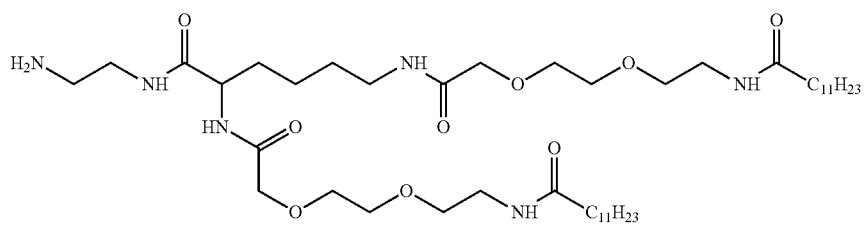 |
| A6a | 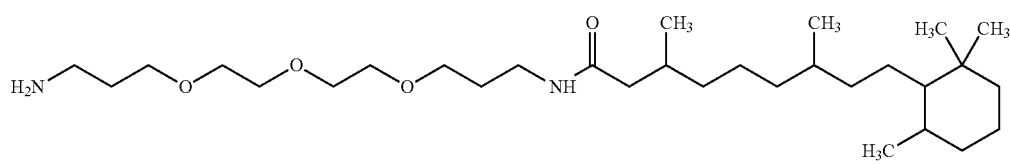 [SMILES: CC(CCCC(C)CC(=O)NCCCOCCOCCOCCCN)CCC1C(C)CCCC1(C)C] |
| A8 | 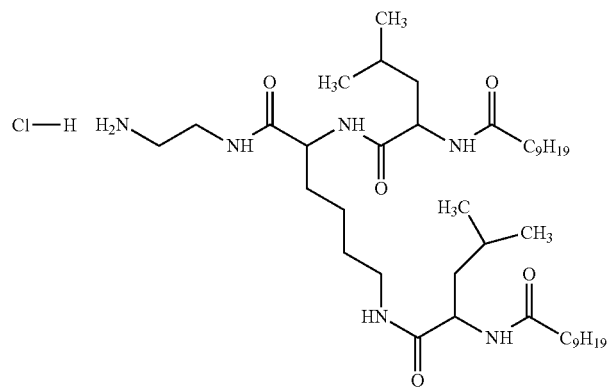 |
| A9 | 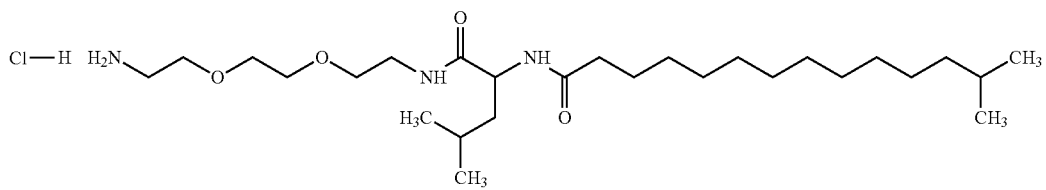 |

-continued
| No. | INTERMEDIATE HYDROPHOBIC COMPOUNDS |
|---|---|
| A10 | 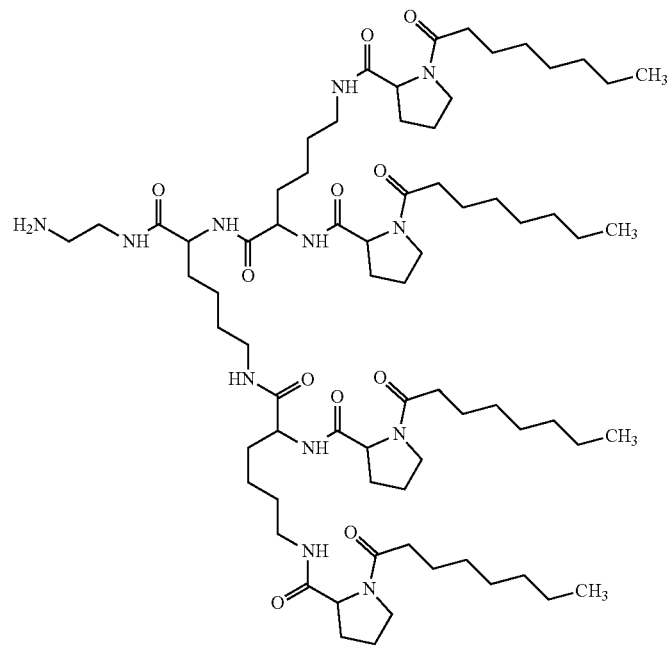 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |
| A11 | 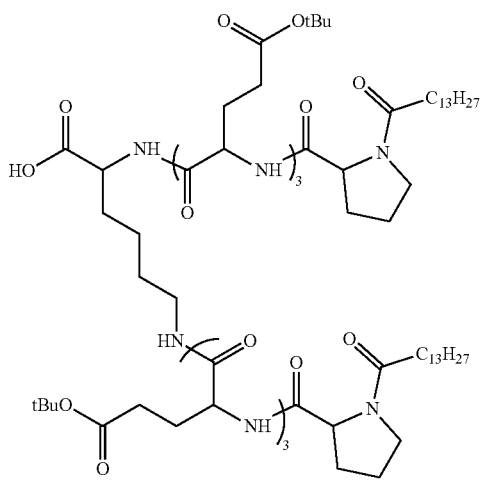 |

| No. | INTERMEDIATE HYDROPHOBIC COMPOUNDS |
|---|---|
| A12 | 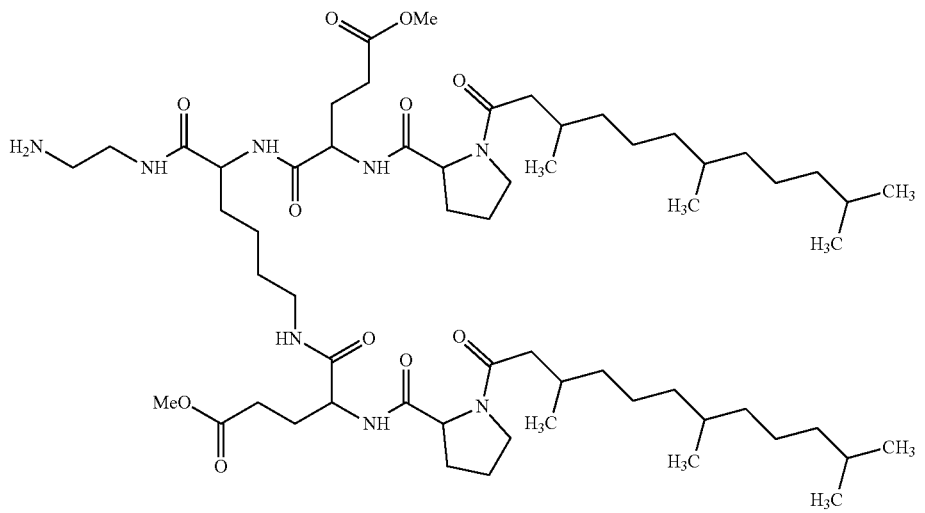 [SMILES: COC(=O)CCC(NC(=O)C1CCCN1C(=O)CC(C)CCCC(C)CCCC(C)C)C(=O)NCCCCC(NC(=O)C(CCC(=O)OC)NC(=O)C1CCCN1C(=O)CC(C)CCCC(C)CCCC(C)C)C(=O)NCCN] |
| A13 | 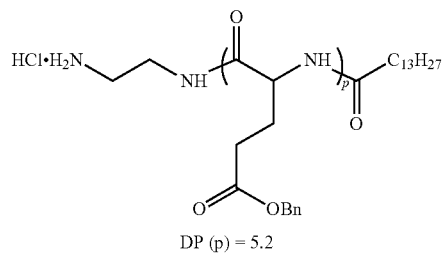
DP (p) = 5.2 |
| A14 | 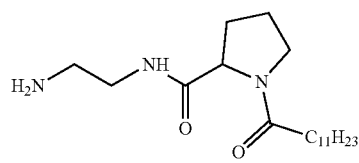 |
| A15 | 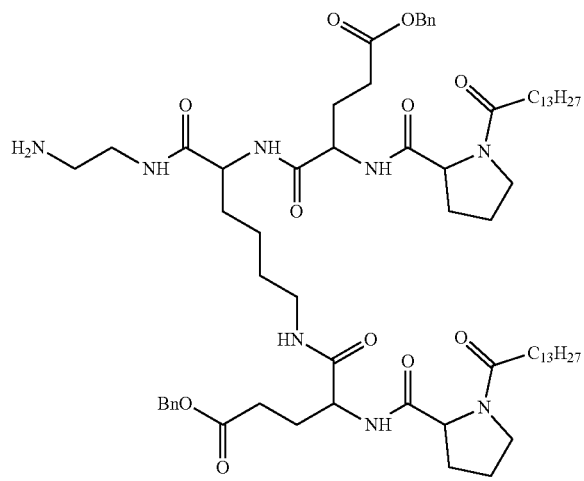 |

| No. | INTERMEDIATE HYDROPHOBIC COMPOUNDS |
|---|---|
| A16 | 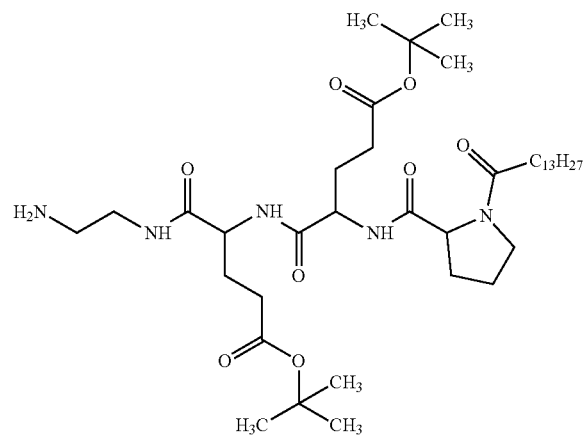 |
| A17 | 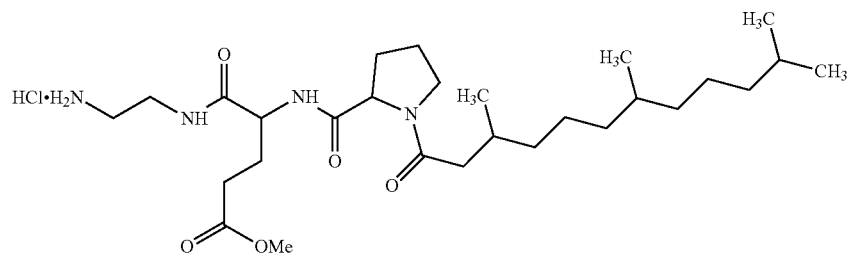 |
| A18 | 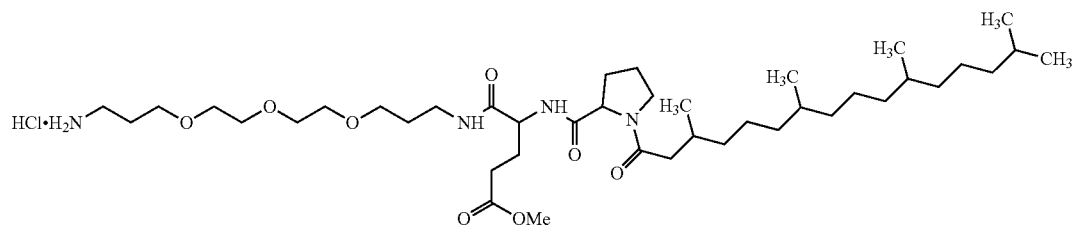 |
| A19 | 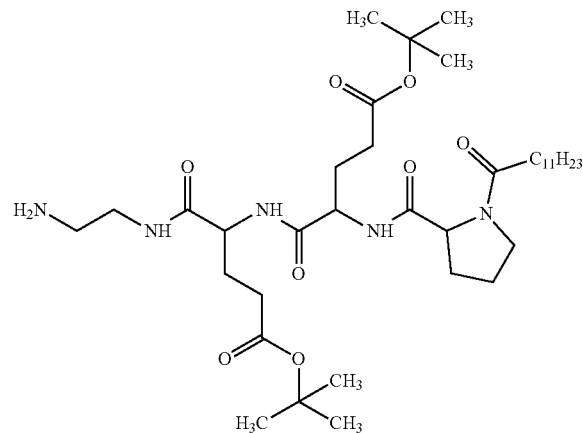 |

| No. | INTERMEDIATE HYDROPHOBIC COMPOUNDS |
|---|---|
| A20 | 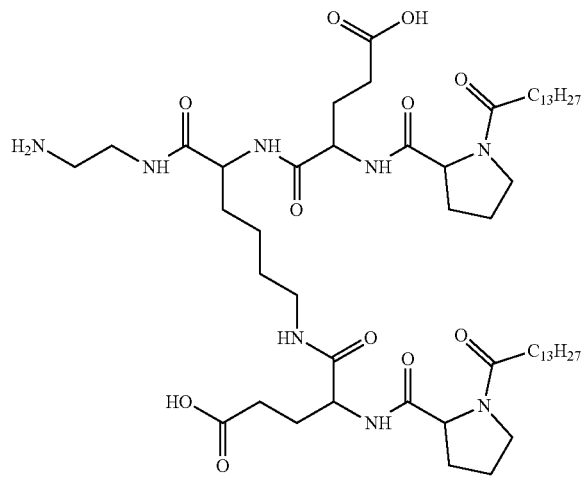 |

Example A1: Molecule A1

Molecule 1: Product Obtained by the Reaction Between Fmoc-Lys(Fmoc)-OH and the Resin 2-Cl-trityl chloride.

To a suspension of Fmoc-Lys(Fmoc)-OH (7.32 g, 12.40 mmol) in dichloromethane (60 mL) at room temperature is added DIPEA (4.32 mL, 24.80 mmol). After complete solubilization (10 min), the solution obtained is poured onto the resin 2-Cl-trityl chloride previously washed in dichloromethane (100-200 mesh, 1% DVB, 1.24 mmol/g) (4.00 g, 4.96 mmol), After stirring for 2 hours at room temperature, HPLC grade methanol (0.8 mL/g resin, 3.2 mL) is added and the medium is stirred at room temperature for 15 minutes. The resin is filtered, successively washed with dichloromethane (3×60 mL), DMF (2×60 mL), dichloromethane (2×60 mL), isopropanol (1×60 mL) and dichloromethane (3×60 mL).

Molecule 2: Product Obtained by the Reaction Between Molecule 1 and a 80:20 DMF/Piperidine Mixture.

Molecule 1, previously washed with DMF, is taken up with a 80:20 DMF/piperidine mixture (60 mL). After 30 minutes of stirring at room temperature, the resin is filtered, successively washed with DMF (3×60 mL), isopropanol (1×60 mL) and dichloromethane (3×60 mL).

Molecule 3: Product Obtained by the Reaction Between Molecule 2 and a Fmoc-Glu(OtBu)-OH.

To a suspension of Fmoc-Glu(OtBu)-OH (10.55 g, 24.80 mmol) and of 1-[bis(dimethylamino)methylene]-1H-1,2,3-triazolo[4,5-b]pyridinium 3-oxide hexafluorophosphate (HATU, 9.43 g, 24.80 mmol) in a mixture 1:1 DMF/dichloromethane (60 mL) is added DIPEA (8.64 mL, 49.60 mmol). After complete solubilization, the solution obtained is poured onto molecule 2. After 2 hours of stirring at room temperature, the resin is filtered, successively washed with DMF (3×60 mL), isopropanol (1×60 mL) and dichloromethane (3×60 mL).

Molecule 4: Product Obtained by the Reaction Between Molecule 3 and a 50:50 DMF/Morpholine Mixture.

Molecule 3, previously washed with DMF, is taken up with a 50:50 DMF/piperidine mixture (60 mL). After 1 hour 15 minutes of stirring at room temperature, the resin is filtered, successively washed with DMF (3×60 mL), isopropanol (1×60 mL) and dichloromethane (3×60 mL).

Molecule 5: Product Obtained by the Reaction Between Molecule 4 and Molecule 11.

Molecule 5 is obtained using a process similar to that used for molecule 3, applied to molecule 4 and to molecule 11 (8.07 g, 24.80 mmol) in DMF (60 mL).

Molecule 6: Product Obtained by the Reaction Between Molecule 5 and a 80:20 dichloromethane/1,1,1,3,3,3-hexafluoro-2-propanol (HFIP) mixture.

Molecule 5 is taken up with a 80:20 dichloromethane/1,1,1,3,3,3-hexafluoro-2-propanol (HFIP) (60 mL) mixture. After 20 minutes of stirring at room temperature, the resin is filtered and washed with dichloromethane (2×60 mL). The solvents are evaporated under reduced pressure. Two co-evaporations are then carried out on the residue with dichloromethane (60 mL) then with diisopropylether (60 mL). The product is purified by chromatography on silica gel (dichloromethane, methanol). A white solid of molecule 6 is obtained.

Yield: 2.92 g (52% in 6 steps)

RMN $^1$H (CD$_3$OD, ppm): 0.90 (6H); 1.22-2.47 (88H); 3.13-3.25 (2H); 3.45-3.76 (4H); 4.24-4.55 (5H).

LC/MS (ESI+): 1131.9 (calculated ([M+H]$^+$): 1131.8).

Molecule 7: Product Obtained by the Reaction Between Molecule 6 and N-Boc ethylenediamine.

To a solution of molecule 6 (2.82 g, 2.49 mmol) in Me-THF (20 mL) at room temperature are successively added N-hydroxybenzotriazole (HOBt, 496 mg, 3.24 mmol) and N-Boc ethylenediamine (BocEDA, 440 mg, 2.74 mmol). The mixture is cooled to 0° C. then (3-dimethylaminopropyl)-N'-ethylcarbodiimide (EDC, 621 mg, 3.24 mmol) hydrochloride is added. The medium is stirred for 15 minutes at 0° C. then for 18 h at room temperature. The organic phase is diluted with dichloromethane (30 mL) and washed with a saturated NH4Cl aqueous solution (2×20 mL), a saturated NaHCO$_3$ aqueous solution (2×20 mL), and a saturated NaCl aqueous solution (2×20 mL). The organic phase is dried over Na$_2$SO$_4$, filtered and concentrated under reduced pressure. A white solid of molecule 7 is obtained after recrystallization in acetontrile Yield: 2.47 g (78%)

RMN $^1$H (CDCl$_3$, ppm): 0.87 (6H); 1.09-1.77 (77H); 1.84-2.49 (20H); 2.99-3.83 (10H); 4.16-4.25 (1H); 4.27-

4.47 (4H); 5.68 (0.1H); 5.95-6.08 (0.9H); 6.91-7.14 (2H); 7.43-7.57 (1H); 7.68-7.78 (1H); 8.22-8.35 (1H).

LC/MS (ESI+): 1273.9 (calculated ([M+H]$^+$): 1273.9).

Molecule A1

To a solution of molecule 7 (2.47 g, 1.94 mmol) in dichloromethane (20 mL) at room temperature is added a solution of 4 N HCl in dioxane (7.27 mL) then the medium is stirred for 16 hours at room temperature. After concentration under reduced pressure, co-evaporation and washing with diisopropylether, a white solid of molecule A1 in the form of a HCl salt is obtained. This solid is solubilized in water (100 mL) then the pH is adjusted to 7 by the addition of an aqueous solution of NaOH 1 N. The solution is lyophilized and the lyophilisate is dried by co-evaporation in the toluene. A white solid of molecule A1 is obtained.

Yield: 1.64 g (80%)

RMN $^1$H (CD$_2$OD, ppm): 0.90 (6H); 1.15-2.59 (70H); 3.06-3.86 (10H); 4.19-4.43 (5H).

LC/MS (ESI+): 1061.8 (calculated ([M+H]$^+$): 1061.8).

Example A2: Molecule A2

Molecule 8: Product Obtained by the Coupling Between Myristic Acid and methyl-L-glutamate.

To a solution of myrisitic acid (35.0 g, 153.26 mmol) in tetrahydrofurane (THF) (315 mL) at room temperature are successively added N-hydroxysuccinimide (NHS, 17.81 g, 154.79 mmol) and N,N-dicyclohexylcarboxydiimide (DCC, 31.94 g, 154.79 mmol). The medium is stirred for 48 hours while raising the temperature to room temperature, filtered on the sinter filter, then added to a solution of methyl-L-glutamate (24.95 g, 154.9 mmol) and N,N-diisopropylethylamine (DIPEA, 99.0 g, 766.28 mmol) in water (30 mL). The reaction medium is stirred at 20° C. for 48 hours then concentrated under reduced pressure. Water (200 mL) is added and the mixture obtained is taken up by the successive addition of ethyl acetate (AcOEt, 100 mL) then a 5% aqueous solution of Na$_2$CO$_3$ (50 mL). The aqueous phase is then washed again with AcOEt (100 mL), acidified by the addition of an aqueous solution of 10% HCl and the product is extracted with dichloromethane (DCM, 3×150 mL). The organic phase is dried over Na$_2$SO$_4$, filtered and concentrated under reduced pressure. A white solid of molecule 8 is obtained.

Yield: 47.11 g (84%)

RMN $^1$H (CDCl$_3$, ppm): 0.87 (3H); 1.07-1.66 (22H); 2.02-2.11 (1H); 2.18-2.36 (3H); 2.39-2.47 (1H); 2.50-2.58 (1H); 3.69 (3H); 4.54-4.59 (1H); 6.62 (1H); 8.26 (1H).

LC/MS (ESI+): 372.2 (calculated ([M+H]$^+$): 372.3).

Molecule 9: Product Obtained by the Coupling Between Molecule 8 and methyl-L-Glutamate.

Using a process similar to that used for the preparation of molecule 8 and applied to molecule 8 (35.0 g, 94.21 mmol) and to methyl-L-glutamate (15.33 g, 95.15 mmol), a white solid of molecule 9 is obtained after recrystallization in acetonitrile Yield: 24.0 g (49%)

RMN $^1$H (DMSO-d6, ppm): 0.85 (3H); 1.06-1.51 (22H); 1.70-1.94 (3H); 1.96-2.15 (3H); 2.29-2.40 (4H); 3.58 (3H); 3.58 (3H); 4.16-4.22 (1H); 4.25-4.32 (1H); 7.93 (1H); 8.16 (1H); 12.66 (1H).

LC/MS (ESI+): 515.3 (calculated ([M+H]$^+$): 515.3).

Molecule 10: Product Obtained by the Reaction Between Molecule 9 and N-Boc ethylenediamine.

To a suspension of molecule 9 (24.0 g, 46.63 mmol) in DCM (285 mL) at 0° C. are successively added HOBt (714 mg, 46.66 mmol), BocEDA (8.97 g, 55.96 mmol) in solution in DCM (25 mL) then EDC (9.83 g, 51.30 mmol). The medium is stirred for 1 hour at 0° C. then for 18 h at room temperature. The organic phase is washed with a saturated NaHCO$_3$ aqueous solution (2×300 mL), an aqueous solution of 1 N HCl (2×300 mL), a saturated NaCl aqueous solution (500 mL). Methanol (40 mL) is added, the organic phase is dried over Na$_2$SO$_4$, filtered and concentrated under reduced pressure. A white solid of molecule 10 is obtained after recrystallization in acetonitrile Yield: 27.15 g (89%)

RMN $^1$H (CDCl$_3$, ppm): 0.87 (3H); 1.07-1.68 (22H); 1.42 (9H); 1.97-2.18 (4H); 2.22-2.31 (2H); 2.35-2.55 (4H); 3.19-3.29 (2H); 3.30-3.38 (2H); 3.66 (3H); 3.68 (3H); 4.34-4.41 (1H); 4.42-4.48 (1H); 5.54 (1H); 6.99-7.18 (2H) 7.56 (1H).

LC/MS (ESI+): 657.4 (calculated ([M+H]$^+$): 657.4).

Molecule A2

To a solution of molecule 10 (27.15 g, 41.33 mmol) in a DCM/methanol mixture (410 mL) at 0° C. is added a solution of 4 N HCl in dioxane (51.7 mL) then the medium is stirred for 2 hours at 0° C., then 16 hours at room temperature. After concentration under reduced pressure, co-evaporation in methanol (2×150 mL), a white solid of molecule A2 in the form of a hydrochloride salt is obtained after recrystallization in acetontrile.

Yield: 23.2 g (95%)

RMN $^1$H (DMSO-d6, ppm): 0.85 (3H); 1.05-1.52 (22H); 1.71-1.85 (2H); 1.87-2.03 (2H); 2.07-2.18 (2H); 2.24-2.37 (4H); 2.84 (2H); 3.24-3.38 (2H); 3.58 (3H); 3.58 (3H); 4.17-4.24 (2H); 7.95-8.08 (5H); 8.14 (1H).

LC/MS (ESI+): 557.3 (calculated ([M+H]$^+$): 557.4).

Example A3: Molecule A3

Molecule 11: Product Obtained by the Reaction Between Myristoyl Chloride and L-proline.

To a solution of L-proline (300.40 g, 2.61 mol) in aqueous 2 N soda (1.63 L) at 0° C. is slowly added 1 h myristoyl chloride (322 g, 1.30 mol) in solution in dichloromethane (DCM, 1.63 L). After this addition, the reaction medium is raised to 20° C. over 3 h, then stirred for 2 h. The mixture is cooled to 0° C. then a 37% HCl aqueous solution (215 mL) is added over 15 minutes. The reaction medium is stirred for 1 hour from 0° C. to 20° C. The organic phase is separated, washed with a 10% HCl aqueous solution (3×430 mL), a saturated NaCl aqueous solution (430 mL), dried over Na$_2$SO$_4$, filtered through cotton, then concentrated under reduced pressure. The residue is solubilized in heptane (1.31 L) at 50° C., then the solution is progressively cooled to room temperature. After priming crystallization using a glass rod, the medium is heated again at 40° C. for 30 minutes, then returned to room temperature over 4 hours. A white solid is obtained after filtration on sintered filter, washing with heptane (2×350 mL) and drying under reduced pressure.

Yield: 410 g (97%)

RMN $^1$H (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 326.4 (calculated ([M+H]$^+$): 326.3; ([2M+H]$^+$): 651.6).

Molecule 12: Product Obtained by the Coupling Between Molecule 11 and methyl-L-glutamate.

Using a process similar to that used for the preparation of molecule 8 and applied to molecule 11 (30.0 g, 92.17 mmol) and to methyl-L-glutamate (15.60 g, 96.78 mmol), a white solid of molecule 12 is obtained after recrystallization in refluxing acetone, cooling to room temperature and filtration on sintered filter. The filtrate is evaporated and the residue is precipitated in acetone, as above, with this operation being repeated 3 times.

Yield: 15.5 g (36%)

RMN $^1$H (DMSO-d6, ppm): 0.85 (3H); 1.07-1.37 (20H); 1.40-1.50 (2H); 1.71-2.27 (8H); 2.30-2.40 (2H); 3.28-3.54 (12H); 3.58 (1.3H); 3.59 (1.7H); 4.14-4.28 (1H); 4.28-4.37 (1H); 8.06 (0.55H); 8.33 (0.45H); 12.64 (1H).

LC/MS (ESI+): 469.2 (calculated ([M+H]$^+$): 469.3).

Molecule 13: Product Obtained by the Reaction Between Molecule 12 and N-Boc ethylenediamine.

Using a process similar to that used for the preparation of molecule 10 and applied to molecule 12 (15.5 g, 33.05 mmol) and to methyl-L-glutamate (5.83 g, 36.36 mmol), a white solid of molecule 13 is obtained after recrystallization in acetontrile Yield: 19.8 g (83%)

RMN $^1$H (DMSO-d6, ppm): 0.85 (3H); 1.07-1.55 (22H); 1.37 (9H); 1.69-2.19 (7H); 2.22-2.36 (3H); 2.91-3.17 (4H); 3.28-3.60 (5H); 4.11-4.18 (0.7H); 4.20-4.28 (1H); 4.38-4.42 (0.3H); 6.74 (1H); 7.64 (0.7H); 7.87 (0.7H); 7.98 (0.3H); 8.22 (0.3H).

LC/MS (ESI+): 611.4 (calculated ([M+H]$^+$): 611.4).

Molecule A3

Using a process similar to that used for the preparation of molecule A2 and applied to molecule 13 (16.8 g, 27.50 mmol), a white solid of molecule A3 in the form of a hydrochloride salt is obtained after recrystallization in acetontrile Yield: 13.5 g (90%)

RMN $^1$H (DMSO-d6, ppm): 0.85 (3H); 1.08-1.52 (22H); 1.70-2.37 (10H); 2.80-2.90 (2H); 3.22-3.62 (4H); 3.57 (3H); 4.15-4.28 (1.75H); 4.41-4.44 (0.25H); 7.81-8.13 (4.5H); 8.24-8.29 (0.25H) 8.33-8.39 (0.25H).

LC/MS (ESI+): 511.3 (calculated ([M+H]$^+$): 511.4).

Example A4: Molecule A4

Molecule 14: Product Obtained by the Reaction Between Lauroyl Chloride and L-proline Using a process similar to that used for the preparation of molecule 11 and applied to lauroyl chloride (27.42 g, 685.67 mmol) and to L-proline (60.0 g, 247.27 mmol), a white solid of molecule 14 is obtained.

Yield: 78.35 g (96%)

RMN $^1$H (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI+): 298.1 (calculated ([M+H]$^+$): 298.2).

Molecule 15: Product Obtained by the Coupling Between Molecule 14 and methyl-L-glutamate.

Using a process similar to that used for the preparation of molecule 8 and applied to molecule 14 (34.64 g, 116.46 mmol) and to methyl-L-glutamate (19.14 g, 118.79 mmol), a white solid of molecule 15 is obtained after recrystallization in acetontrile Yield: 37.28 g (73%)

RMN $^1$H (CDCl$_3$, ppm): 0.85 (3H); 1.08-1.42 (16H); 1.54-1.06 (2H); 1.80-2.47 (10H); 3.42-3.80 (2H); 3.65 (2.55H); 3.67 (0.45H); 4.37-4.40 (0.15H); 4.51-4.58 (0.85H); 4.58-4.67 (1H); 7.26 (0.15H) 7.65 (0.85H); 8.06 (1H).

LC/MS (ESI+): 441.1 (calculated ([M+H]$^+$): 441.3).

Molecule 16: Product Obtained by the Reaction Between Molecule 15 and N-Boc ethylenediamine.

Using a process similar to that used for the preparation of molecule 10 and applied to molecule 15 (37.30 g, 84.66 mmol) and to methyl-L-glutamate (14.92 g, 93.13 mmol), a white solid of molecule 16 is obtained after recrystallization in acetontrile Yield: 43.10 g (87%)

RMN $^1$H (DMSO-d6, ppm): 0.85 (3H); 1.08-1.53 (18H); 1.37 (9H); 1.70-2.36 (10H); 2.91-3.60 (9H); 4.11-4.18 (0.7H); 4.21-4.28 (1H); 4.38-4.42 (0.3H); 6.38 (0.1H); 6.74 (0.9H); 7.65 (0.7H); 7.87 (0.7H); 7.99 (0.3H); 8.22 (0.3H).

LC/MS (ESI+): 583.4 (calculated ([M+H]$^+$): 583.4).

Molecule A4

Using a process similar to that used for the preparation of molecule A2 and applied to molecule 16 (43.10 g, 73.96 mmol), a white solid of molecule A4 in the form of a hydrochloride salt is obtained after recrystallization in acetontrile Yield: 31.90 g (83%)

RMN $^1$H (DMSO-d6, ppm): 0.85 (3H); 1.05-1.37 (16H); 1.39-1.52 (2H); 1.70-2.37 (10H); 2.29-2.91 (2H); 3.20-3.62 (7H); 4.16-4.29 (1.7H); 4.42-4.46 (0.3H); 7.86-8.18 (4.6H); 8.32 (0.3H); 8.40 (0.3H).

LC/MS (ESI+): 483.2 (calculated ([M+H]$^+$): 483.3).

Example A5: Molecule A5

Molecule 17: Product Obtained by the Reaction Between 1-amino-4,7,10-trioxa-13-tridecane amine and tert-butyl phenylcarbonate.

To a solution of 1-amino-4,7,10-trioxa-13-tridecane amine and (112.29 g, 509.71 mmol) in ethanol (510 mL) at 80° C. is added, drop by drop, tert-butyl phenylcarbonate (49.50 g, 254.86 mmol). The reaction medium is stirred at 80° C. for 3 hours 30 minutes then concentrated under reduced pressure. The residue is solubilized in water (250 mL), the pH is adjusted to 2.3 with a 37% HCl solution, and the mixture is extracted with methyl tert-butylether (MTBE, 2×150 mL). The aqueous phase is basified to pH 12.6 by the addition of a solution of 2 N NaOH and extracted with DCM (3×250 m>). The organic phase is washed with an aqueous solution of 1 N NaOH (1×100 mL), a saturated NaCl aqueous solution (100 mL), dried over Na$_2$SO$_4$, filtered and concentrated under reduced pressure. A yellow oil of molecule 17 is obtained.

Yield: 54.4 g (67%)

RMN $^1$H(CDCl$_3$, ppm): 1.40-1.58 (11H); 1.73-1.81 (4H); 2.80-2.84 (2H); 3.20-3.70 (14H); 5.11 (1H).

LC/MS (ESI+): 321.2 (calculated ([M+H]$^+$): 321.2).

Molecule 18: Product Obtained by the Coupling Between Molecule 12 and Molecule 17.

Using a process similar to that used for the preparation of molecule 10 and applied to molecule 12 (20.46 g, 43.66 mmol) and to molecule 17 (16.79 g, 52.39 mmol), a white wax of molecule 18 is obtained after purification by flash chromatography (eluent: DCM, methanol), solubilization of the residue in DCM (300 mL), washings of the organic phase with an aqueous solution of NaHCO$_3$ (2×150 mL), an aqueous solution of 10% HCl (2×150 mL), a saturated NaCl aqueous solution (2×150 mL), dried over Na$_2$SO$_4$ and concentrated under reduced pressure.

Yield: 30.15 g (90%)

RMN $^1$H (DMSO-d6, ppm): 0.85 (3H); 1.09-1.52 (31H); 1.55-1.67 (4H); 1.69-2.36 (10H); 2.91-2.98 (2H); 3.02-3.17 (2H); 3.28-3.61 (17H); 4.12-4.17 (0.7H); 4.20-4.28 (1H); 4.39-4.42 (0.3H); 6.37 (0.1H); 6.71 (0.9H); 7.59 (0.7H); 7.85 (0.7H); 7.94 (0.3H); 8.21 (0.3H).

LC/MS (ESI+): 771.4 (calculated ([M+H]$^+$): 771.5).

Molecule A5

Using a process similar to that used for the preparation of molecule A2 and applied to molecule 18 (30.0 g, 38.91 mmol), a white solid of molecule A5 in the form of a hydrochloride salt is obtained after solubilization of the residue in water (500 mL) and lyophilization.

Yield: 25.2 g (91%)

RMN $^1$H (DMSO-d6, ppm): 0.85 (3H); 1.06-1.37 (20H); 1.39-1.52 (2H); 1.58-1.66 (2H); 1.70-2.37 (12H); 2.78-2.85 (2H); 3.01-3.15 (2H); 3.31-3.62, (17H); 4.11-4.17 (0.7H); 4.19-4.27 (1H); 4.41-4.44 (0.3H); 7.63-7.71 (0.7H); 7.90-8.24 (4H); 8.28-8.35 (0.3H); LC/MS (ESI+): 671.4 (calculated ([M+H]$^+$): 671.5).

Example A7: Molecule A7

Molecule 21: Product Obtained by the Coupling Between Molecule 11 and L-lysine.

Using a process similar to that used for the preparation of molecule 8 and applied to molecule 11 (133.00 g, 408.61 mmol) and to L-lysine (31.36 g, 214.52 mmol), a white solid of molecule 21 is obtained after crystallization 2 times in acetone.

Yield: 106.50 g (68%)

RMN $^1$H (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).

LC/MS (ESI): 761.8 (calculated ([M+H]$^+$): 762.1).

Molecule 22: Product Obtained by the Coupling Between Molecule 21 and Methyl N-Boc-L-lysinate.

Using a process similar to that used for the preparation of molecule 10 and applied to molecule 21 (43.00 g, 56.50 mmol) in solution in THF and to methyl N-Boc-L-lysinate hydrochloride (20.12 g, 67.79 mmol), a transparent solid of molecule 22 is obtained and used without further purification.

Yield: 55.80 g (98%)

RMN $^1$H (DMSO-d6, ppm): 0.86 (6H); 1.08-2.03 (64H); 1.37 (9H); 2.07-2.30 (4H); 2.84-3.09 (4H); 3.29-3.57 (4H); 3.58-3.65 (3H); 4.14-4.43 (4H); 6.40 (0.1H); 6.74 (0.9H); 7.69 (0.6H); 7.82 (0.6H); 7.95-8.06 (1H); 8.11-8.20 (0.4H); 8.26 (0.4H).

LC/MS (ESI): 1003.8 (calculated ([M+H]$^+$): 1003.8).

Molecule 23: Product Obtained by the Saponification of Molecule 23.

A solution of molecule 22 (55.80 g, 55.61 mmol) in a mixture of 1:1 THF/water (370 mL) at 0° C. is taken up by slow addition of aLiOH solution (2.00 g, 83.41 mmol) in water (185 mL). After 16 hours of stirring at 0° C., the medium is concentrated under reduced pressure and the residue is redissolved in water (500 mL). DCM (500 mL) is added, the heterogeneous mixture is cooled to 10° C. and acidified by the addition of an aqueous solution of 10% HCl to pH 1. The aqueous phase is extracted with DCM (2×300 mL), the combined organic phases are washed with a saturated NaCl aqueous solution (2×300 mL), dried over Na$_2$SO$_4$, filtered and concentrated under reduced pressure. A white solid of molecule 23 is obtained after crystallization in acetone.

Yield: 46.10 g (84%)

RMN $^1$H (pyridine-d6, ppm): 0.85 (6H); 1.05-2.03 (67H); 2.07-2.61 (10H); 3.12-3.93 (8H); 4.54-4.93 (2H); 4.98-5.16 (2H); 7.35-7.45 (1H); 8.34-8.63 (1H); 8.94-9.41 (2H).

LC/MS (ESI): 989.8 (calculated ([M+H]$^+$): 989.8).

Molecule A7

To a solution of molecule 23 (12.00 g, 12.13 mmol) in dichloromethane (40 mL) at 0° C. is added a solution of 4 N HCl in dioxane (15.20 mL) then the medium is stirred for 15 hours at 0° C. and 5 hours at room temperature. The reactant mixture is concentrated under reduced pressure, the residue is solubilized in a mixture of DCM (120 mL) and 2 N NaOH (60 mL). After separation of the phases, the organic phase is washed by a solution of 2 N NaOH (60 mL), dried over Na$_2$SO$_4$ and concentrated under reduced pressure.

Yield: 10.90 g (98%)

RMN $^1$H (DMSO-d6, ppm): 0.86 (6H); 1.05-2.27 (70H); 2.45-2.52 (2H); 2.90-3.58 (6H); 3.67-3.76 (1H); 4.02-4.10 (0.6H); 4.11-4.17 (0.4H); 4.20-4.26 (0.6H); 4.30-4.39 (1H); 4.42-4.46 (0.4H); 7.29-7.42 (1H); 7.71-7.80 (0.6H); 7.97-8.05 (0.6H); 8.10-8.24 (0.4H); 8.33-8.45 (0.3H);

LC/MS (ESI): 887.7 (calculated ([M–H]$^-$): 887.7).

Example A5a: Molecule A5a

Molecule 3a: Product Obtained by the Reaction Between Fmoc-Lys(Fmoc)-OH and the Resin 2-Cl-trityl chloride.

To a suspension of Fmoc-Lys(Fmoc)-OH (7.32 g, 12.40 mmol) in DCM (60 mL) at room temperature is added DIPEA (4.32 mL, 24.80 mmol). After complete solubilization (10 min), the solution obtained is poured onto the resin 2-Cl-trityl chloride (100-200 mesh, 1% DVB, 1.24 mmol/g) (4.00 g, 4.96 mmol) previously washed with DCM in a reactor suited for peptide synthesis on a solid medium. After stirring for 2 hours at room temperature, HPLC grade methanol (0.8 mL/g resin, 3.2 mL) is added and the medium is stirred at room temperature for 15 minutes. The resin is filtered, successively washed with DCM (3×60 mL), DMF (2×60 mL), DCM (2×60 mL), isopropanol (1×60 mL) and DCM (3×60 mL).

Molecule 4a: Product Obtained by the Reaction Between Molecule 3a and a 80:20 DMF/Piperidine Mixture.

Molecule 3a, previously washed with DMF, is taken up with a 80:20 DMF/piperidine mixture (60 mL). After 30 minutes of stirring at room temperature, the resin is filtered, successively washed with DMF (3×60 mL), isopropanol (1×60 mL) and DCM (3×60 mL).

Molecule 5a: Product Obtained by Reaction Between Molecule 4a and 8-acid (9-Fluorenylmethyloxycarbonyl-amino)-3,6-dioxaoctanoic (Fmoc-O2Oc-OH).

To a suspension of Fmoc-O2Oc-OH (9.56 g, 24.80 mmol) and of 1-[bis(dimethylamino)methylene]-1H-1,2,3-triazolo[4,5-b]pyridinium 3-oxide hexafluorophosphate (HATU, 9.43 g, 24.80 mmol) in a mixture 1:1 DMF/DCM (60 mL) is added DIPEA (8.64 mL, 49.60 mmol). After complete solubilization, the solution obtained is poured onto molecule 4a. After 2 hours of stirring at room temperature, the resin is filtered, successively washed with DMF (3×60 mL), isopropanol (1×60 mL) and dichloromethane (3×60 mL).

Molecule 6a: Product Obtained by the Reaction Between Molecule 5a and a 80:20 DMF/Piperidine Mixture.

Using a process similar to that used for molecule 4a, applied to molecule 5a, molecule 6a is obtained.

Molecule 7a: Product Obtained by the Reaction Between Molecule 6a and Lauric Acid.

Molecule 7a is obtained using a process similar to that used for molecule 5a, applied to molecule 6a and lauric acid (4.97 g, 24.80 mmol) in DMF (60 mL), molecule 7a is obtained.

Molecule 8a: Product Obtained by the Reaction Between Molecule 7a and a 80:20 dichloromethane/1,1,1,3,3,3-hexafluoro-2-propanol (HFIP) Mixture.

Molecule 7a is taken up with a 80:20 dichloromethane/ 1,1,1,3,3,3-hexafluoro-2-propanol (HFIP) (60 mL) mixture. After 20 minutes of stirring at room temperature, the resin is filtered and washed with dichloromethane (2×60 mL). The solvents are evaporated under reduced pressure. Two co-evaporations are then carried out on the residue with dichloromethane (60 mL) then with diisopropylether (60 mL). A white solid of molecule 8a is obtained after recrystallization in acetontrile Yield: 2.63 g (66% in 6 steps)

RMN $^1$H (CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (1H); 7.38-7.54 (1H).

LC/MS (ESI): 801.6 (calculated ([M+H]$^+$): 801.6).

Molecule 9a: Product Obtained by the Reaction Between Molecule 8a and N-Boc ethylenediamine.

To a solution of molecule 8a (2.63 g, 3.29 mmol) in chloroform (20 mL) at room temperature are successively added HOBt (654 mg, 4.27 mmol) and BocEDA (580 mg, 3.62 mmol). The mixture is cooled to 0° C. then EDC (819 mg, 4.27 mmol) is added. The medium is stirred for 15 minutes at 0° C. then for 18 h at room temperature. The organic phase is washed with a saturated NH4Cl aqueous solution (2×10 mL), a NaHCO$_3$ saturated aqueous solution (2×10 mL), and a saturated NaCl aqueous solution (2×10 mL). The organic phase is dried over Na$_2$SO$_4$, filtered and concentrated under reduced pressure. A white solid of molecule 9a is obtained after purification by chromatography on silica gel (eluent: dichloromethane, methanol).

Yield: 2.37 g (76%)

RMN $^1$H (CDCl$_3$, ppm): 0.87 (6H); 1.08-1.47 (34H); 1.43 (9H); 1:48-170 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5a

To a solution of molecule 9a (2.37 g, 2.51 mmol) in dichloromethane (50 mL) at room temperature is added a solution of 4 N HCl in dioxane (6.3 mL) then the medium is stirred for 2 hours at room temperature. After concentration under reduced pressure, the residue is solubilized in dichloromethane (50 mL) then washed with an aqueous solution of 1 N NaOH (2×12.5 mL) and a saturated NaCl aqueous solution (25 mL). The organic phase is dried over Na$_2$SO$_4$, filtered and concentrated under reduced pressure. A white solid of molecule A5a is obtained after recrystallization in acetontrile Yield: 1.57 g (74%)

RMN $^1$H (CDCl$_3$, ppm): 0.87 (6H); 1.08-1.43 (34H); 1.48-1.71 (7H); 1:74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).

LC/MS (ESI): 843.6 (calculated ([M+H]$^+$): 843.7).

Example A6a: Molecule A6a

Molecule 10a: Product Obtained by the Hydrogenation of Retinoic Acid.

A solution of retinoic acid (19.0 g, 63.24 mmol) in methanol (450 mL) in the presence of 10% palladium on carbon (1.9 g) is placed in a hydrogen atmosphere (1 atm) at room temperature. After overnight, the reaction medium is filtered on sintered filter then the filtrate is concentrated under reduced pressure. A colorless oil of molecule 10a is obtained.

Yield: 19.50 g (99%)

RMN $^1$H (CDCl$_3$, ppm): 0.45-2.01 (35H); 2.10-2.17 (1H); 2.33-2.38 (1H); 11.14 (1H).

LC/MS (ESI): 309.3 (calculated ([M–H]$^+$): 309.3).

Molecule 11a: Product Obtained by the Reaction Between Boc-1-amino-4,7,10-trioxa-13-tridecane amine and Molecule 10a.

Using a process similar to that used for the preparation of molecule 9a applied to molecule 10a (19.3 g, 62.15 mmol) and to BocTOTA (23.9 g, 74.58 mmol), an orange oil of molecule 11a is obtained.

Yield: 37.05 g (97%)

RMN $^1$H (CDCl$_3$, ppm): 0.43-1.71 (49H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).

LC/MS (ESI): 613.5 (calculated ([M+H]$^+$): 613.5).

Molecule A6a

Using a process similar to that used for the preparation of molecule A5a applied to molecule 11a (34.9 g, 56.94 mmol), an orange oil of molecule A6a is obtained.

Yield: 28.5 g (97%)

RMN $^1$H (CDCl$_3$, ppm): 0.41-1.96 (42H); 2.13 (1H); 2.78 (2H); 3.31-3.36 (2H); 3.53 (4H); 3.55-3.58 (4H); 3.60-3.63 (4H); 6.43 (1H).

LC/MS (ESI): 513.5 (calculated ([M+H]$^+$): 513.5).

Example A8: Molecule A8

Molecule 15a: Product Obtained by the Reaction Between Decanoic Acid and L-leucine.

Using a process similar to that used for the preparation of molecule 8 and applied to decanoic acid (8.77 g, 50.94 mmol) and to L-leucine (7.00 g, 53.36 mmol), a white solid of molecule 15a is obtained.

Yield: 9.17 g (66%)

RMN $^1$H (DMSO-d6, ppm): 0.82-0.89 (9H); 1.18-1.65 (17H); 2.04-2.14 (2H); 4.19-4.23 (1H); 7.98 (1H); 12.40 (1H).

LC/MS (ESI): 286.2 (calculated ([M+H]$^+$): 286.2).

Molecule 16a: Product Obtained by the Reaction Between Molecule 15a and L-lysine methylic ester.

To a solution of molecule 15a (9.16 g, 32.11 mmol) in THF (160 mL) are successively added triethylamine (8.12 g, 80.27 mmol) and 2-(1H-benzotriazol-1-yl)-1,1,3,3-tetramethyluronium tetrafluoroborate (TBTU) and the medium is stirred for 30 minutes at room temperature. Dichlorhydride methyl ester of L-lysine (3 g, 16.86 mmol) is added and the reaction medium is stirred for 3 hours, then concentrated under reduced pressure. The residue is diluted with AcOEt (200 mL), the organic phase is filtered and washed with an aqueous solution of 1 N HCl, then with water, dried over Na$_2$SO$_4$, filtered and concentrated under reduced pressure. A white solid of molecule 16a is obtained after trituration of the residue in acetontrile Yield: 7.33 g (66%)

RMN $^1$H (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).

LC/MS(ESI) 695.7 (calculated ([M+H]$^+$): 695.6).

Molecule 17a: Product Obtained by the Saponification of Molecule 16a.

To a solution of molecule 16a (7.33 g, 10.55 mmol) in a THF/methanol/water (105 mL) mixture is added LiOH (505.13 mg, 21.09 mmol) a 0° C., then the medium is stirred for 20 hours at room temperature and concentrated under reduced pressure. The aqueous phase is acidified with a solution of 1 N HCl to pH 1 and the solid formed is filtered, washed with water and dried under reduced pressure resulting in a white solid of molecule 17a.

Yield: 7.09 g (99%)

RMN $^1$H (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).

LC/MS (ESI): 681.7 (calculated ([M+H]$^+$): 681.6).

Molecule 18a: Product Obtained by the Reaction Between Molecule 17a and N-Boc ethylenediamine.

Using a process similar to that used for the preparation of molecule 16a applied to molecule 17a (7.09 g, 10.41 mmol) and to N-Boc ethylenediamine (1.83 g, 11.45 mmol), a white solid of molecule 18a is obtained after trituration in acetontrile Yield: 6.64 g (77%)

RMN $^1$H (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).

LC/MS (ESI): 824.0 (calculated ([M+H]$^+$): 823.7).

Molecule A8

Using a process similar to that used for the preparation of molecule A5a and applied to molecule 18a (3.00 g, 3.64 mmol), without basic washing, a beige solid of molecule A8 in the form of a hydrochloride salt is obtained after co-evaporation, 4 times, of the residue in methanol.

Yield: 2.66 g (96%)

RMN $^1$H (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).

LC/MS (ESI): 723.7 (calculated ([M+H]$^+$): 723.6).

Example A9: Molecule A9

Molecule 19a: Methyltetradecanoic-13 Acid

Magnesium chips (5.50 g, 226.3 mmol) is introduced into an oven-dried three-neck round-bottom flask under argon The magnesium is covered with anhydrous THF (25 mL) and several drops of 1-bromo-2-methylpropane are added at room temperature to initiate the reaction. After observing an exotherm and a slight turbidity of the medium, the rest of 1-bromo-2-methylpropane (28.42 g, 207 mmol) diluted with THF (60 mL) is added, drop-by-drop over 1 hour while the temperature of the medium remains stable from 65 to 70° C. The reaction medium is then heated by refluxing for 2 hours.

In a three-neck round-bottom flask under argon, to a solution of CuCl (280 mg, 2.83 mmol), dissolved in N-methylpyrrolidone (NMP) previously distilled at 0° C., is added, drop-by-drop, a solution of bromoundecanoïc-11 acid (25 g, 94.27 mmol) dissolved in THF (60 mL). Then, to this solution is added, drop-by-drop, the solution of organomagnesium, slightly hot, diluted in THF (50 mL) so as to maintain the temperature of the medium below 25° C. The mixture is then stirred at room temperature for 16 hours. The medium is cooled to 0° C. and the reaction is stopped by slow addition of an aqueous solution of 1 N HCl to pH 1 (300 mL) and the medium is extracted with hexane (100 mL) and ethyl acetate (2×75 mL). After washing the organic phase with an aqueous solution of 1 N HCl (100 mL), water (100 mL) and drying over Na$_2$SO$_4$, the solution is filtered and concentrated under vacuum, resulting in a brown solid. After purification by flash chromatography (cyclohexand, ethyl acetate), a white solid is obtained.

Yield: 18.1 g (79%)

RMN $^1$H (CDCl$_3$, ppm): 0.87 (6H); 1.11-1.18 (2H); 1.20-1.38 (16H); 1.51 (1H); 1.63 (2H); 2.35 (2H).

Molecule 20: Product Obtained by the Reaction Between Molecule 19a and L-Leucine.

To a solution of molecule 19a (18.05 g, 74.46 mmol) in THF (745 mL) at room temperature are successively added DCC (14.63 g, 70.92 mmol) and NHS (8.16 g, 70.92 mmol). After 40 hours of stirring at room temperature, the medium is cooled to 0° C. for 20 minutes, filtered on a sintered filter. L-leucine (9.77 g, 74.46 mmol), DIPEA (86 mL) and water (150 mL) are added to the filtrate. After 20 hours of stirring at room temperature, the medium is diluted with an aqueous solution saturated with NaHCO$_3$ (200 mL). The aqueous phase is washed with ethyl acetate (2×200 mL) and acidified with an aqueous solution of HCl 2 N to pH 1. The precipitate is filtered, rinsed thoroughly with water and dried under vacuum at 50° C. The solid is triturated 3 times in pentane, sonicated, then filtered, resulting in a white solid.

Yield: 18.8 g (75%)

RMN $^1$H (CDCl$_3$, ppm): 0.86 (6H); 0.96 (6H); 1.12-1.18 (2H); 1.20-1.78 (22H); 2.24 (2H); 4.58-4.63 (1H); 5.89 (1H).

LC/MS (ESI): 356.2 (calculated ([M+H]$^+$): 356.6).

Molecule 21a: Product Obtained by the Reaction Between Molecule 20 and Boc-tri(ethyleneglycol)diamine.

To a solution of molecule 20 (16.7 g, 46.97 mmol) in THF (235 mL) at room temperature are added DIPEA (20.3) and TBTU. After stirring for 20 minutes, the Boc-tri(ethyleneglycol)diamine (14 g, 56.36 mmol) is added. After stirring at room temperature for 5 hours, the mixture is concentrated under vacuum. The residue is removed with ethyl acetate (500 mL) washed with a saturated NaHCO$_3$ aqueous solution (3×200 mL), an aqueous solution of 1 N HCl (3×200 mL), and a saturated NaCl aqueous solution (3×200 mL). After drying over over Na$_2$SO$_4$, filtration and concentration under vacuum, the residue is purified by flash chromatography (cyclohexane, ethyl acetate, methanol), resulting in a colorless oil.

Yield: 23.5 g (85%)

RMN $^1$H (CDCl$_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

Using a process similar to that used for the preparation of molecule A5a, applied to molecule 21a (23.46 g, 40.04 mmol) without basic washing, the residue obtained after concentration under vacuum is triturated in an acetonitrile/acetone mixture. The supernatant is removed and the pasty residue is dried under vacuum. The residue is then triturated in acetone (150 mL) and the white solid of molecule A9 in the form of a hydrochloride salt is filtered, rinsed in acetone, then dried under vacuum.

Yield: 13.0 g (64%)

RMN $^1$H (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H). LC/MS (ESI): 486.4 (calculated ([M−]$^+$): 486.8).

Example A10: Molecule A10

Molecule 22a: Product Obtained by the Reaction Between Octanoyl Chloride and L-proline.

Using a process similar to that used for the preparation of molecule 11 and applied to octanoyl chloride (150.0 g, 0.922 mol) and to L-proline (212.3 g, 1.844 mol), a colorless oil of molecule 22a is obtained after washing the organic phase with a 10% HCl aqueous solution (3×300 mL), a saturated NaCl aqueous solution (300 mL), drying over $Na_2SO_4$, filtration through cotton, concentration under reduced pressure, then the residue is purified by flash chromatography (eluent: DCM, MeOH).

Yield: 134 g (60%)

RMN $^1$H ($CDCl_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1 (calculated ([M+H]$^+$): 242.2).

Molecule 23a: Product Obtained by the Coupling Between Molecule 22a and L-lysine.

To a solution of molecule 22a (132 g, 0.547 mol) in THF (924 mL) cooled to a temperature below 5° C. are successively added NHS (66.1 g, 0.574 mol) and DCC (118.5 g, 0.574 mol). After 21 hours of stirring, the precipitate is removed by precipitation and the filtrate is added over 30 minutes to a solution of L-lysine (41.98 g, 0.287 mol) in a mixture of deionized water (82 mL) DIPEA (476 mL, 2.735 mol) at 15° C. After 23 hours of stirring at room temperature, the reaction medium is concentrated under reduced pressure resulting in an oily residue which is diluted in water (1.3 L). The aqueous phase is washed twice with AcOEt (2×0.5 L), cooled to a temperature below 10° C., acidified by the addition of a solution of 6 N HCl (120 mL) to reach a pH of 1, then extracted 3 times with DCM (3×0.6 L). The organic phases are combined, washed with a saturated solution of NaCl (0.6 L), dried over $Na_2SO_4$ then concentrated under reduced pressure. The foam obtained is taken up with acetone (240 mL) under reflux for 2 hours. After a night at 10° C., pentane (240 mL) is added drop-by-drop. After 1 hour of stirring, the precipitate is recovered by filtration under vacuum, washed with a 1:1 mixture of pentane and acetone (150 mL), then dried under vacuum.

Yield: 83.9 g (52%)

RMN $^1$H ($CDCl_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5 (calculated ([M+H]$^+$): 593.4).

Molecule 24: Product Obtained by the Reaction Between Molecule 23a and L-lysine methyl ester.

To molecule 23a (76.26 g, 0.129 mol) are successively added HOPO (3.57 g, 32.1 mmol), dihydrochloride LysOMe (15.0 g, 64.3 mmol) and EDC (34.53 g, 0.18 mol) then DMF (600 mL) previously cooled to 5° C. is added. After dissolution, triethylamine (43.9 mL, 0.315 mol) is added drop-by-drop while maintaining the temperature below 5° C. for 2 hours after the end of the addition. After overnight at room temperature, the reaction medium is poured on a water/ice mixture (2 kg) and DCM (0.5 L). After 15 minutes of stirring, the phases are separated. The aqueous phase is extracted with DCM (2×0.4 L). The organic phases are combined, washed with a solution of 1N HCl (0.5 L) then with a saturated NaCl solution (0.5 L), dried over $Na_2SO_4$, concentrated under reduced pressure, then the residue is purified by flash chromatography (eluent: DCM, MeOH).

Yield: 56.7 g (67%)

RMN $^1$H ($CDCl_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated at 50° C. overnight. The reaction medium is then diluted with methyl-tetrahydrofuranne, then the organic phase is washed 4 times with a saturated NaCl solution (4×30 mL) then twice with water (2×50 mL) before being dried over $Na_2SO_4$ then concentrated under reduced pressure. The residue is solubilized in refluxing acetonitrile for 30 minutes, then the solution is cooled to room temperature while stirring overnight. The white precipitate is then recovered by filtration under vacuum, washed with cold acetonitrile (2×20 mL) then dried under vacuum.

Yield: 3.0 g (74%)

RMN $^1$H ($CDCl_3$, ppm): 0.87 (12H); 1.09-2.37 (84H); 2.74-4.56 (25H); 6.85-8.00 (7H).

LC/MS (ESI): 1338.0 (calculated ([M+H]$^+$): 1338.0).

Example A11: Molecule A11

Molecule A11 is obtained by the conventional method of peptide synthesis in solid phase (SPPS) on 2-chlorotrityle chloride (CTC) (40.0 g, 1.16 mmol/g) resin.

Grafting of the first Fmoc-Lys(Fmoc)-OH (1.5 equivalents) amino acid is performed in DCM (10V), in the presence of DIPEA (3.0 equivalents). Sites which did not react are capped with methanol (0.8 mL/g resin) at the end of the reaction.

The couplings of protected amino acids Fmoc-Glu(OtBu)-OH (2.5 equivalents), Fmoc-Pro-OH (2.5 equivalents) and myristic acid (2.5 equivalents) are carried out in DMF (10V), in the presence of HATU (2.5 equivalents) and DIPEA (3.7 equivalents).

The protective Fmoc groups are removed using a solution of 80:20 DMF/piperidine (10 V).

The product is cleaved from resin using a solution of 80:20 DCM/HFIP (10 V).

After concentration under reduced pressure, the residue is purified by chromatography on silica gel (dichloromethane, methanol).

Yield: 56.5 g (65%)

RMN $^1$H ($CD_3OD$, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+H]$^+$): 1894.2).

Example A12: Molecule A12

Molecule 25: Product Obtained by the Hydrogenation of Farnesol.

To a solution of farnesol (60.00 g, 269.82 mmol) in THF (1200 mL) under argon is added platinum oxide ($PtO_2$, 613 mg, 2.70 mmol) and the medium is placed under 1 atm of dihydrogen then stirred for 6 hours at room temperature. After filtration through celite and rinsing in THF, a black oil of molecule 25 is obtained after concentration under reduced pressure. This compound is used without additional purification.

Yield: 61.60 g (100%)

RMN $^1$H ($CDCl_3$, ppm): 0.85 (3H); 0.87 (6H); 0.90 (3H) 1.01-1.43 (15H); 1.47-1.66 (3H); 3.62-3.76 (2H).

Molecule 26: Product Obtained by the Oxidation of Molecule 25.

To a solution of molecule 25 (61.60 g, 269.68 mmol) in a dichloroethane/water (1350 mL/1080 mL) mixture are successively added tetrabutylammonium bromide (46.95 g, 145.63 mmol), acetic acid (416 mL, 7.28 mol) then $KMnO_4$ (127.85 g, 809.04 mmol) by small fractions while maintaining the temperature between 11 and 13° C. The reaction medium is then stirred for 4 hours 30 minutes, refluxing, cooled to 0° C. then acidified to pH 1 with a 37% HCl solution (50 mL). $Na_2SO_3$ (186.94 g) is added progressively while maintaining the temperature between 0 and 10° C. and the medium is stirred until it becomes completely colorless. The medium is acidified to pH 1 with a 37% HCl solution, then water (500 mL) and DCM (500 mL) are added. The phases are separated and the aqueous phase is extracted with DCM (2×500 mL). The combined organic phases are washed with an aqueous solution of 10% HCl (400 mL), water (2×400 mL), a saturated NaCl aqueous solution (400 mL), dried over $Na_2SO_4$, filtered and concentrated under reduced pressure. A yellow oil of molecule 26 is obtained after purification by flash chromatography (eluent: cyclohexane, AcOEt).

Yield: 54.79 g (84%)

RMN $^1$H (CDCl$_3$, ppm): 0.85 (3H); 0.87 (6H); 0.97 (3H); 1.03-1.43 (13H); 1.52 (1H); 1.91-2.01 (1H); 2.11-2.18 (1H); 2.32-2.39 (1H).

LC/MS (ESI−): 241.3 (calculated ([M−H]$^−$): 241.2).

Molecule 27: Product Obtained by the Coupling Between Molecule 26 and Methyl-L-prolinate.

To a solution of molecule 26 (54.70 g, 225.66 mmol) in DCM (1500 mL) at 0° C. are successively added HOBt (3.46 g, 22.57 mmol), DIPEA (117.92, 676.97 mmol), methyl L-prolinate hydrochloride (56.05 g, 338.49 mmol) then EDC (64.89 g, 338.49 mmol). The reaction mixture is stirred at 0° C. for 1 hour then at room temperature for 18 hours. The medium is then diluted with DCM (1000 mL), then washed by a saturated NaHCO$_3$ aqueous solution (2×1 L), a aqueous solution of 1 N HCl (2×1000 mL) and an aqueous solution of NaCl (2×1000 mL). The organic phase is dried over $Na_2SO_4$, filtered and concentrated under reduced pressure, resulting in a yellow oil of molecule 27 which is used without further purification.

Yield: 77.15 g (97%)

RMN $^1$H (DMSO-d$_6$, ppm): 0.79-0.89 (12H); 0.98-1.43 (13H); 1.51 (1H); 1.70-2.32 (7H); 3.33-3.42 (0.4H); 3.46-3.57 (1.6H); 3.59 (2.4H); 3.67 (0.6H); 4.23-4.32 (0.8H); 4.53-4.62 (0.2H).

LC/MS (ESI+): 354.2 (calculated ([M+H]$^+$): 354.3).

Molecule 28: Product Obtained by the Saponification of Molecule 27.

To a solution of molecule 27 (77.15 g, 218.22 mmol) in a mixture of THF/MeOH 1:1 (1454 mL) at 0° C. is added, drop-by-drop, a solution of LiOH (7.84 g, 327.33 mmol) in water (727 mL). The reaction mixture is stirred at 0° C. for 18 hours, then at room temperature for 5 hours. Organic solvents are evaporated under reduced pressure. Water (500 mL), an aqueous solution of 10% HCl (200 mL) and DCM (800 mL) are added and the phases are separated. The aqueous phase is extracted with DCM (2×1 L). The organic phases are combined, washed with water (500 mL), an aqueous solution of NaCl (500 mL), dried over $Na_2SO_4$, filtered and concentrated under reduced pressure, resulting in a yellow oil of molecule 28 which is used without further purification.

Yield: 71.72 g (97%)

RMN $^1$H (DMSO-d$_6$, ppm): 0.73-0.95 (12H); 0.95-1.42 (13H); 1.51 (1H); 1.65-2.32 (7H); 3.24-3.64 (2H); 4.13-4.28 (0.8H); 4.37-4.50 (0.2H); 12.44 (1H).

LC/MS (ESI+): 340.2 (calculated ([M+H]$^+$): 340.3).

Molecule A12

Molecule A12 is obtained by the conventional method of peptide synthesis in solid phase (SPPS) on 2-chlorotrityle chloride (CTC) (34.5 g, 1.16 mmol/g) resin.

Grafting of the diamine ethylene (10.0 equivalents) is carried out in DCM (10V), in the presence of DIPEA (10.0 equivalents). Sites which did not react are capped with methanol (0.8 mL/g resin) at the end of the reaction.

The couplings of protected amino acids Fmoc-Lys (Fmoc)-OH (1.5 equivalents), Fmoc-Glu(OMe)-OH (3.0 equivalents) and molecule 28 (3.0 equivalents) are carried out in a 1:1 DCM/DMF mixture (10V), in the presence of HATU (1.0 equivalent with respect with respect to the acid) and DIPEA (2.0 equivalents with respect to the acid).

The protective Fmoc groups are withdrawn using a solution of 80:20 DMF/piperidine (10 V) (after coupling with lysine) or a solution of morpholine at 50% in DMF (after coupling with glutamic acids).

The product is cleaved from resin using a solution of 50:50 DCM/TFA (10 V). After evaporation, the residue is solubilized in MeTHF (450 mL) and the organic phase is washed with a saturated NaHCO$_3$ aqueous solution (3×450 mL) and a saturated NaCl aqueous solution (200 mL). After drying over $Na_2SO_4$, the organic phase is filtered, concentrated under reduced pressure and the residue is purified by chromatography on silica gel (dichloromethane, methanol, NH4OH).

Yield: 13.95 g (31% in 7 steps).

RMN $^1$H (DMSO-d$_6$, ppm): 0.73-0.91 (24H); 0.96-2.41 (56H); 2.72 (2H); 2.89-3.10 (2H); 3.15-3.26 (2H); 3.26-3.51 (4H); 3.57 (3H); 3.58 (3H); 3.99-4.50 (5H) 6.07 (2H); 7.59-8.39 (5H).

LC/MS (ESI+): 1118.2 (calculated ([M+H]$^+$): 1117.8).

Example A13: Molecule A13

Molecule 29: Product Obtained by Polymerization of γ-benzyl-L-glutamate N-carboxyanhydride Initiated by N-Boc-ethylenediamine.

In a reactor, γ-benzyl-L-glutamate N-carboxyanhydride (39.44 g, 149.82 mmol) is solubilized in DMF (81 mL) at 25° C. The mixture is then stirred until complete dissolved, cooled to −10° C., then a solution of BocEDA (6.00 g, 37.45 mmol) in DMF (7 mL) is introduced rapidly. The reaction medium is stirred at 0° C. for 3 hours, then a solution of HCl in 1.4 dioxane (3.33 M, 11.8 mL, 39.29 mmol) is added. The reaction medium is stirred at room temperature, then poured an MeOH/IPE solution (125 mL/495 mL) cooled with an ice bath. After 65 hours of stirring at room temperature, the precipitate is filtered on sintered filtered, washed with IPE (2×90 mL) and dried at 30° C. under reduced pressure.

Yield: 21.71 g (54%)

DP (estimated according to RMN $^1$H): 4.9

The average calculated molar mass of molecule 29 in the form of a hydrochloride salt is 1270.9 g/mol.

RMN $^1$H (DMSO-d6, ppm): 1.35 (9H); 1.72-2.09 (9.8H); 2.23-2.60 (9.8H); 2.86-3.19 (4H); 3.85 (1H); 4.14-4.52 (3.9H); 4.86-5.23 (9.8H); 6.33-6.85 (1H); 7.09-7.55 (24.5H); 7.88-8.42 (6.9H); 8.67 (1H).

Molecule 30: Product Obtained by the Coupling Between Myristoyl Chloride and Molecule 29.

After solubilization of molecule 29 in the form of a hydrochloride sale (12.46 g, 9.80 mmol) in DCM (115 mL), the solution is cooled to 0° C. The following are then added in succession: triethylamine (2.35 g, 23.24 mmol) and a solution of myristoyl chloride (3.16 g, 12.79 mmol) in DCM (16 mL). The reaction medium is stirred at 0° C. for 4 h then at [room] temperature for 2 hours before being poured onto IPE (920 mL). After 14 hours of stirring at room temperature, the precipitate is filtered, washed with EtOH (2×145 ml, then 100 mL) and dried at 30° C. under reduced pressure.

Yield: 9.77 g (69%)

DP (estimated according to RMN $^1$H): 5.1

The average calculated molar mass of molecule 30 is 1488.7 g/mol.

RMN $^1$H (CDCl$_3$, ppm): 0.87 (3H); 1.07-1.51 (29H); 1.51-1.64 (2H); 1.80-2.75 (22.4H); 2.98-3.73 (4H); 3.84-4.50 (5.1H); 4.86-5.32 (10.2H); 5.71-6.47 (1H); 6.72-8.38 (31.6H).

Molecule A13

To a solution of molecule 30 (4.70 g, 3.16 mmol) in DCM (31 mL) at 0° C. is added TFA (31 mL). The reaction medium is stirred at 0° C. for 2 hours then concentrated under reduced pressure and at room temperature. The residue is returned to DCM (100 mL), then dry concentrated under reduced pressure and at room temperature. The residue is solubilized in DCM (100 mL) and washed with an aqueous solution of carbonate buffer at pH=10.4 (326 mL, then 2×200 mL) then with an aqueous solution of HCl (0.1 N, 2×200 mL). The organic solution is dried over Na$_2$SO$_4$, filtered, then dry concentrated at 40° C. under reduced pressure.

Yield: 3.96 g (88%)

DP (estimated according to RMN $^1$H): 5.2

The average calculated molar mass of molecule A13 in the form of a hydrochloride salt is 1446.9 g/mol.

RMN $^1$H (TFA-d, ppm): 0.91 (3H); 1.17-1.47 (20H); 1.60-1.74 (2H); 1.99-2.78 (22.8H); 3.41-4.05 (4H); 4.62-4.83 (5.2H); 5.05-5.35 (10.4H); 6.99-8.02 (26H).

Example A14: Molecule A14

Molecule 31: Product Obtained by the Reaction Between Molecule 14 and Boc-ethylenediamine.

Using a process similar to that used for the preparation of molecule 10 and applied to molecule 14 (12.00 g, 40.35 mmol) and to BocEDA (7.76 g, 48.42 mmol), a colorless oil of molecule 31 is obtained and used without further purification.

Yield: 17.40 g (94%)

RMN $^1$H (CDCl$_3$, ppm): 0.86 (3H); 1.11-1.68 (18H); 1.41 (9H); 1.80-2.38 (6H); 3.06-3.35 (4H); 3.37-3.49 (1H); 3.51-3.73 (1H); 4.26-4.31 (0.1H); 4.45-4.52 (0.9H); 4.91-5.19 (1H); 6.97 (0.1H); 7.23 (0.9H).

LC/MS (ESI+): 440.4 (calculated ([M+H]$^+$): 440.3).

Molecule A14

Using a process similar to that used for the preparation of molecule A2 and applied to molecule 31 (8.85 g, 20.13 mmol), in solution in DCM, a white solid of molecule A14 is obtained after basic washing, concentration under reduced pressure, then recrystallization in acetontrile Yield: 6.53 g (96%)

RMN $^1$H (DMSO, ppm): 0.85 (3H); 1.07-1.56 (20H); 1.68-2.03 (4H); 2.09-2.29 (2H); 2.50-2.58 (2H); 2.96-3.11 (2H); 3.21-3.59 (2H); 4.17-4.21 (0.65H); 4.25-4.29 (0.35H); 7.68 (0.65H); 8.00 (0.35H)

LC/MS (ESI): 340.3 (calculated ([M+H]$^+$): 340.3). 0.3).

Examples A15: Molecule A15

Molecule A15 is obtained by the conventional method of peptide synthesis in solid phase (SPPS) on 2-chlorotrityle chloride (CTC) (16.0 g, 1.16 mmol/g) resin.

Grafting of the diamine ethylene (20.0 equivalents) is performed in DCM (10V). Sites which did not react are capped with methanol (0.8 mL/g resin) at the end of the reaction.

The couplings of protected amino acids Fmoc-Lys (Fmoc)-OH (3.0 equivalents), Fmoc-Glu(OBn)-OH (4.0 equivalents) and molecule 11 (3.0 equivalents) are done in a DCM (10V) (Lys and molecule 11 couplings), or a 1:1 DCM/DMF mixture (10V), in the presence of HATU (1.0 equivalent with respect to the acid) and DIPEA mixture (1.5 equivalents with respect to the acid).

The protective Fmoc groups are removed using a solution of 80:20 DMF/piperidine (10 V) (after coupling with lysine) or a solution of DBU at 1% in DMF (after coupling with glutamic acids)

The product is cleaved from resin using a solution of 50:50 DCM/TFA (10 V). After concentration, the residue is solubilized in ethyl acetate (400 mL) and the organic phase is washed with an aqueous solution of carbonate buffer at pH 10 (1 M) (2×400 mL), then a saturated NaCl aqueous solution (400 mL). After drying over Na$_2$SO$_4$, the organic phase is filtered, concentrated under reduced pressure and the residue is purified by chromatography on silica gel (dichloromethane, methanol, NH4OH), then by recrystallization in acetonitrile.

Yield: 16.20 g (70% in 7 steps).

RMN $^1$H (DMSO-d$_6$, ppm): 0.85 (6H); 1.11-2.57 (72H); 2.50-5.57 (2H); 2.90-3.08 (4H); 3.36-3.61 (4H); 4.06-4.43 (5H); 5.08 (4H); 7.27-7.40 (10H); 7.51-8.31 (5H).

LC/MS (ESI+): 1242.0 (calculated ([M+H]$^+$): 1241.9).

Example A16: Molecule A16

Molecule 32: Product Obtained by SPPS

Molecule 32 is obtained by the conventional method of peptide synthesis in solid phase (SPPS) on 2-chlorotrityle chloride (CTC) (50.0 g, 1.14 mmol/g) resin.

Grafting of the first Fmoc-Glu(OtBu)-OH (1.3 equivalents) amino acid is performed in DCM (10V), in the presence of DIPEA (2.6 equivalents). Sites which did not react are capped with methanol (0.8 mL/g resin) at the end of the reaction.

The couplings of protected amino acids Fmoc-Glu(OtBu)-OH (1.3 equivalents), and molecule 11 (3.0 equivalents) are done in a DMF (10V), in the presence of HATU (1.0 equivalent with respect to the acid) and DIPEA (1.5 equivalents with respect to the acid).

The protective Fmoc groups are withdrawn using a solution of 80:20 DMF/piperidine (10 V).

The product is cleaved from resin using a solution of 80:20 DCM/HFIP (10 V).

After concentration under reduced pressure, the residue is purified by triruration in diisopropylether.

Yield: 35.78 g (90%)

RMN $^1$H (CDCl$_3$, ppm): 0.88 (3H); 1.19-1.35 (20H); 1.43 (9H); 1.44 (9H); 1.55-1.67 (2H); 1.90-2.46 (14H); 3.46-3.54 (1H); 3.63-3.71 (1H); 4.33-4.40 (1H); 4.43-4.52 (2H) 7.35 (0.05H); 7.40 (0.05H); 7.63 (0.95H); 7.94 (0.95H).

LC/MS (ESI+): 696.4 (calculated ([M+H]$^+$): 696.5).

Molecule 33: Product Obtained by the Reaction Between Molecule 32 and N-CBz ethylenediamine Using a process similar to that used for the preparation of molecule 7 and applied to molecule 32 (30.0 g, 43.11 mmol) and to N-CBz ethylenediamine hydrochloride (CBzEDA•HCl, 11.93 g, 51.73 mmol), and in the presence of DIPEA (15.0 mL, 86.22 mmol) a beige solid of molecule 33 is obtained. It is used without additional purification.

Yield: 37.6 g (100%)

RMN $^1$H (CDCl$_3$, ppm): 0.88 (3H); 1.19-1.34 (20H); 1.42 (9H); 1.44 (9H); 1.52-2.54 (16H); 3.16-3.70 (6H); 4.08-4.15 (1H); 4.19-4.25 (1H); 4.43-4.53 (1H); 5.00 (1H); 5.08 (1H); 6.56 (1H); 7.00 (1H); 7.24-7.37 (5H); 7.59 (1H); 8.41 (1H).

LC/MS (ESI+): 872.5 (calculated ([M+H]$^+$): 872.6).

Molecule A16

To a solution of molecule 33 (37.6 g, 43.11 mmol) in methanol (376 mL) is added Pd/Al2O3 (3.76 g) under an atmosphere of argon. The mixture is placed under a hydrogen atmosphere (7 bar) and stirred at room temperature for 72 hours. After P4 filtration of the catalyst on P4 filter, then through an Omnipore 0.2 μm PTFE hydrophilic membrane, the filtrate is evaporated under reduced pressure, resulting in molecule A16 in the form of a sticky oil.

Yield: 31.06 g (98%)

RMN $^1$H (CDCl$_3$, ppm): 0.88 (3H); 1.19-1.35 (20H); 1.43 (9H); 1.46 (9H); 1.56-1.67 (2H); 1.92-2.12 (6H); 2.24-2.54 (8H); 2.71 (2H); 2.90 (2H); 3.22-3.32 (1H); 3.42-3.51 (1H); 3.55-3.64 (1H); 3.73-3.81 (1H); 4.13-4.21 (1H); 4.26-4.33 (1H); 4.39-4.48 (1H); 7.10 (1H); 7.71 (1H); 8.45 (1H).

LC/MS (ESI+): 738.5 (calculated ([M+H]$^+$): 738.5).

Molecule A17

Molecule A17 is obtained by the conventional method of peptide synthesis in solid phase (SPPS) on 2-chlorotrityl chloride (CTC) (64.66 g, 1.16 mmol/g) resin.

Grafting of the diamine ethylene (10.0 equivalents) is performed in DCM (10V), in the presence of DIPEA (10.0 equivalents). Sites which did not react are capped with methanol (0.8 mL/g resin) at the end of the reaction.

The couplings of protected amino acids Fmoc-Glu (OtBu)-OH (1.5 equivalents), and molecule 28 (1.5 equivalents) are done in a 1:1 DCM/DMF (10V) mixture for the coupling of glutamic acid, or in DMF (10V), for the coupling of molecule 28, in the presence of HATU (1.0 equivalent with respect to the acid) and DIPEA (2.0 equivalents with respect to the acid).

The protective Fmoc groups are removed using a solution of 50:50 DMF/morpholine (10 V).

The product is cleaved from resin using a solution of 50:50 DCM/TFA (10 V). After evaporation, the residue is solubilized in MeTHF (500 mL) and the organic phase is washed with a 5% aqueous solution of Na2CO3 (3×250 mL), then the aqueous phases are extracted with MeTHF (1×150 mL). The combined organic phases are dried over Na$_2$SO$_4$ and filtered. A HCl solution in MeOH (1.25 M) is added, then the medium is concentrated under reduced pressure. The residue is purified on silica gel (dichloromethane, methanol), resulting in the hydrochloride salt of molecule A17 in the form of a light brown solid.

Yield: 12.48 g (30% in 5 steps).

RMN $^1$H (DMSO-d$_6$, ppm): 0.76-0.90 (12H); 0.97-1.41 (13H); 1.45-1.55 (1H); 1.68-2.40 (11H); 2.77-2.92 (2H); 3.20-3.64 (4H); 3.57 (3H); 4.15-4.49 (2H); 7.90-8.48 (5H).

LC/MS (ESI+): 525.5 (calculated ([M+H]$^+$): 525.4).

Example A18: Molecule A18

Molecule 34: Product Obtained by the Hydrogenation of Phytol.

To a solution of phytol (260.00 g, 878.78 mmol) in ethanol (1.25 L) under argon is added Raney Nickel at 50% in water (30.75 g, 175.36 mmol). The medium is placed under 1 bar of dihydrogen, then stirred for 8 hours at room temperature. After filtration on a pad of celite/silica/celite and rinsing in ethanol, a colorless oil of molecule 34 is obtained after concentration under reduced pressure.

Yield: 261.40 g (quant.)

RMN $^1$H (CDCl$_3$, ppm): 0.84 (6H); 0.86 (6H); 0.89 (3H) 1.00-1.46 (22H); 1.46-1.68 (3H); 3.61-3.73 (2H).

Molecule 35: Product Obtained by the Oxidation of Molecule 34.

Using a process similar to that used for the preparation of molecule 26 applied to molecule 34 (29.00 g, 97.13 mmol), a yellow oil of molecule 35 is obtained.

Yield: 28.70 g (94%)

RMN $^1$H (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^+$): 311.3).

Molecule 36: Product Obtained by the Coupling Between Molecule 35 and methyl-L-prolinate.

Using a process similar to that used for the preparation of molecule 27 applied to molecule 35 (18.00 g, 57.59 mmol), and to methyl-L-prolinate (14.31 g, 86.39 mmol), a yellow oil of molecule 36 is obtained.

Yield: 23.20 g (95%)

RMN $^1$H (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 37: Product Obtained by the Saponification of Molecule 36.

Using a process similar to that used for the preparation of molecule 28 applied to molecule 36 (21.05 g, 49.68 mmol), a yellow oil of molecule 37 is obtained.

Yield: 20.40 g (99%)

RMN $^1$H (DMSO-d$_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule A18

Molecule A18 is obtained by the conventional method of peptide synthesis in solid phase (SPPS) on 2-chlorotrityl chloride (CTC) (26.72 g, 1.16 mmol/g) resin.

Using a process similar to that used for the preparation of molecule A17, applied to 4,7,10-trioxa-1,13-tridecanediamine (TOTA, 68.30 g, 310.0 mmol), to Fmoc-Glu(OMe)-OH (23.77 mmol, 62.00 mmol) and to molecule 37 (19.04 g, 46.50 mmol), a yellow oil of molecule A18 in hydrochloride form is obtained.

Yield: 5.53 g (23% in 5 steps).

RMN $^1$H (DMSO-d$_6$, ppm): 0.76-0.89 (15H); 0.97-2.38 (36H); 2.77-2.87 (2H); 3.00-3.17 (3H); 3.32-3.54 (13H); 3.57 (3H); 4.09-4.18 (0.75H); 4.20-4.29 (1H); 4.39-4.47 (0.25H); 7.63-8.36 (5H).

LC/MS (ESI+): 755.7 (calculated ([M+H]$^+$): 755.6).

Examples A19: Molecule A19

Molecule A19 is synthesized in the same way as molecule A16, by using molecule 14 instead of molecule 11 during the SPPS stage.

Overall yield (3 stages): 32.6 g (81%)

RMN $^1$H (CDCl$_3$, ppm): 0.88 (3H); 1.20-1.35 (16H); 1.43 (9H); 1.46 (9H); 1.56-1.68 (2H); 1.93-2.11 (6H); 2.24-2.55 (10H); 2.85 (2H); 3.19-3.29 (1H); 3.38-3.48 (1H); 3.55-3.64 (1H) 3.74-3.82 (1H); 4.14-4.21 (1H); 4.25-4.32 (1H); 4.41-4.50 (1H); 7.03 (1H); 7.69 (1H); 8.42 (1H).

LC/MS (ESI): 710.4 (calculated ([M+H]$^+$): 710.5).

Example A20: Molecule A20

Molecule A20 is obtained by the conventional method of peptide synthesis in solid phase (SPPS) on 2-chlorotrityl chloride (CTC) (40.00 g, 1.16 mmol/g) resin.

Grafting of the diamine ethylene (20.0 equivalents) is performed in DCM (10V). Sites which did not react are capped with methanol (0.8 mL/g resin) at the end of the reaction.

The couplings of protected amino acids Fmoc-Lys (Fmoc)-OH (1.5 equivalents), Fmoc-Glu(OtBu)-OH (2.5 equivalents) and molecule 11 (2.5 equivalents) are carried out in DMF (10 V), in the presence of HATU (1.0 equivalent with respect to the acid) and DIPEA (1.5 equivalents with respect to the acid).

The protective Fmoc groups are removed using a solution of 80:20 DMF/piperidine (10 V).

The product is cleaved from resin using a solution of 50:50 DCM/TFA (10 V). After evaporation, the residue is solubilized in water (600 mL), the pH of the solution is adjusted to 7 by the addition of a solution of NaOH 5 N, then the product is lyophilized. The lyophilisate is purified by column chromatography on silica gel (dichloromethane, methanol, NH4OH), resulting in molecule A20 in the form of a white solid.

Yield: 24.6 g (50% in 7 steps).

RMN $^1$H (MeOD-d4, ppm): 0.90 (6H); 1.18-2.45 (68H); 2.45-2.60 (2H); 3.05-3.11 (2H); 3.11-3.19 (1H); 3.23-3.33 (1H); 3.43-3.66 (4H); 3.82-3.94 (2H); 4.10-4.51 (5H).

LC/MS (ESI+): 1061.9 (calculated ([M+H]$^+$): 1061.8).

PART B—SYNTHESIS OF THE HYDROPHOBIC CO-POLYAMINO ACIDS i) Co-Polyamino Acids According to Formulas XXX, XXXa, XXXb

| No. | CO-POLYAMINO ACIDS BEARING CARBOXYLATE CHARGES AND HYDROPHOBIC RADICALS |
|---|---|
| B1 | 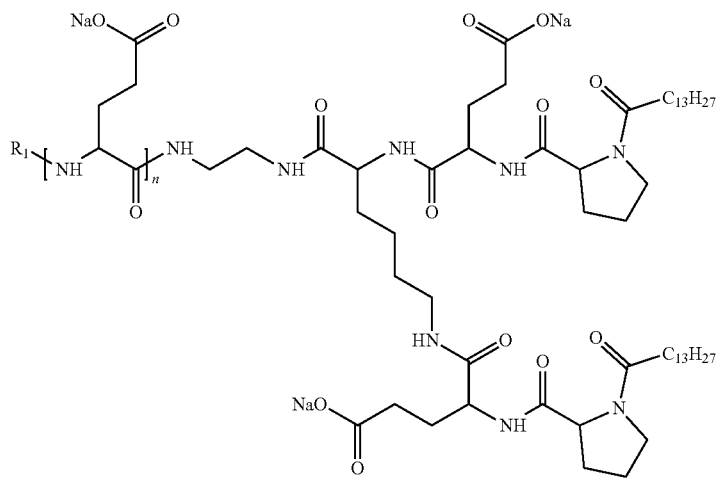<br>i = 0.038, DP = 26<br>$R_1$ = H or pyroglutamate |
| B2 | 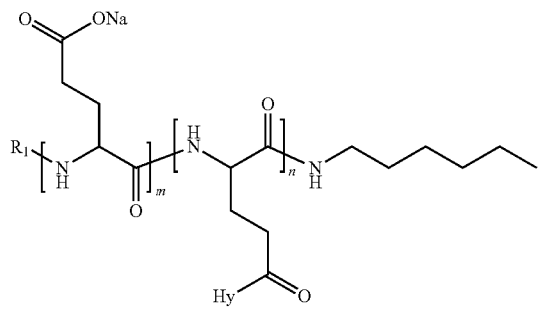<br>i = 0.15, DP (m + n) = 40 |

-continued
| No. | CO-POLYAMINO ACIDS BEARING CARBOXYLATE CHARGES AND HYDROPHOBIC RADICALS |
|---|---|
| | 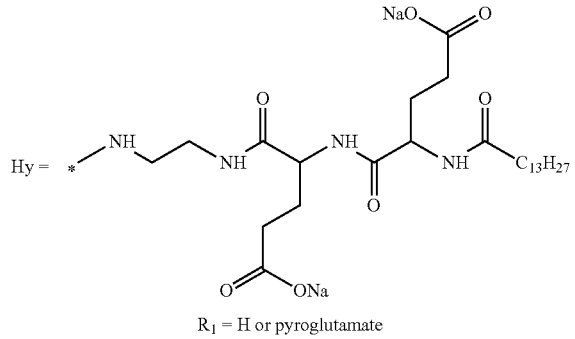
$R_1$ = H or pyroglutamate |
| B3 | 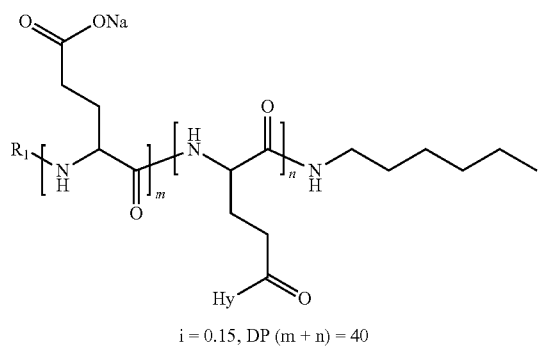
i = 0.15, DP (m + n) = 40
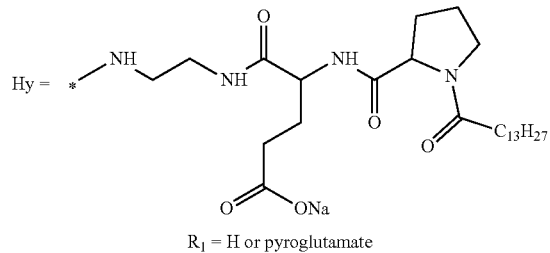
$R_1$ = H or pyroglutamate |
| B4 | 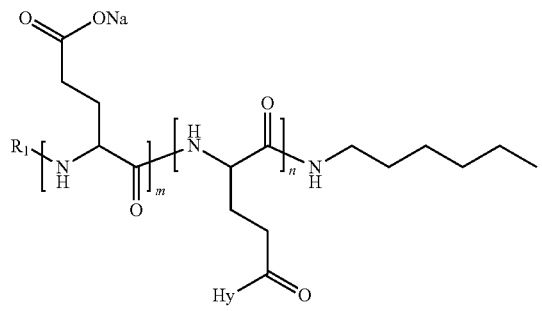
i = 0.15, DP (m + n) = 40
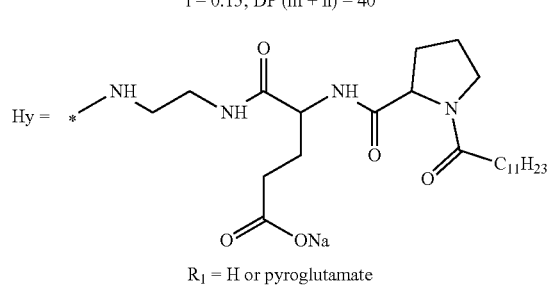
$R_1$ = H or pyroglutamate |

-continued
| No. | CO-POLYAMINO ACIDS BEARING CARBOXYLATE CHARGES AND HYDROPHOBIC RADICALS |
|---|---|
| B5 | 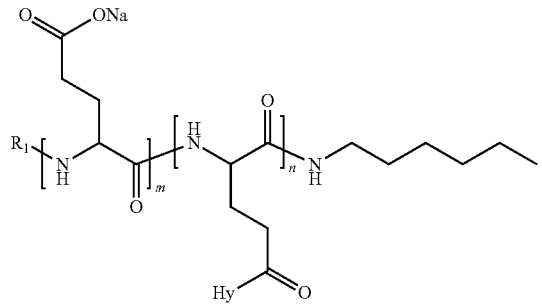<br>i = 0.15, DP (m + n) = 40<br>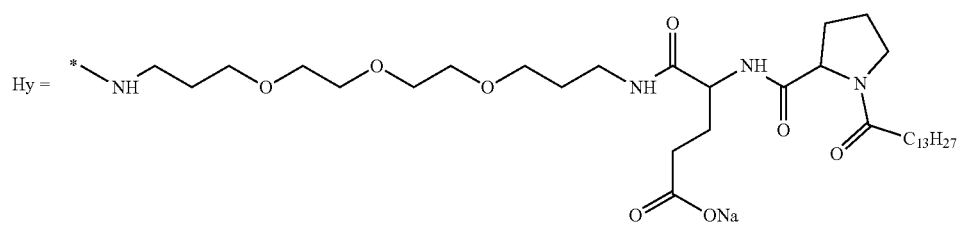<br>$R_1$ = H or pyroglutamate |
| B7 | 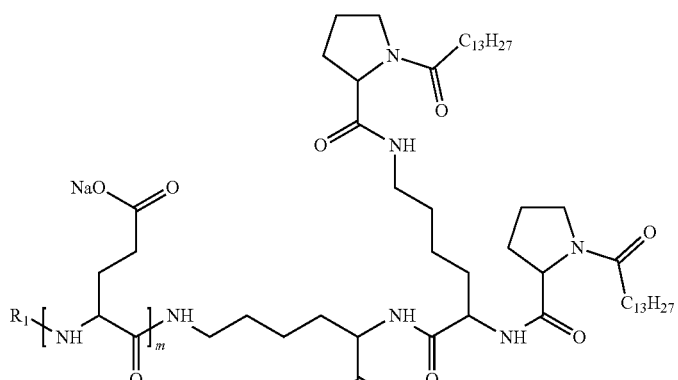<br>i = 0.038, DP = 26<br>$R_1$ = H or pyroglutamate |
| B13 | 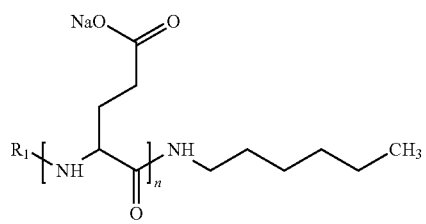<br>i = 0.042, DP = 24 |

-continued
| No. | CO-POLYAMINO ACIDS BEARING CARBOXYLATE CHARGES AND HYDROPHOBIC RADICALS |
|---|---|
| | 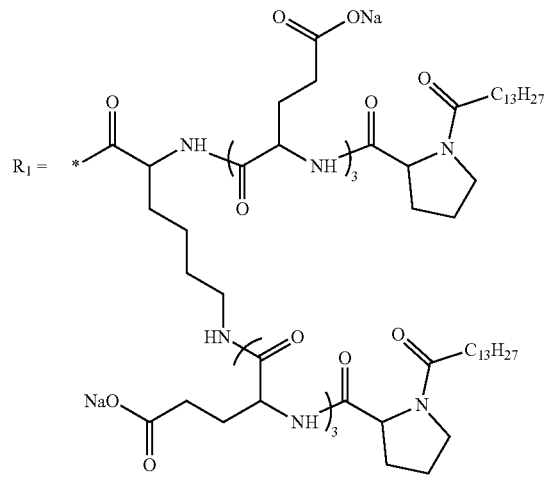 |
| B14 | 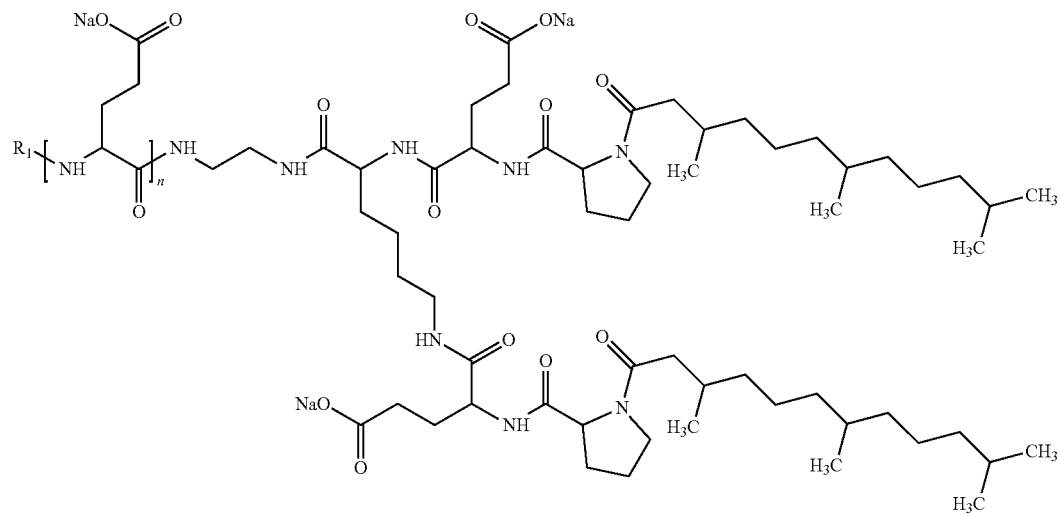<br>$i = 0.042$, DP = 24<br>$R_1$ = H or pyroglutamate |
| B15 | 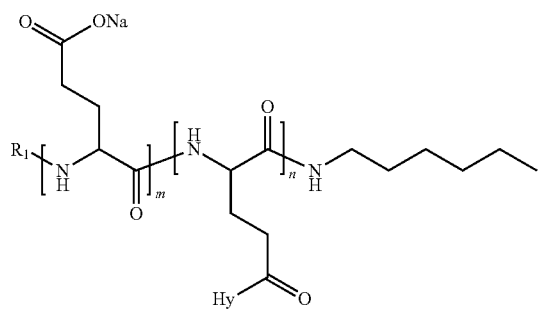<br>$i = 0.15$, DP $(m + n) = 40$ |

| No. | CO-POLYAMINO ACIDS BEARING CARBOXYLATE CHARGES AND HYDROPHOBIC RADICALS |
|---|---|
| | 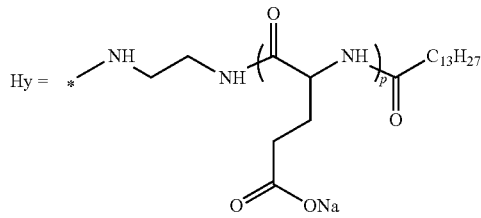 DP (p) = 5.2<br>$R_1$ = H or pyroglutamate |
| B17 | 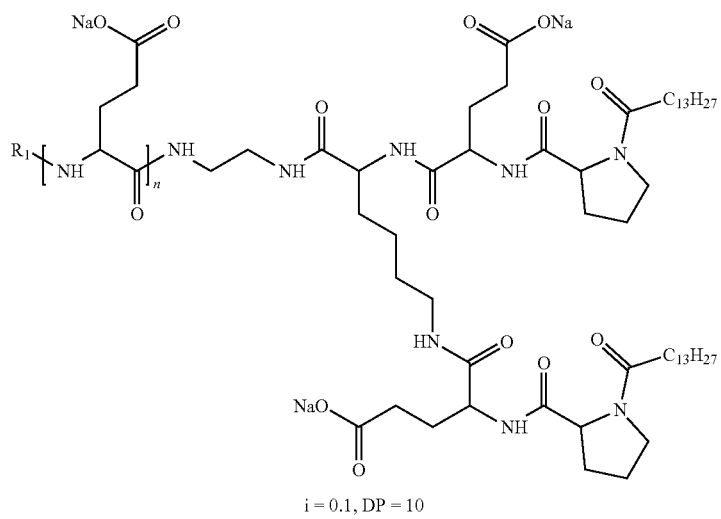 i = 0.1, DP = 10<br>$R_1$ = H or pyroglutamate |
| B18 | 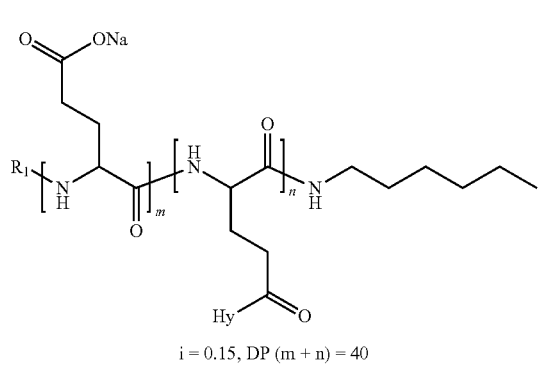 i = 0.15, DP (m + n) = 40 |
| | 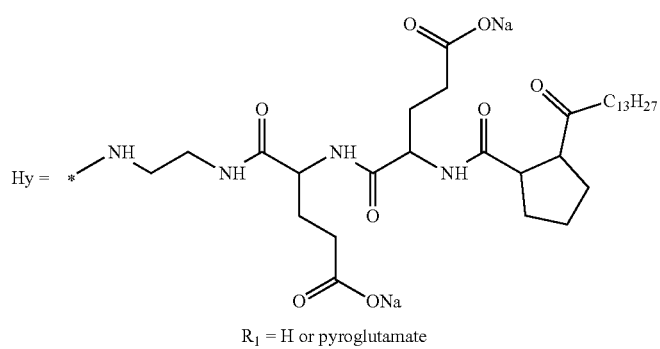 $R_1$ = H or pyroglutamate |

| No. | CO-POLYAMINO ACIDS BEARING CARBOXYLATE CHARGES AND HYDROPHOBIC RADICALS |
|---|---|
| B19 | 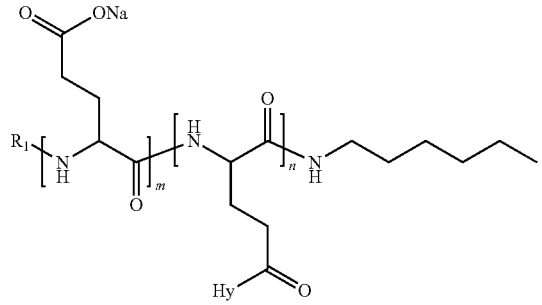<br>i = 0.15, DP (m + n) = 40<br>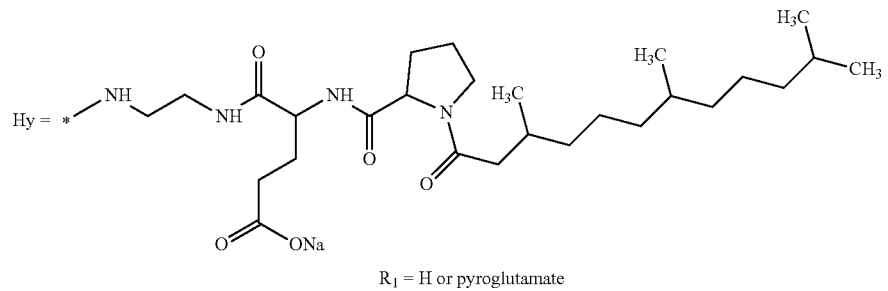<br>R₁ = H or pyroglutamate |
| B20 | 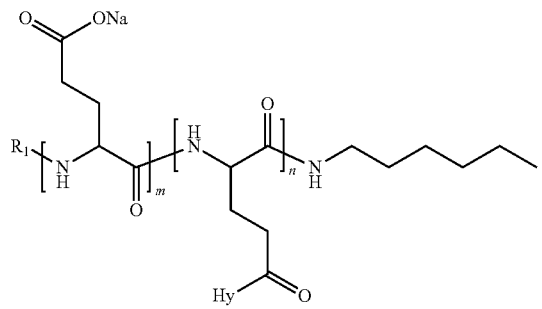<br>i = 0.15, DP (m + n) = 40<br>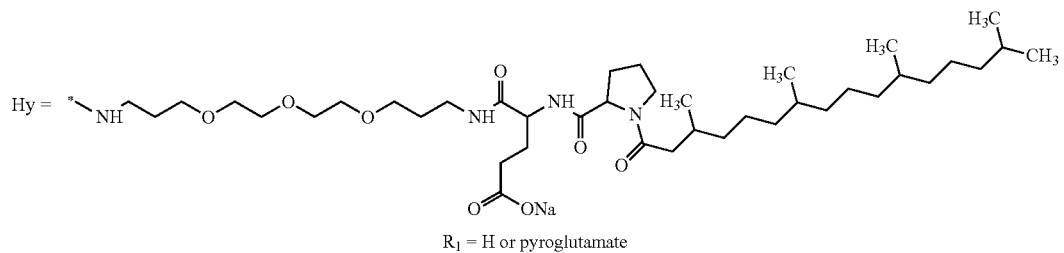<br>R₁ = H or pyroglutamate |

| No. | CO-POLYAMINO ACIDS BEARING CARBOXYLATE CHARGES AND HYDROPHOBIC RADICALS |
|---|---|
| B21 | 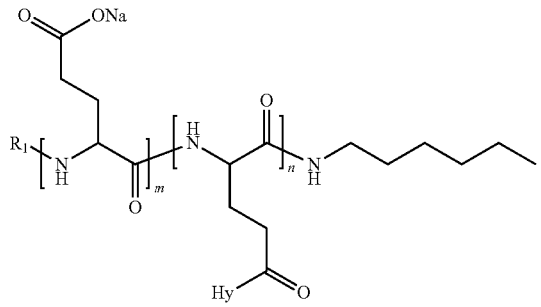 i = 0.15, DP (m + n) = 40 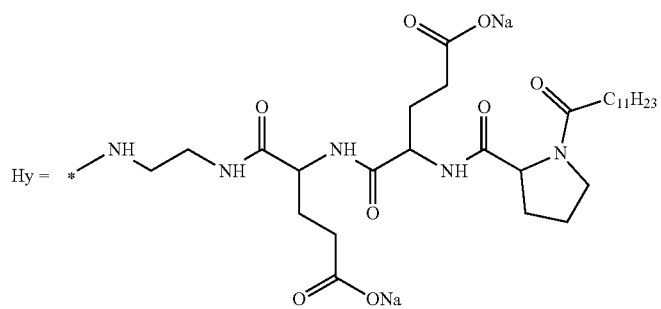 $R_1$ = H or pyroglutamate |
| B22 | 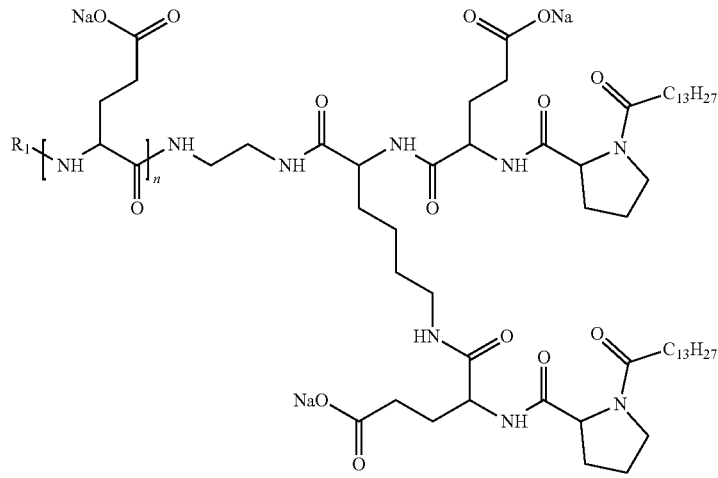 i = 0.5, DP = 20 $R_1$ = H or pyroglutamate |

Co-Polyamino Acid B1: Sodium poly-L-glutamate Modified at One of its Extremities by Molecule A1 and Having a Number Average Molar Mass (Mn) of 2800 g/mol In a previously oven-dried flask, γ-benzyl-L-glutamate N-carboxyanhydride (8.95 g, 34 mmol) is solubilized in anhydrous DMF (34 mL). The mixture is cooled to 4° C., then a solution of molecule A1 (1.64 g, 1.55 mmol) in chloroform (6.6 mL) is quickly introduced. The mixture is stirred between 4° C. and room temperature for 68 hours, then heated to 65° C. for 2 hours. Half of the solvent is distilled under reduced pressure, then the reaction medium is cooled to room temperature and poured drop-by-drop into diisopropylether (300 mL) while stirring. The white precipitate is recovered by filtration, washed with diisopropylether (5×50 mL), then dried under reduced pressure at 30° C. in order to obtain a white solid. The solid (7.9 g) is diluted in TFA (30 mL), and a solution of 33% hydrobromic acid (HBr) in acetic acid (21 mL, 120 mmol) is then added, drop-by-drop, at 0° C. The solution is stirred for 2 hours at room temperature, then poured, drop-by-drop over a 1:1 mixture (v/v) of diisopropylether/water while stirring (360 mL). After stirring for 2 hours, the heterogeneous mixture is allowed to rest overnight. The white precipitate is recovered by filtration, washed successively with IPE (2×30 mL) then with water (2×30 mL). The solid obtained is solubilized in water (200 mL) while adjusting the pH to 7 by adding a 1

N aqueous soda solution. Water (65 mL) is added. The mixture is filtered through a 0.45 μm filter, then purified by ultrafiltration against a 0.9% NaCl solution, then by water until the conductimetry of the permeate is less than 50 μS/cm. The co-polyamino acid is then concentrated to about theoretical 25 g/L, the pH is adjusted to 7 and the aqueous solution is filtered by 0.2 μm. This solution is diluted with water and acetone in order to obtain a solution at 12 g/L containing 30% acetone by mass, then it is filtered by activated carbon filter (3M R53SLP). The acetone is distilled (40° C., 100 mbar) and the solution is purified by ultrafiltration against a 0.9% NaCl solution, then water, until the conductrimetry of the permeate is less than 50 μS/cm. The co-polyamino acid solution is then concentrated and the pH is adjusted to 7. The aqueous solution is filtered through 0.2 μm and stored at 4° C.

Dry extract: 17.8 mg/g
DP (estimated according to RMN $^1$H): 26
According to RMN $^1$H: i=0.038

The average calculated molar mass of Co-polyamino acid B1 is 4994 g/mol.

Organic HPLC-SEC (PEG calibrating): Mn=2800 g/mol
Co-Polyamino Acid B2: Sodium poly-L-glutamate Modified by Molecule A2, the Esters of which are Saponified and Having a Number Average Molar Mass (Mn) of 5200 g/mol Co-polyamino acid B2-1: poly-L-glutamic acid resulting from the polymerization of γ-benzyl-L-glutamate N-carboxyanhydride initiated by hexylamine In a jacketed reactor, γ-benzyl-L-glutamate N-carboxyanhydride (500 g, 1.90 mol) is solubilized in anhydrous DMF (1100 mL). The mixture is then stirred until completely dissolved, cooled to 0° C., then hexylamine (6.27 mL, 47.5 mmol) is quickly introduced. The mixture is stirred at 0° C. for 5 h, between 0° C. and 20° C. for 7 h, then at 20° C. for 7 h. The reaction medium is then heated to 65° C. for 2 h, cooled to 55° C. and methanol (3300 mL) is introduced over 1 h 30. The reaction mixture is then cooled to 0° C. and stirred for 18 hours. The white precipitate is recovered by filtration, washed with diisopropylether (2×800 mL) then dried under reduced pressure at 30° C. resulting in a poly (gamma-benzyl-L-glutamic) acid (PBLG).

To a solution of PBLG (180 g) in N,N-dimethylacetamide (DMAc, 450 mL) is added Pd/Al$_2$O$_3$ (36 g) under an argon atmosphere. The mixture is placed under a hydrogen atmosphere (10 bar) and stirred at 60° C. for 24 hours. After cooling to room temperature and Filtration of the catalyst on sintered P4, then filtration through Omnipore 0.2 μm PTFE hydrophilic membrane, a solution of water at pH 2 (2700 mL) is dripped drop-by-drop on the DMAc solution, over a period of 45 minutes and while stirring. After 18 hours of stirring, the white precipitate is recovered by filtration, washed with water (4×225 mL), then dried under reduced pressure at 30° C.

Co-Polyamino Acid B2

Co-polyamino acid B2-1 (15.0 g) is solubilized in DMF (230 mL) at 40° C., then N-methylmorpholine (NMM, 11.57 g, 114.4 mmol) is added. At the same time, molecule A2 in the form of a hydrochloride salt (10.17 g, 17.2 mmol) is put into suspension in DMF (250 mL) and triethylamine (2.39 mL, 17.2 mmol) is added, then the mixture is slightly heated while stirring, until completely dissolved. To the co-polyamino acid solution, cooled to 25° C., are added, in succession, the solution of molecule A2, of N-oxide 2-hydroxypyridine (HOPO, 3.81 g, 34.3 mmol) then EDC (6.58 g, 34.3 mmol). The reaction medium is stirred at 25° C. for 2 h, filtered through a 0.2 mm fabric filter et and dripped drop-by-drop over 2.6 L of water containing 15% NaCl solution and HCl (pH 2) while stirring. At the end of the addition, the pH is readjusted to 2 with a solution of 1 N HCl, and the suspension is allowed to rest overnight. The precipitate is collected, then rinsed with 2×100 mL of water. The white solid obtained is solubilized in 1.2 L of water by the slow addition of an aqueous solution of 1 N NaOH until pH 7, while stirring, then the solution is filtered through a 0.45 μm filter. Ethanol (30% by mass) is added, then the solution is filtered through an activated carbon filter (3M R53SLP). The solution of 10 N NaOH is slowly added, while stirring, until pH 13, then the mixture is left stirring for 2 hours. After neutralization to pH 7 by the addition of a 37% HCl solution, the clear solution obtained is purified by ultrafiltration against a 0.9% solution of NaCl, then water, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 22.6 mg/g
DP (estimated according to RMN $^1$H): 40
According to RMN $^1$H: i=0.15

The average calculated molar mass of Co-polyamino acid B2 is 9301 g/mol.

Organic HPLC-SEC (PEG calibrating): Mn=5200 g/mol.
Co-Polyamino Acid B3: Sodium poly-L-glutamate Modified by Molecule A3, the Ester of which is Saponified and Having a Number Average Molar Mass (Mn) of 4900 g/mol Co-polyamino acid B2-1 (12.0 g) is solubilized in DMF (92 mL) at 40° C., then N-methylmorpholine (NMM, 9.25 g, 91.5 mmol) is added. At the same time, a solution of molecule A3 in the form of a hydrochloride salt (7.51 g, 13.7 mmol) and of N,N-diisopropylethylamine (DIPEA, 2.39 mL, 13.7 mmol) in DMF (27 mL) is prepared. To the co-polyamino acid solution, cooled to 25° C., are added, in succession, the solution of molecule A3, of N-oxide 2-hydroxypyridine (HOPO, 3.05 g, 27.4 mmol). The mixture is cooled to 0° C. then EDC (5.26 g, 27.4 mmol) is added. After 5 minutes at 0° C., the reaction medium is stirred at 25° C. for 2 h, filtered through a 0.2 mm fabric filter and dripped drop-by-drop over 950 mL of water containing 15% NaCl solution and HCl (pH 2) while stirring. At the end of the addition, the pH is readjusted to 2 with a solution of 1 N HCl, and the suspension is allowed to rest overnight. The precipitate is collected, then rinsed 3×100 mL of water. The solid obtained is solubilized in 1 L of water by the slow addition of an aqueous solution of NaOH 1 N until pH 7, while stirring. Once completely solubilized, the pH is adjusted to pH 12 over 2 hours then to pH 13 over 1 hour by the addition of a 10 N NaOH solution. After neutralization to pH 7 by the addition of a 37% HCl solution, this solution is diluted with water and ethanol in order to obtain a 12 g/L solution containing 30% ethanol by mass, then it is filtered through an activated carbon filter (3M R53 SLP). The solution is filtered through a 0.45 μm filter, then purified by ultrafiltration against a 0.9% NaCl solution, until the conductimetry of the permeate is less than 50 μS/cm. The co-polyamino acid solution is then concentrated and the pH is adjusted to 7. The aqueous solution is filtered through 0.2 μm and stored at 4° C.

Dry extract: 20.6 mg/g
DP (estimated according to RMN $^1$H): 40
According to RMN $^1$H: i=0.15

The average calculated molar mass of Co-polyamino acid B3 is 8977 g/mol.

Organic HPLC-SEC (PEG calibrating): Mn=4900 g/mol.

Co-Polyamino Acid B4: Sodium poly-L-glutamate Modified by Molecule A4, the Ester of which is Saponified and Having a Number Average Molar Mass (Mn) of 4700 g/mol Using a process similar to that used for the preparation of co-polyamino acid B3 applied to a hydrochloride salt of molecule A4 (7.12 g, 13.7 mmol) and to co-polyamino acid B2-1 (12.0 g), a sodium poly-L-glutamate modified by molecule A4 for which the ester is saponified is obtained.

Dry extract: 19.4 mg/g

DP (estimated according to RMN $^1$H): 40

According to RMN $^1$H: i=0.15

The average calculated molar mass of Co-polyamino acid B4 is 8809 g/mol.

Organic HPLC-SEC (PEG calibrating): Mn=4700 g/mol.

Co-Polyamino Acid B5: Sodium poly-L-glutamate Modified by Molecule A5, the Ester of which is Saponified and Having a Number Average Molar Mass (Mn) of 5400 g/mol Using a process similar to that used for the preparation of co-polyamino acid B3 applied to a hydrochloride salt of molecule A5 (9.71 g, 13.7 mmol) and to co-polyamino acid B2-1 (12.0 g), a sodium poly-L-glutamate modified by molecule A5 for which the ester is saponified is obtained.

Dry extract: 20.8 mg/g

DP (estimated according to RMN $^1$H): 40

According to RMN $^1$H: i=0.15

The average calculated molar mass of Co-polyamino acid B5 is 9939 g/mol.

Organic HPLC-SEC (PEG calibrating): Mn=5400 g/mol.

Co-Polyamino Acid B7: Sodium poly-L-glutamate Modified at One of its Extremities by Molecule A7 and Having a Number Average Molar Mass (Mn) of 2500 g/mol Using a process similar to that used for the preparation of co-polyamino acid B1 applied to molecule A7 (2.50 g, 2.74 mmol) and to γ-benzyl-L-glutamate N-carboxyanhydride (15.89 g, 60.4 mmol), a sodium poly-L-glutamate modified at one of its extremities by molecule A7 is obtained.

Dry extract: 20.3 mg/g

DP (estimated according to RMN $^1$H): 26

According to RMN $^1$H: i=0.038

The average calculated molar mass of Co-polyamino acid B7 is 3893 g/mol.

Organic HPLC-SEC (PEG calibrating): Mn=2500 g/mol

Co-Polyamino Acid B13: Sodium poly-L-glutamate Modified at One of its Extremities by Molecule A11 for which the Esters are Deprotected and Having a Number Average Molar Mass (Mn) of 3000 g/mol In a jacketed reactor, γ-benzyl-L-glutamate N-carboxyanhydride (24.50 g, 93.05 mmol) is solubilized in anhydrous DMF (55 mL). The mixture is then stirred until completely dissolved, cooled to 0° C., then hexylamine (0.56 mL, 4.23 mmol) is quickly introduced. The mixture is stirred at 0° C. for 48 h then the following are added in succession: a solution of molecule A11 (9 g, 5.08 mmol) in DMF (50 mL), HOPO (564 mg, 5.08 mmol) and EDC (973 mg, 5.08 mmol). The reaction medium is stirred at 0° C. for 1 h, between 0° C. and 20° C. for 2 h, then at 20° C. for 16 h. This solution is then run into a 1:1 H$_2$O/MeOH mixture (10 V) at room temperature while stirring. After 4 hours, the white precipitate is recovered by filtration, washed with diisopropyl ether (2×100 mL), water (2×100 mL) and a 1:1 H$_2$O/MeOH mixture (2×100 mL), then dried under reduced pressure.

The solid obtained is solubilized in TFA (220 mL) and stirred at room temperature for 2 hours 30 minutes. This solution is then poured in water (10V) at room temperature while stirring. After 2 hours 30 minutes of stirring, the white precipitate is recovered by filtration, washed with water (2×200 mL), then dried under reduced pressure.

The solid obtained is solubilized in N,N-dimethylacetamide (DMAc, 210 mL) is added Pd/Al$_2$O$_3$ (2.1 g) under an argon atmosphere. The mixture is placed under a hydrogen atmosphere (6 bar) and stirred at 60° C. for 24 hours. After cooling to room temperature and filtration of the catalyst on sintered P4, then filtration through Omnipore 0.2 µm PTFE hydrophilic membrane, a solution of water at pH 2 containing 15% NaCl (6 V) is dripped drop-by-drop on the DMAc solution, over a period of 45 minutes while stirring. After 18 hours of stirring, the white precipitate is recovered by filtration, washed with water, then dried under reduced pressure. The solid obtained is solubilized in water (600 mL) while adjusting the pH to 7 by the addition of a 1N aqueous soda solution. The pH is then adjusted to pH12 and the solution is stirred for 1 hour. After neutralization to pH 7, the solution is filtered through 0.2 µm, diluted with ethanol in order to obtain a solution containing 30% by mass of ethanol, then filtered through an activated carbon filter (3M R53 SLP). The solution is filtered through a 0.45 µm filter, then purified by ultrafiltration against a 0.9% NaCl solution, until the conductimetry of the permeate is less than 50 µS/cm. The co-polyamino acid solution is then concentrated and the pH is adjusted to 7. The aqueous solution is filtered through 0.2 µm and stored at 4° C.

Dry extract: 23.5 mg/g

DP (estimated by RMN $^1$H)=24 therefore i=0.042

The average calculated molar mass of Co-polyamino acid B13 is 5377 g/mol.

Organic HPLC-SEC (PEG calibrating): Mn=3000 g/mol.

Co-Polyamino Acid B14: Sodium poly-L-glutamate Modified at One of its Extremities by Molecule A12 for which the Esters are Deprotected and Having a Number Average Molar Mass (Mn) of 3300 g/mol Co-Polyamino Acid B14-1: poly-L-benzylglutamate Modified at One of its Extremities by Molecule A12.

In a previously oven-dried flask, γ-benzyl-L-glutamate N-carboxyanhydride (50.00 g, 189.39 mmol) is solubilized in anhydrous DMF (65 mL). The mixture then stirred until completely dissolved, cooled to 0° C., then a solution of molecule A12 (9.65 g, 8.63 mmol) in DMF (50 mL) is quickly introduced. The mixture is stirred from 0° C. to room temperature for 2 hours, then heated to 65° C. for 2 hours. The reaction medium is cooled to room temperature and poured drop-by-drop into diisopropylether (1.8 mL) while being stirred. The white precipitate is recovered by filtration, washed two times with diisopropylether, then dried under vacuum at 30° C. in order to obtain a white solid.

Co-Polyamino Acid B14

Co-polyamino acid B14-1 is solubilized in DMAc (250 mL) then Pd/Al$_2$O$_3$ (5.0 g) is added under an argon atmosphere. The mixture is placed under a hydrogen atmosphere (10 bar) and stirred at 60° C. for 24 hours. After cooling to room temperature and filtration of the catalyst on sintered P4, then filtration through Omnipore 0.2 µm PTFE hydrophilic membrane, a solution of water at pH 2 (6 V) is dripped drop-by-drop on the DMAc solution, over a period of 45 minutes while stirring. After 18 hours of stirring, the white precipitate is recovered by filtration, washed with water, then dried under reduced pressure. The solid obtained is solubilized in water (1.25 L) while adjusting the pH to 7 by the addition of a 1N aqueous soda solution. The pH is then adjusted to pH 13 and the solution is stirred for 3 hours. After neutralization to pH 7, the solution is filtered through 0.2 µm, diluted with ethanol in order to obtain a solution containing 30% by mass of ethanol, then filtered through an activated carbon filter (3M R53 SLP). The solution is filtered through a 0.45 µm filter, then purified by ultrafiltration against a 0.9% NaCl solution, until the conductimetry of the permeate is less than 50 µS/cm. The co-polyamino acid solution is then concentrated and the pH is adjusted to 7. The aqueous solution is filtered through 0.2 µm and stored at 4° C.

Dry extract: 25.7 mg/g
DP (estimated by RMN $^1$H)=24 therefore i=0.042
The average calculated molar mass of Co-polyamino acid B14 is 4720 g/mol.
Organic HPLC-SEC (PEG calibrating): Mn=3300 g/mol.
Co-Polyamino Acid B15: Sodium poly-L-glutamate Modified by Molecule A13 for which the Esters are Deprotected and Having a Number Average Molar Mass (Mn) of 4400 g/mol Using a process similar to that used for the preparation of co-polyamino acid B3 applied to a hydrochloride salt of molecule A13 (3.39 g, 2.34 mmol) and to co-polyamino acid B2-1 (2.04 g), with a saponification step at pH 13 for 5 hours in a mixture containing 30% by mass of ethanol, a sodium poly-L-glutamate modified by molecule A13 for which the esters are deprotected is obtained.

Dry extract: 15.7 mg/g
DP (estimated according to RMN $^1$H): 40
According to RMN $^1$H: i=0.15
The average calculated molar mass of Co-polyamino acid B15 is 12207 g/mol.
Organic HPLC-SEC (PEG calibrating): Mn=4400 g/mol.
Co-Polyamino acid B17: Sodium poly-L-glutamate Modified at One of its Extremities by Molecule A15 for which the Esters are Deprotected and Having a Number Average Molar Mass (Mn) of 1000 g/mol Using a process similar to that used for the preparation of co-polyamino acid B14 applied to molecule A15 (10.85 g, 8.74 mmol) and to γ-benzyl-L-glutamate N-carboxyanhydride (23.00 g, 87.37 mmol), with a saponification step at pH 12 for 2 hours, a sodium poly-L-glutamate modified at one of its extremities by molecule A15, for which the esters are deprotected is obtained.

Dry extract: 23.9 mg/g
DP (estimated according to RMN $^1$H): 10
According to RMN $^1$H: i=0.1
The average calculated molar mass of Co-polyamino acid B17 is 2576 g/mol.
Aqueous HPLC-SEC (PEG calibrating): Mn=1000 g/mol.
Co-Polyamino Acid B18: Sodium poly-L-glutamate Modified by Molecule A16 for which the Esters are Deprotected and Having a Number Average Molar Mass (Mn) of 5000 g/mol Using coupling similar to that used for the preparation of co-polyamino acid B3 applied to molecule A16 (31.06 g, 42.08 mmol) and to co-polyamino acid B2-1 (36.80 g), a beige solid id obtained after the acid precipitation step. This solid is diluted in TFA (100 g/L) and the mixture is stirred at room temperature for 3 hours. The solution is then dripped drop-by-drop over water (3V) while stirring. After 16 hours of stirring, the precipitate is recovered by filtration, then washed with water. The solid obtained is solubilized in water while adjusting the pH to 7 by the addition of a 10 N aqueous soda solution. Once solubilization is complete, the pH is adjusted to pH 12 over 1 hour by the addition of a 1N solution of NaOH. After neutralization to pH 7 by the addition of a solution of 1N HCl, the product is purified by a process similar to that used for the preparation of co-polyamino acid B3 (charcoal filtration and ultrafiltration). A sodium poly-L-glutamate modified by molecule A16 for which the esters are deprotected is obtained.

Dry extract: 28.2 mg/g
DP (estimated according to RMN $^1$H): 40
According to RMN $^1$H: i=0.15
The average calculated molar mass of Co-polyamino acid B18 is 9884 g/mol.
Organic HPLC-SEC (PEG calibrating): Mn=5000 g/mol.
Co-Polyamino Acid B19: Sodium poly-L-glutamate Modified by Molecule A17 for which the Esters are Deprotected and Having a Number Average Molar Mass (Mn) of 4900 g/mol Using a process similar to that used for the preparation of co-polyamino acid B3 applied to a hydrochloride salt of molecule A17 (7.35 g, 13.09 mmol) and to co-polyamino acid B2-1 (11.45 g), with a saponification step at pH 13 for 3 hours in a mixture containing 30% by mass of ethanol, a sodium poly-L-glutamate modified by molecule A17 for which the esters are deprotected is obtained.

Dry extract: 25.7 mg/g
DP (estimated according to RMN $^1$H): 40
According to RMN $^1$H: i=0.15
The average calculated molar mass of Co-polyamino acid B19 is 9062 g/mol.
Organic HPLC-SEC (PEG calibrating): Mn=4900 g/mol.
Co-Polyamino Acid B20: Sodium poly-L-glutamate Modified by Molecule A18 for which the Esters are Deprotected and Having a Number Average Molar Mass (Mn) of 5800 g/mol Using a process similar to that used for the preparation of co-polyamino acid B3 applied to a hydrochloride salt of molecule A18 (5.43 g, 6.86 mmol) and to co-polyamino acid B2-1 (6.00 g), with a saponification step at pH 13 for 3 hours in a mixture containing 30% by mass of ethanol, a sodium poly-L-glutamate modified by molecule A18 for which the esters are deprotected is obtained.

Dry extract: 22.0 mg/g
DP (estimated according to RMN $^1$H): 40
According to RMN $^1$H: i=0.15
The average calculated molar mass of Co-polyamino acid B20 is 10444 g/mol.
Organic HPLC-SEC (PEG calibrating): Mn=5800 g/mol.
Co-Polyamino Acid B21: Sodium poly-L-glutamate Modified by Molecule A19 for which the Esters are Deprotected and Having a Number Average Molar Mass (Mn) of 5000 g/mol Using a process similar to that used for the preparation of co-polyamino acid B18 applied to molecule A19 (32.64 g, 45.97 mmol) and to co-polyamino acid B2-1 (40.20 g), a sodium poly-L-glutamate modified by molecule A19 for which the ester is saponified is obtained.

Dry extract: 26.2 mg/g
DP (estimated according to RMN $^1$H): 40
According to RMN $^1$H: i=0.15
The average calculated molar mass of Co-polyamino acid B21 is 9716 g/mol.

Organic HPLC-SEC (PEG calibrating): Mn=5000 g/mol.

Co-Polyamino Acid B22: Sodium poly-L-glutamate Modified at One of its Extremities by Molecule A20 and Having a Number Average Molar Mass (Mn) of 1900 g/mol Using a process similar to that used for the preparation of co-polyamino acid B14 applied to molecule A20 (13.28 g, 12.51 mmol) in $CHCl_3$ (53 mL) and to γ-benzyl-L-glutamate N-carboxyanhydride (72.46 g, 275.2 mmol), in DMF (270 mL), with a saponification step at pH 12 for 1 hour 30 minutes, a sodium poly-L-glutamate modified at one of its extremities by molecule A20, is obtained.

Dry extract: 27.3 mg/g
DP (estimated according to RMN $^1$H): 20
According to RMN $^1$H: i=0.05
The average calculated molar mass of Co-polyamino acid B22 is 4087 g/mol.
Aqueous HPLC-SEC (PEG calibrating): Mn=1900 g/mol.

ii) Co-Polyamino Acids According to Formulas XXX and XXXb

| No. | CO-POLYAMINO ACIDS BEARING CARBOXYLATE CHARGES AND HYDROPHOBIC RADICALS |
|---|---|
| B7' | 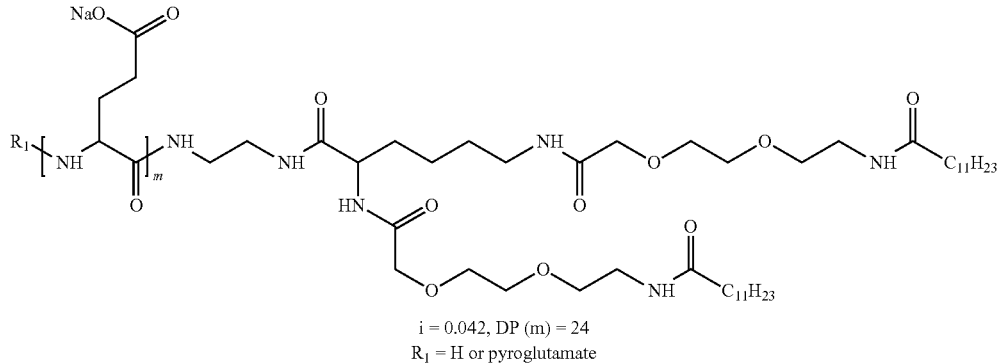 i = 0.042, DP (m) = 24<br>$R_1$ = H or pyroglutamate |
| B8 | 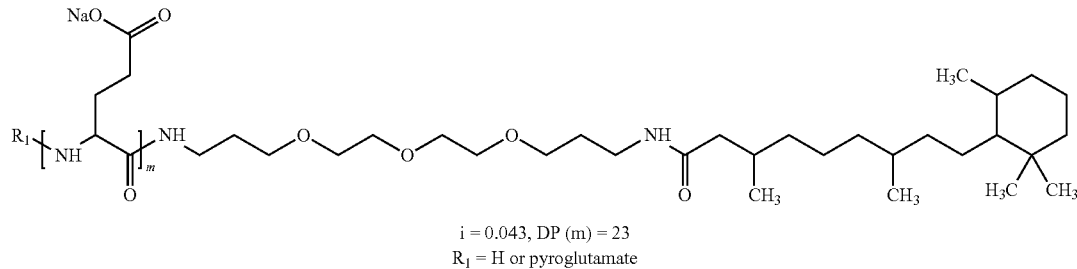 i = 0.043, DP (m) = 23<br>$R_1$ = H or pyroglutamate |
| B10 | 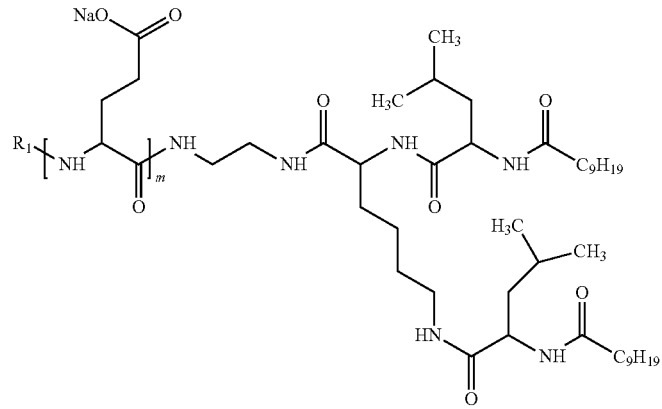 i = 0.032, DP (m) = 31<br>$R_1$ = H or pyroglutamate |

| No. | CO-POLYAMINO ACIDS BEARING CARBOXYLATE CHARGES AND HYDROPHOBIC RADICALS |
|---|---|
| B11 | 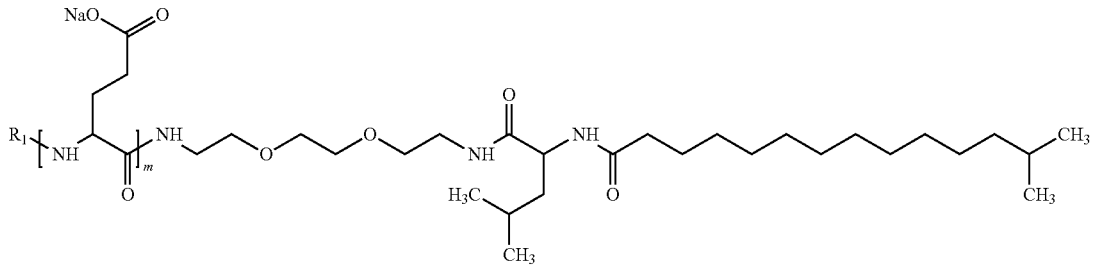
i = 0.034, DP (m) = 29
$R_1$ = H or pyroglutamate |
| B12 | 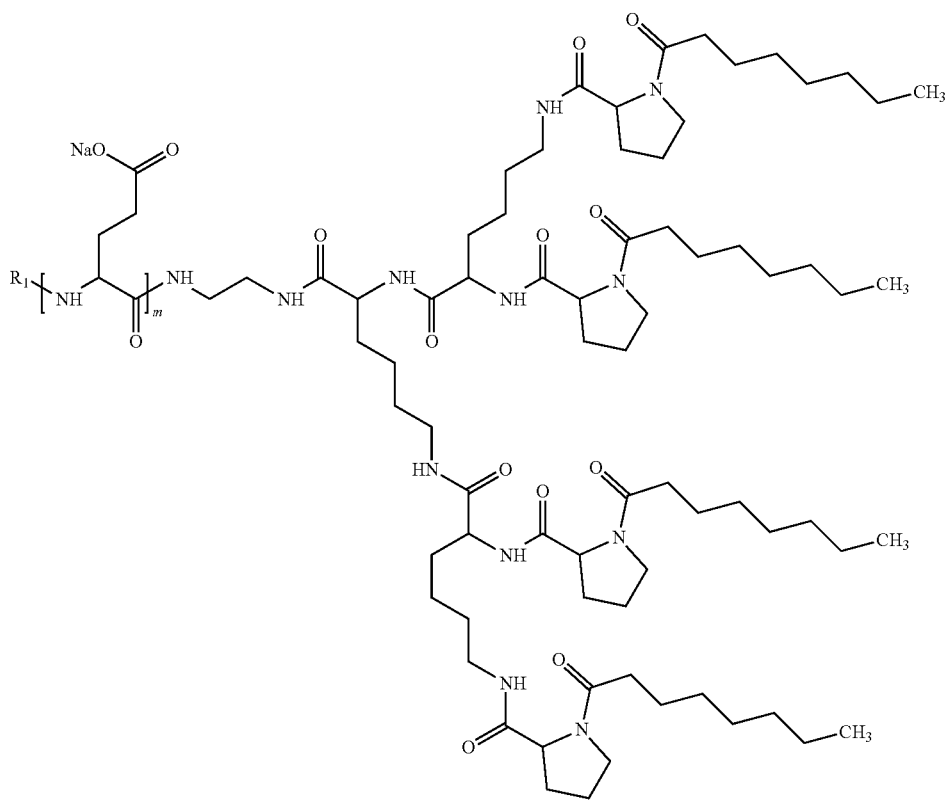
i = 0.042, DP (m) = 24
$R_1$ = H or pyroglutamate |

Co-Polyamino Acid B7': Sodium poly-L-glutamate Modified at One of its Extremities by Molecule A5a and Having a Number Average Molar Mass (Mn) of 2600 g/mol Co-Polyamino Acid B7'-1: poly-L-benzylglutamate Modified at One of its Extremities by Molecule A5a.

In a previously oven-dried flask, γ-benzyl-L-glutamate N-carboxyanhydride (10.1 g, 38.4 mmol) is solubilized in anhydrous DMF (19 mL). The mixture then stirred until completely dissolved, cooled to 0° C., then a solution of molecule A5a (1.47 g, 1.74 mmol) in chloroform (3.7 mL) is quickly introduced. The mixture is stirred from 0° C. and room temperature for 2 hours, then heated to 65° C. for 2 hours. The reaction medium is cooled to room temperature and poured drop-by-drop into diisopropylether (0.29 L) while being stirred. The white precipitate is recovered by filtration, washed two times with diisopropylether (5×50 mL), then dried under vacuum at 30° C. in order to obtain a white solid.

Co-Polyamino Acid B7'

Co-polyamino acid B7'-1 (8.33 g, 33.0 mmol) is diluted in trifuloroacetic (TFA, 132 mL), then the solution is cooled to 4° C. A 33% HBr solution in acetic acid (92.5 mL, 0.528 mol) is then added drop-by-drop. The mixture is stirred at room temperature for 2 hours, then poured drop-by-drop over a 1:1 mixture (v/v) of diisopropylether and water while stirring (0.8 L). After stirring for 2 hours, the heterogeneous mixture is allowed to rest overnight. The white precipitate is recovered by filtration, washed with IPE (2×66 mL) then with water (2×66 mL). The solid obtained is then solubilized in water (690 mL) while adjusting the pH to 7 by the addition of a 1 N aqueous soda solution. After solubilization, the theoretical concentration is adjusted to theoretical 20 g/L by the addition of water (310 mL), the solution is filtered through a 0.45 µm filter, then purified by ultrafiltration against a solution of NaCl 0.9%, then water until the conductimetry of the permeate is less than 50 µS/cm. The solution obtained is filtered through 0.2 µm and stored at 2-8° C.

Dry extract: 17.3 mg/g
DP (estimated according to RMN $^1$H): 24
According to RMN $^1$H: i=0.042
The average calculated molar mass of co-polyamino acid B7' is 4430 g/mol.
Organic HPLC-SEC (PEG calibrating): Mn=2600 g/mol.

Example B8: Co-Polyamino Acid B8—Sodium poly-L-glutamate Modified at One of its Extremities by Molecule A6a and Having a Number Average Molar Mass (Mn) of 2400 g/mol Co-Polyamino Acid B8-1: poly-L-benzylglutamate Modified at One of its Extremities by Molecule A6.

In a previously oven-dried flask, γ-benzyl-L-glutamate N-carboxyanhydride (19.0 g, 72.2 mmol) is solubilized in anhydrous DMF (19 mL). The mixture then stirred until completely dissolved, cooled to 0° C., then a solution of molecule A6a (1.68 g, 3.28 mmol) in chloroform (3.7 mL) is quickly introduced. The mixture is stirred from 0° C. to room temperature for 2 hours, then heated to 65° C. for 2 hours. The reaction medium is cooled to room temperature and poured drop-by-drop into diisopropylether (0.29 mL) while being stirred. The white precipitate is recovered by filtration, washed two times with diisopropylether (5×50 mL), then dried under vacuum at 30° C. in order to obtain a white solid.
Co-Polyamino Acid B8

Using a process similar to that used for the preparation of co-polyamino acid B7' applied to co-polyamino acid B8-1 (14.6 g, 61.5 mmol), a sodium poly-L-glutamate modified at one of its extremities by molecule Aha is obtained.

Dry extract: 21.3 mg/g
DP (estimated according to RMN $^1$H): 23
According to RMN $^1$H: i=0.043
The average calculated molar mass of Co-polyamino acid B8 is 3948 g/mol.
Organic HPLC-SEC (PEG calibrating): Mn=2400 g/mol.
Co-Polyamino Acid B10: Sodium poly-L-glutamate Modified at One of its Extremities by Molecule A8 and Having a Number Average Molar Mass (Mn) of 3100 g/mol
Co-Polyamino Acid B10-1: poly-L-benzylglutamate Modified at One of its Extremities by Molecule A8.

Into a suitable container are introduced, in succession, hydrochloride salt of molecule A8 (2.308 g, 3.04 mmol), chloroform (120 mL), molecular sieve 4 Å (1.5 g), as well as the ion exchange resin Amberlite IRN 150 (1.5 g). After stirring from 1 hour on rollers, the medium is filtered and the resin is rinsed with chloroform. The mixture is evaporated, then co-evaporated with toluene. The residue is solubilized in anhydrous DMF (40 mL) in order to be used directly in the polymerization reaction.

In a previously oven-dried flask, γ-benzyl-L-glutamate N-carboxyanhydride (20.0 g, 76.0 mmol) is solubilized in anhydrous DMF (19 mL). The mixture then stirred until completely dissolved, cooled to 0° C., then a solution of molecule A8, previously prepared, in chloroform (3.7 mL) is quickly introduced. The mixture is stirred from 0° C. to room temperature for 2 hours, then heated to 65° C. for 2 hours. The reaction medium is cooled to room temperature and poured drop-by-drop into diisopropylether (0.29 mL) while being stirred. The white precipitate is recovered by filtration, washed two times with diisopropylether (5×50 mL), then dried under vacuum at 30° C. in order to obtain a white solid.
Co-Polyamino Acid B10

Using a process similar to that used for the preparation of co-polyamino acid B7' applied to co-polyamino acid B10-1 (15.2 g, 60.8 mmol), a sodium poly-L-glutamate modified at one of its extremities by molecule A8 is obtained.

Dry extract: 34.1 mg/g
DP (estimated according to RMN $^1$H): 31
According to RMN $^1$H: i=0.032
The average calculated molar mass of Co-polyamino acid B10 is 5367 g/mol.
Organic HPLC-SEC (PEG calibrating): Mn=3100 g/mol.

Example B11: Co-Polyamino Acid B11—Sodium poly-L-glutamate Modified at One of its Extremities by Molecule A9 and Having a Number Average Molar Mass (Mn) of 3000 g/mol Co-Polyamino Acid B11-1: poly-L-benzylglutamate Modified at One of its Extremities by Molecule A9.

In an appropriate container are introduced successively, hydrochloride salt of molecule A9 (2.023 g, 3.87 mmol), chloroform (120 mL), molecular sieve 4 Å (1.5 g), as well as the ion exchange resin Amberlite IRN 150 (1.5 g). After stirring 1 hour on rollers, the medium is filtered and the resin is rinsed with chloroform. The mixture is evaporated, then co-evaporated with toluene. The residue is solubilized in anhydrous DMF (40 mL) in order to be used directly in the polymerization reaction.

Using a process similar to that used for the preparation of co-polyamino acid B8-1 applied to the solution of molecule A9 prepared previously and to γ-benzyl-L-glutamate N-carboxyanhydride (25.5 g, 96.8 mmol), co-polyamino acid B11-1 is obtained.
Co-Polyamino Acid B11

Using a process similar to that used for the preparation of co-polyamino acid B7' applied to co-polyamino acid B11-1 (18.4 g, 77.3 mmol), a sodium poly-L-glutamate modified at one of its extremities by molecule A9 is obtained.

Dry extract: 28.0 mg/g
DP (estimated according to RMN $^1$H): 29
According to RMN $^1$H: i=0.034
The average calculated molar mass of Co-polyamino acid B11 is 4828 g/mol.
Organic HPLC-SEC (PEG calibrating): Mn=3000 g/mol.
Co-Polyamino Acid B12: Sodium poly-L-glutamate Modified at One of its Extremities by Molecule A10 and Having a Number Average Molar Mass (Mn) of 2700 g/mol
Co-Polyamino Acid B12-1: poly-L-benzylglutamate Modified at One of its Extremities by Molecule A10.

Using a process similar to that used for the preparation of co-polyamino acid B10-1 applied to molecule A10 (3.0 g, 2.24 mmol) and to γ-benzyl-L-glutamate N-carboxyanhydride (12.99 g, 49.3 mmol), co-polyamino acid B12-1 is obtained.
Co-Polyamino Acid B12

Using a process similar to that used for the preparation of co-polyamino acid B7' applied to co-polyamino acid B12-1 (13.2 g, 48.0 mmol), a sodium poly-L-glutamate modified at one of its extremities by molecule A10 is obtained.

Dry extract: 13.2 mg/g
DP (estimated according to RMN $^1$H): 24
According to RMN $^1$H: i=0.042
The average calculated molar mass of Co-polyamino acid B12 is 4924 g/mol.
Organic HPLC-SEC (PEG calibrating): Mn=2700 g/mol.

PART C: COMPOSITIONS

Example C1: Preparation of a 0.6 mg/mL Pramlintide Solution Containing m-cresol (29 mM) and Glycerin (174 mM) at pH 6.6

A 5 mg/mL concentrated solution of pramlintide is prepared by dissolving pramlintide in powder form purchased from Ambiopharm. This solution is added to a concentrated solution of excipients (m-cresol, glycerin) in order to obtain the aimed final composition. The pH is adjusted to 6.6 by adding NaOH/HCl.

Example C1-1: Preparation of a 0.9 mg/mL Pramlintide Solution Containing m-cresol (29 mM) and Glycerin (174 mM) at pH 6.6

By means of a similar protocol to that described in example C1a 0.9 mg/mL pramlintide solution containing m-cresol (29 mM) and glycerin (174 mM) at pH 6.6 is obtained. The solution is clear.

Example C2: Preparation of a 0.6 mg/mL Pramlintide Solution Containing Co-Polyamino Acid B3, m-cresol (29 mM) and Glycerin (174 mM) at pH 6.6

A concentrated solution of co-polyamino acid B3 and excipients is prepared by adding concentrated solutions of excipients (m-cresol, glycerin) to a concentrated solution of co-polyamino acid B3.
A 5 mg/mL concentrated solution of pramlintide at pH 4 and of excipients is added to this concentrated solution of co-polyamino acid B3 in order to obtain the final compositions C2-1 to C2-5 (table 1). The pH is adjusted to 6.6 by adding NaOH/HCl.

TABLE 1

Compositions and visual appearance of solutions of pramlintide at pH 6.6 at different concentrations in co-polyamino acid B3.

| Solution | Ratio B3/pramlintide mol/mol | Concentration in co-polyamino acid B3 mg/mL | mM | Visual appearance of the solution |
|---|---|---|---|---|
| C1 | — | — | — | Clear |
| C2-1 | 1.0 | 1.4 | 0.15 | Clear |
| C2-2 | 1.5 | 2.0 | 0.23 | Clear |
| C2-3 | 2.0 | 2.7 | 0.30 | Clear |
| C2-4 | 3.0 | 4.1 | 0.46 | Clear |
| C2-5 | 5.0 | 6.8 | 0.76 | Clear |

Example C3: Preparation of a 0.6 mg/mL Pramlintide Solution Containing Different Co-Polyamino Acids According to the Invention, m-cresol (29 mM) and Glycerin (174 mM) at pH 6.6

Using a protocol similar to that described in example C2, 0.6 mg/mL pramlintide solutions 0.6 mg/mL pramlintide solutions containing different co-polyamino acids according to the invention, m-cresol (29 mM) and glycerin (174 mM) at pH 7.4 are obtained (tables 2 and 2a).

TABLE 2

Compositions and visual appearance of 0.6 mg/mL pramlintide solutions at pH 6.6 in the presence of different co-polyamino acids.

| Solution | Co-polyamino acid | Concentration in co-polyamino acid mg/mL | mM | Ratio co-polyamino acid/ pramlintide mol/mol | Visual appearance of the solution |
|---|---|---|---|---|---|
| C3-1 | B1 | 2.3 | 0.46 | 3 | Clear |
| C3-2 | B2 | 1.4 | 0.15 | 1 | Clear |
|  |  | 2.8 | 0.3 | 2 | Clear |
| C3-3 | B4 | 2.7 | 0.3 | 2 | Clear |
|  |  | 4 | 0.46 | 3 | Clear |
|  |  | 5.3 | 0.61 | 4 | Clear |
| C3-19 | B1 | 1.87 | 0.45 | 3 | Clear |
| C3-20 | B1 | 3.73 | 0.91 | 6 | Clear |
| C3-21 | B1 | 10 | 2.45 | 16 | Clear |
| C3-22 | B13 | 4.09 | 0.76 | 5 | Clear |
| C3-23 | B13 | 6.5 | 1.22 | 8 | Clear |
| C3-24 | B14 | 5.74 | 1.22 | 8 | Clear |
| C3-25 | B14 | 7.17 | 1.52 | 10 | Clear |
| C3-26 | B17 | 1.96 | 0.76 | 5 | Clear |
| C3-27 | B17 | 2.35 | 0.91 | 6 | Clear |
| C3-28 | B18 | 1.58 | 0.16 | 1.1 | Clear |
| C3-29 | B18 | 2.36 | 0.24 | 1.6 | Clear |
| C3-30 | B19 | 1.38 | 0.15 | 1 | Clear |
| C3-31 | B19 | 2.07 | 0.23 | 1.5 | Clear |
| C3-32 | B20 | 2.3 | 0.23 | 1.5 | Clear |
| C3-33 | B20 | 3 | 0.3 | 2 | Clear |
| C3-34 | B15 | 7.4 | 0.61 | 4 | Clear |
| C3-35 | B21 | 3.1 | 0.3 | 2 | Clear |
| C3-36 | B22 | 4.4 | 1.06 | 7 | Clear |

TABLE 2a

Compositions and visual appearance of 0.6 mg/mL pramlintide solutions at pH 6.6 in the presence of different co-polyamino acids.

| Solution | Co-polyamino acid | Concentration in co-polyamino acid mg/mL | mM | Ratio co-polyamino acid/ pramlintide mol/mol | Visual appearance of the solution |
|---|---|---|---|---|---|
| C3-5 | B8 | 6 | 1.51 | 10 | Clear |
|  |  | 9 | 2.27 | 15 | Clear |
| C3-7 | B10 | 8.2 | 1.52 | 10 | Clear |
| C3-18 | B11 | 7.3 | 1.5 | 10 | Clear |

Example C8: Preparation of 0.6 mg/mL Pramlintide Solutions Containing Different Co-Polyamino Acids According to the Invention, m-cresol (29 mM) and Glycerin (174 mM), NaCl and Optionally, Zinc Chloride at pH 6.6

A concentrated solution of co-polyamino acid according to the invention and excipients is prepared by adding concentrated solutions of excipients (m-cresol, glycerin, NaCl, zinc chloride) to a concentrated solution of co-polyamino acid according to the invention.
A 5 mg/mL concentrated solution of pramlintide at pH 4 and of excipients is added to this concentrated solution of co-polyamino acid according to the invention in order to obtain the final compositions C8-5 to C8-15 (tables 2b and 2c). The pH is adjusted to 6.6 by adding NaOH/HCl.

TABLE 2b

Compositions and visual appearance of 0.6 mg/mL pramlintide solutions at pH 6.6 in the presence of different co-polyamino acids according to the invention, of sodium chloride and, optionally, of zinc chloride.

| Solution | Co-polyamino acid | Concentration in co-polyamino acid mg/mL | mM | Ratio co-polyamino acid/pramlintide | [NaCl] (mM) | [ZnCl$_2$] (mM) | Visual appearance of the solution |
|---|---|---|---|---|---|---|---|
| C8-5 | B8 | 4.8 | 1.22 | 8 | 100 | — | Clear |
| C8-6 | B8 | 4.8 | 1.22 | 8 | 100 | 1 | Clear |
| C8-7 | B11 | 7.3 | 1.5 | 10 | 100 | — | Clear |
| C8-8 | B11 | 7.3 | 1.5 | 10 | 100 | 1 | Clear |
| C8-9 | B10 | 8.2 | 1.5 | 10 | 100 | — | Clear |
| C8-10 | B10 | 8.2 | 1.5 | 10 | 100 | 1 | Clear |

TABLE 2c

Compositions and visual appearance of 0.6 mg/mL pramlintide solutions at pH 6.6 in the presence of different co-polyamino acids according to the invention, of sodium chloride and, optionally, of zinc chloride.

| Solution | Co-polyamino acid | Concentration in co-polyamino acid mg/mL | mM | Ratio co-polyamino acid/pramlintide | [NaCl] (mM) | [ZnCl$_2$] | Visual appearance of the solution |
|---|---|---|---|---|---|---|---|
| C8-11 | B1 | 1.87 | 0.45 | 3 | 25 | — | Clear |
| C8-12 | B1 | 3.1 | 0.76 | 5 | 25 | — | Clear |
| C8-13 | B13 | 4.1 | 0.76 | 5 | 50 | 0.229 | Clear |
| C8-14 | B13 | 4.09 | 0.76 | 5 | 50 | — | Clear |
| C8-15 | B17 | 1.96 | 0.76 | 5 | 25 | — | Clear |
| C8-16 | B17 | 2.35 | 0.91 | 6 | 25 | — | Clear |

Example C4: Preparation of a 0.6 mg/mL pramlintide solution and of 100 IU/mL human insulin containing m-cresol (29 mM) and glycerin (174 mM) and zinc chloride (229 µM) at pH 6.6.

The 5 mg/mL concentrated solution of pramlintide described in C1 is added to a concentrated solution of excipients (m-cresol, glycerin, zinc chloride). A 500 IU/mL human insulin solution is prepared by dissolving human insulin in powder form purchased from Amphastar. This solution is added to a concentrated solution of pramlintide and of excipients in order to obtain the target final composition. The pH is adjusted to 6.6 by adding NaOH/HCl.

Example C5: Preparation of a 0.6 mg/mL Pramlintide Solution and 100 IU/mL Human Insulin Containing Co-Polyamino Acid B3, m-cresol (29 mM) and Glycerin (174 mM) and Zinc Chloride (229 µM) at pH 6.6

A concentrated solution of co-polyamino acid B3 and excipients is prepared by adding concentrated solutions of excipients (m-cresol, glycerin, zinc chloride) to a concentrated solution of co-polyamino acid B3.

A 5 mg/mL concentrated solution of pramlintide at pH 4, then a 500 IU/mL human insulin solution are added to the concentrated solution of co-polyamino acid B3 and excipients in order to obtain the final target composition (table 3). The pH is adjusted to 6.6 by adding NaOH/HCl.

Solutions C4 and C5-1 to C5-5 are prepared according to the protocol above.

TABLE 3

Compositions and visual appearance of 0.6 mg/mL pramlintide solutions and human insulin at pH 6.6 at different concentrations in co-polyamino acid B3.

| Solution | Ratio B3/pramlintide mol/mol | Concentration in co-polyamino acid B3 mg/mL | mM | Visual appearance of the solution |
|---|---|---|---|---|
| C4 | — | — | — | Turbid |
| C5-1 | 1.0 | 1.4 | 0.15 | Clear |
| C5-2 | 1.5 | 2.0 | 0.23 | Clear |
| C5-3 | 2.0 | 2.7 | 0.30 | Clear |
| C5-4 | 3.0 | 4.1 | 0.46 | Clear |
| C5-5 | 5.0 | 6.8 | 0.76 | Clear |

Example C6: Preparation of a 0.6 mg/mL Pramlintide Solution and 100 IU/mL Human Insulin Containing Different Co-Polyamino Acids According to the Invention, m-cresol (29 mM) and Glycerin (174 mM) and Zinc Chloride (229 µM) at pH 6.6

Using a process similar to example C5, a 0.6 mg/mL pramlintide solution and 100 IU/mL human insulin containing a co-polyamino acid according to the invention, m-cresol (29 mM) and glycerin (174 mM) and zinc chloride (229 µM) at pH 6.6 is obtained.

Solutions C6-1 and C6-11 (Tables 4 and 4a) are prepared according to the above protocol.

TABLE 4

Compositions and visual appearance of 0.6 mg/mL pramlintide solutions and 100 IU/mL human insulin at pH 6.6 in the presence of different co-polyamino acids.

| Solution | Co-polyamino acid | Concentration in co-polyamino acid mg/mL | mM | Ratio co-polyamino acid/pramlintide mol/mol | Visual appearance of the solution |
|---|---|---|---|---|---|
| C6-1 | B7 | 2.4 | 0.6 | 4 | Clear |
| C6-2 | B1 | 3.8 | 0.76 | 5 | Clear |
|  |  | 6.1 | 1.22 | 8 | Clear |
| C6-3 | B2 | 1.4 | 0.15 | 1 | Clear |
|  |  | 2.8 | 0.3 | 2 | Clear |
|  |  | 4.2 | 0.45 | 3 | Clear |
| C6-4 | B4 | 2.7 | 0.3 | 2 | Clear |
|  |  | 4 | 0.45 | 3 | Clear |
|  |  | 6.7 | 0.75 | 5 | Clear |
| C6-6 | B1 | 10 | 2.45 | 16 | Clear |
| C6-7 | B20 | 3 | 0.3 | 2 | Clear |
| C6-8 | B15 | 7.4 | 0.61 | 4 | Clear |
| C6-9 | B18 | 3.2 | 0.32 | 2.1 | Clear |
| C6-10 | B21 | 3.1 | 0.3 | 2 | Clear |
| C6-11 | B22 | 4.4 | 1.06 | 7 | Clear |

TABLE 4a

Composition and visual appearance of the solution of pramlintide at 0.6 mg/mL and 100 IU/mL human insulin at pH 6.6 in the presence of different co-polyamino acids.

| Solution | Co-polyamino acid | Concentration in co-polyamino acid | | Ratio co-polyamino acid/ pramlintide | Visual appearance of the solution |
|---|---|---|---|---|---|
| | | mg/mL | mM | mol/mol | |
| C6-4' | B8 | 4.8 | 1.2 | 8 | Clear |
| C6-5 | B7' | 3.4 | 0.77 | 5 | Clear |
| | | 6.7 | 1.51 | 10 | Clear |

Example C10: Preparation of a 0.6 mg/mL Pramlintide Solution and 100 IU/mL Human Insulin Containing Co-Polyamino Acid B8, m-cresol (29 mM) and Glycerin (174 mM), and Varied Contents of Sodium Chloride and Zinc Chloride A concentrated solution of co-polyamino acid B8 and excipients is prepared by adding concentrated solutions of excipients (m-cresol, glycerin, sodium chloride, zinc chloride) to a concentrated solution of co-polyamino acid B8.

A 5 mg/mL concentrated solution of pramlintide at pH 4, then a 500 IU/mL human insulin solution are added to this concentrated solution of co-polyamino acid B8 and excipients in order to obtain the final target composition. The pH is adjusted to 6.6 by adding NaOH/HCl.

Solutions C10-6 and C10-7 are prepared according to the protocol above.

TABLE 4b

Compositions and visual appearance of 0.6 mg/mL pramlintide solutions and 100 IU/mL human insulin at pH 6.6 in the presence of different co-polyamino acids, and different concentrations of sodium chloride and zinc chloride.

| Solution | Co-polyamino acid | Concentration in co-polyamino acid | | Ratio co-polyamino acid/ pramlintide | [NaCl] | [ZnCl$_2$] | Visual appearance of the solution |
|---|---|---|---|---|---|---|---|
| | | mg/mL | mM | | (mM) | (mM) | |
| C10-6 | B8 | 4.8 | 1.22 | 8 | 100 | —* | Clear |
| C10-7 | B8 | 4.8 | 1.22 | 8 | 100 | 1* | Clear |

*Composition comprising 0.23 mM of ZnCl$_2$ from the solution of human insulin.

Results of Visual Observations of the Mixture and of ThT Fibrillation Measurements.

Principle

The poor stability of a peptide may lead to the formation of amyloid fibrils defined as ordered, macromolecular structures. These may possibly result in the formation of gel in the sample.

The follow-up test of fluorescence of thioflavin T (ThT) is used to analyze the physical stability of solutions. Thioflavin is a small probe molecule with a characteristic fluorescence signature when it bonds to amyloid type fibrils (Naiki et al. (1989) Anal. BioChem. 177, 244-249; LeVine (1999) Methods. Enzymol. 309, 274-284).

This method makes it possible to monitor the formation of fibrils for low concentrations of ThT in undiluted solutions. This monitoring is carried out under accelerated, stable conditions while stirring and at 37° C.

EXPERIMENTAL CONDITIONS

The samples are prepared just before the beginning of measurement. The preparation of each composition is described in the related example. Thioflavin T was added to the composition from a parent solution concentrated in order to induce negligible dilution of the composition. The concentration of Thioflavin T in the composition is 2 µM.

A volume of 150 µL of the composition was introduced into one of the well of a 96-well tray. Each composition was analyzed using three tests (triplicate) in the same tray. The tray was sealed by a transparent film in order to prevent evaporation of the composition.

This tray was then placed in the enclosure of a tray reader (EnVision 2104 Multilabel, Perkin Elmer). The temperature was set at 37° C., and lateral stirring of 960 rpm with 1 mm of amplitude was started.

A reading of the intensity of fluorescence in each well was carried out with an excitation wave length of 442 nm, and an emission wave length of 482 nm, over time.

The fibrillation process is manifested by a strong increase in fluorescence after a period called the latency time.

For each well, this period was determined graphically as the intersection between the fluorescence signal baseline and the slope of the fluorescence curve as a function of time determined during the initial strong increase in fluorescence. The value of the recorded latency time corresponds to the average of measurements of latency time taken on three wells.

An example of a graphic determination is represented in FIG. 1.

This FIGURE graphically represents the determination of the latency time (LT) by fluorescent monitoring of Thioflavin T, on a curve with the value of the fluorescence on the ordinate axis (in u.a., arbitrary units) and the time in minutes on the abscissa.

Example CA1: Stability of Solutions at 0.6 mg/mL of Pramlintide at pH 6.6 in the Presence of Co-Polyamino acid B3 at Different Concentrations

TABLE 5

Measurement of latency time by ThT of solutions C1 and C2-1 and C2-5.

| Solution | Ratio B3/pramlintide | Concentration in co-polyamino acid B3 | | Latency time |
|---|---|---|---|---|
| | mol/mol | mg/mL | mM | (h) |
| C1 | — | — | — | 1 |
| C2-1 | 1.0 | 1.4 | 0.15 | >19 |
| C2-2 | 1.5 | 2.0 | 0.23 | >60 |
| C2-3 | 2.0 | 2.7 | 0.30 | >60 |
| C2-4 | 3.0 | 4.1 | 0.46 | >60 |
| C2-5 | 5.0 | 6.8 | 0.76 | >60 |

The solution of pramlintide at pH 6.6 (C1) without co-polyamino acid has a short latency time; the latency times of the solutions containing co-polyamino acid B3 are higher.

Example CA2: Stability of 0.6 mg/mL Pramlintide Solutions at pH 6.6 in the Presence of Different Co-Polyamino Acids

TABLE 6

Measurement of latency time by ThT of compositions and C3-1 and C3-33.

| Solution | Co-poly-amino acid | Concentration in co-poly-amino acid mg/mL | mM | Ratio co-poly-amino acid/ pramlintide mol/mol | Latency time (h) |
|---|---|---|---|---|---|
| C3-1 | B1 | 2.3 | 0.46 | 3 | >3 |
| C3-2 | B2 | 1.4 | 0.15 | 1 | >20 |
|  |  | 2.8 | 0.3 | 2 | >40 |
| C3-3 | B4 | 2.7 | 0.3 | 2 | >15 |
|  |  | 4 | 0.46 | 3 | >20 |
|  |  | 5.3 | 0.61 | 4 | >40 |
| C3-25 | B14 | 5.74 | 1.22 | 8 | >25 |
| C3-26 |  | 7.17 | 1.52 | 10 | >60 |
| C3-28 | B18 | 1.58 | 0.16 | 1.1 | >25 |
| C3-29 |  | 2.36 | 0.24 | 1.6 | >60 |
| C3-30 | B19 | 1.38 | 0.15 | 1 | >15 |
| C3-31 |  | 2.07 | 0.23 | 1.5 | >80 |
| C3-32 | B20 | 2.3 | 0.23 | 1.5 | >50 |
| C3-33 |  | 3 | 0.3 | 2 | >80 |

The solution of pramlintide at pH 6.6 (C1) without co-polyamino acid has a short latency time. The co-polyamino acids according to the invention make it possible to obtain latency times greater than 3 hours under the conditions tested.

Example CA2a: Stability of 0.6 mg/mL pramlintide solutions in the presence of different co-polyamino acids, m-cresol (29 mM) and glycerin (174 mM), and different contents of NaCl and zinc chloride at pH 6.6

TABLE 6a

Measurement of latency time by ThT of compositions C3-7, C3-5, C3-18 and C8-5 to C8-10.

| Solution | Co-poly-amino acid | Concentration in co-polyamino acid mg/mL | mM | Ratio co-polyamino acid/ pramlintide | [NaCl] (mM) | [ZnCl₂] (mM) | Latency time (h) |
|---|---|---|---|---|---|---|---|
| C3-5 | B8 | 9 | 2.27 | 15 | — | — | 4 < t < 6 |
| C3-5 | B8 | 6.0 | 1.51 | 10 | — | — | <2 |
| C8-5 | B8 | 4.8 | 1.22 | 8 | 100 | — | >20 |
| C8-6 | B8 | 4.8 | 1.22 | 8 | 100 | 1 | >20 |
| C3-18 | B11 | 7.3 | 1.5 | 10 | — | — | <1 |
| C8-7 | B11 | 7.3 | 1.5 | 10 | 100 | — | >8 |
| C8-8 | B11 | 7.3 | 1.5 | 10 | 100 | 1 | >10 |
| C3-7 | B10 | 8.2 | 1.52 | 10 | — | — | <5 |
| C8-9 | B10 | 8.2 | 1.5 | 10 | 100 | — | >20 |
| C8-10 | B10 | 8.2 | 1.5 | 10 | 100 | 1 | >20 |

The solution of pramlintide at pH 6.6 (C1) without co-polyamino acid has a short latency time; the latency times of the solutions containing co-polyamino acids according to the invention in the presence of sodium chloride or of sodium chloride and zinc chloride are higher.

Example CA2b: Stability of 0.6 mg/mL Pramlintide Solutions in the Presence of Different Co-Polyamino Acids, m-cresol (29 mM) and Glycerin (174 mM), and Different Contents of NaCl and Zinc Chloride at pH 6.6

TABLE 6b

Measurement of latency time by ThT of compositions C3-19, C3-27 and C8-11 to C8-16.

| Solution | Co-poly-amino acid | Concentration in co-polyamino acid mg/mL | mM | Ratio co-poly-amino acid/ pramlinid | [NaCl] (mM) | [ZnCl₂] (mM) | Latency time (h) |
|---|---|---|---|---|---|---|---|
| C3-19 | B1 | 1.87 | 0.45 | 3 | — | — | <6 |
| C3-20 | B1 | 3.73 | 0.91 | 6 | — | — | <24 |
| C8-11 | B1 | 1.87 | 0.45 | 3 | 25 | — | >12 |
| C8-12 | B1 | 3.1 | 0.76 | 5 | 25 | — | >60 |
| C3-22 | B13 | 4.09 | 0.76 | 5 | — | — | <15 |
| C8-13 | B13 | 4.1 | 0.76 | 5 | 50 | 0.229 | >70 |
| C3-26 | B17 | 1.96 | 0.76 | 5 | — | — | <30 |
| C3-27 | B17 | 2.35 | 0.91 | 6 | — | — | <60 |
| C8-15 | B17 | 1.96 | 0.76 | 5 | 25 | — | >35 |
| C8-16 | B17 | 2.35 | 0.91 | 6 | 25 | — | >75 |

The solution of pramlintide at pH 6.6 (C1) without co-polyamino acid has a short latency time; the latency times of the solutions containing co-polyamino acids according to the invention in the presence of sodium chloride or of sodium chloride and zinc chloride are higher.

Example CA3: Compositions and Visual Appearance of 0.6 mg/mL Pramlintide Solutions and 100 IU/mL Human Insulin at pH 6.6 in the Presence of Co-Polyamino Acid B3 at Different Concentrations

TABLE 7

Measurement of latency time by ThT of compositions and C5-1 and C5-5.

| Solution | Ratio B3/pramlintide mol/mol | Concentration in co-polyamino acid B3 mg/mL | mM | Latency time (h) |
|---|---|---|---|---|
| C4 | — | — | — | * |
| C5-2 | 1.5 | 2.0 | 0.23 | >2 |
| C5-3 | 2.0 | 2.7 | 0.30 | >4 |
| C5-4 | 3.0 | 4.1 | 0.46 | >4 |
| C5-5 | 5.0 | 6.8 | 0.76 | >9 |

* means that the solution is turbid.

A 0.6 mg/mL pramlintide solution and 100 IU/mL human insulin at pH 6.6 without co-polyamino acid (C4) is turbid. Clear 0.6 mg/mL pramlintide solutions and of human insulin 100 IU/mL at pH 6.6 in the presence of co-polyamino acid B3 have latency times greater than 0.5 hour at a B3/pramlintide molar ratio of 1 and may be greater than 4 hours for B3/pramlintide molar ratios greater than 2.

Example CA4: Stability of 0.6 mg/mL Pramlintide Solutions and 100 IU/mL Human Insulin at pH 6.6 in the Presence of Different Co-Polyamino Acids

TABLE 8

Measurement of latency time by ThT of compositions C6-1 to C6-4 and C6-5.

| Solution | Co-polyamino acid | Concentration in co-polyamino acid | | Ratio co-polyamino acid/ pramlintide | Latency time |
|---|---|---|---|---|---|
| | | mg/mL | mM | mol/mol | (h) |
| C6-1 | B7 | 2.4 | 0.6 | 4 | >10 |
| C6-2 | B1 | 3.8 | 0.76 | 5 | >4 |
| | | 6.1 | 1.22 | 8 | >6 |
| C6-3 | B2 | 2.8 | 0.3 | 2 | >3 |
| | | 4.2 | 0.45 | 3 | >5 |
| C6-4 | B4 | 2.7 | 0.3 | 2 | >3 |
| | | 6.7 | 0.75 | 5 | >4 |

TABLE 8a

Measurement of latency time by ThT of compositions and C6-5 and C6-4

| Solution | Co-polyamino acid | Concentration in co-polyamino acid | | Ratio co-polyamino acid/ pramlintide | Latency time |
|---|---|---|---|---|---|
| | | mg/mL | mM | mol/mol | (h) |
| C6-5 | B7' | 3.4 | 0.77 | 5 | >2 |
| | | 6.7 | 1.51 | 10 | >5 |
| C6-4' | B8 | 4.8 | 1.2 | 8 | 2 > t > 1 |

The solution of pramlintide and human insulin at pH 6.6 (C4) is turbid. The co-polyamino acids according to the invention make it possible to obtain latency times greater than 1 hour under the conditions tested.

Example CA7: Preparation of a 0.6 mg/mL Pramlintide Solution and 100 IU/mL Human Insulin Containing Co-Polyamino Acid B8, m-cresol (29 mM) and Glycerin (174 mM), and Varied Contents of Sodium Chloride and Zinc Chloride TABLE 14b Measurement of latency time by ThT of compositions C6-4 and C10-6 to C10-7

| Solution | Co-polyamino acid | Concentration in co-polyamino acid | | Ratio co-polyamino acid/ pramlintid | [NaCl] | [ZnCl$_2$] | Latency time |
|---|---|---|---|---|---|---|---|
| | | mg/mL | mM | | (mM) | (mM) | (h) |
| C6-4' | B8 | 4.8 | 1.2 | 8 | — | —* | <2 |
| C10-6 | B8 | 4.8 | 1.22 | 8 | 100 | 0.23 | >8 |
| C10-7 | B8 | 4.8 | 1.22 | 8 | 100 | 1.2* | >9 |

*Composition comprising 0.23 mM of ZnCl$_2$ from the solution of human insulin.

The solution of pramlintide and human insulin at at pH 6.6 (C4) is turbid. The addition of zinc chloride containing B8 makes it possible to significantly increase the latency time compared to that obtained with the solution C6-4' with no zinc salt.

CB: Stability Study of Compositions According to the Invention.

Visual Inspection Procedure:

Three mL vials or cartridges filled with 1 mL of formulation are visually inspected in order to detect the appearance of visible particles or of turbidity. This inspection is carried out according to the recommendations of European Pharmacopoeia (EP 2.9.20): the vials are subjected to lighting of at least 2000 Lux and are observed in front of a white background and of a black background. The number of weeks or months of stability corresponds to the duration beginning at which the solutions contain visible particles or are turbid.

These results are in agreement with the US pharmacopoeia (USP <790>).

Example CB1: Physical Stability in Vial and Cartridge at 30° C. of Solutions of Pramlintide at 0.9 mg/mL and at 0.6 mg/mL in the Presence of Co-Polyamino Acid, m-cresol (29 mM) and Glycerin (174 mM) at pH 6.6

Solutions C1, C1-1, C8-14 and C3-21 are filtered (0.22 μm). 1 mL of solution is introduced into 3 mL glass cartridges by auto-injecting stylus and into 3 mL glass vials. The cartridges and vials are placed in an oven at 30° C. in stasis and are then observed every 2 weeks.

TABLE 15

Results of physical stabilities in cartridge at 30° C. of pramlintide composition at 0.6 mg/mL in the presence of co-polyamino acid B1 and B13.

| Solution | Co-polyamino acid | Concentration in co-polyamino acid mg/mL | Concentration pramlintide (mg/mL) | Stability physical 30° C. in vial | Stability physical 30° C. in cartridge (week) |
|---|---|---|---|---|---|
| C1-1 | — | — | 0.9 | <7 | <2 |
| C1 | — | — | 0.6 | <7 | — |
| C3-21 | B1 | 10 | 0.6 | — | >12 |
| C8-14 | B13 | 4.09 | 0.6 | >9 | >9 |

The pramlintide solutions at 0.9 mg/mL and 0.6 mg/mL at pH 6.6 have a physical stability in vial less than 7 weeks at 30° C. The physical stability in cartridge of the pramlintide solution at 0.9 mg/mL, pH 6.6 is less than 2 weeks.

The pramlintide solution at 0.6 mg/mL at pH 6.6 in the presence of co-polyamino acid B1 has a physical stability at 30° C. greater than 12 weeks in cartridge.

The pramlintide solution at 0.6 mg/ml at pH 6.6 in the presence of co-polyamino acid B13 has a physical stability at 30° C. greater than 9 weeks in cartridge and in vial.

Example CB2: Physical Stability in Vial and Cartridge at 30° C. of 0.6 mg/mL Pramlintide Solutions and of Insulin 100 IU/mL at pH 6.6 in the Presence of Co-Polyamino Acid B1 B20, m-cresol (29 mM) and Glycerin (174 mM) and Zinc (229 μM) at pH 6.6

Solutions C6-6 and C6-7 are filtered (0.22 μm). 1 mL of solution is introduced into 3 mL glass cartridges by auto-injecting stylus and into 3 mL glass vials. The cartridges and vials are placed in an oven at 30° C. in stasis and are then observed every 2 weeks.

TABLE 16

Results of physical stabilities in vial and cartridge at 30° C. of pramlintide compositions at 0.6 mg/mL. Insulin 100 IU/mL in the presence of co-polyamino acid 6.6.

| Solution | Co-polyamino acid | Concentration in co-polyamino acid mg/mL | Stability physical 30° C. in vial (week) | Stability physical 30° C. in cartridge (week) |
|---|---|---|---|---|
| C4 | — | — | * | * |
| C6-6 | B1 | 10 | >12 | >12 |
| C6-7 | B20 | 3 | >9 | — |

* solution turbid since preparation.

The solution of pramlintide at 0.6 mg/mL and 100 IU/mL human insulin at pH 6.6 is turbid.

The pramlintide solution at 0.6 mg/ml and of 100 IU/mL human insulin at pH 6.6 in the presence of co-polyamino acid B1 has a physical stability at 30° C. greater than 12 weeks in vial and greater than 12 weeks in cartridge.

The pramlintide solution at 0.6 mg/mL and of 100 IU/mL human insulin at pH 6.6 in the presence of co-polyamino acid B20 has a physical stability at 30° C. greater than 9 weeks in cartridge.

Example CB3: Physical Stability in Cartridge at 37° C. of 0.6 mg/mL Pramlintide Solutions in the Presence of a Co-Polyamino Acid, m-cresol (29 mM) and Glycerin (174 mM) at pH 6.6

The solution C3-21 is filtered (0.22 μm). 1 mL of solution is introduced into 3 mL self-injection pen glass cartridges into 3 mL self-injection pen glass cartridges. The cartridges are placed in an oven at 37° C. under static conditions and are then observed every 2 weeks.

TABLE 17

Results of physical stabilities in cartridge at 37° C. of 0.6 mg/mL pramlintide composition in the presence of co-polyamino acid.

| Solution | Co-polyamino acid | Concentration in co-polyamino acid mg/mL | Concentration pramlintide (mg/mL) | Stability physical 37° C. in cartridge (week) |
|---|---|---|---|---|
| C3-21 | B1 | 10 | 0.6 | >9 |

The 0.6 mg/mL pramlintide solution at pH 6.6 in the presence of co-polyamino acid B1 has a physical stability at 37° C. greater than 9 weeks in cartridge.

Example CB4: Physical Stability in and Cartridge at 37° C. of 0.6 mg/mL Pramlintide Solutions and of 100 IU/mL Insulin in the Presence of Co-Polyamino Acid, m-cresol (29 mM) and Glycerin (174 mM) and zinc (229 μM) at pH 6.6

Solutions C6-6 and C6-7 are filtered (0.22 μm). 1 mL of solution is introduced into 3 mL self-injection pen glass cartridges. The cartridges are placed in an oven at 37° C. under static conditions and are then observed every 2 weeks.

TABLE 18

Results of physical stabilities in cartridge at 37° C. of 0.6 mg/mL pramlintide composition in the presence of co-polyamino acid.

| Solution | Co-polyamino acid | Concentration in co-polyamino acid mg/mL | Stability physical 37° C. in cartridge (week) |
|---|---|---|---|
| C1 | — | — | * |
| C6-6 | B1 | 10 | >9 |
| C6-7 | B20 | 3 | >3 |

* solution turbid since preparation.

The 0.6 mg/mL pramlintide solution and 100 IU/mL human insulin at pH 6.6 is turbid.

The 0.6 mg/mL pramlintide solution at pH 6.6 in the presence of co-polyamino acid has a physical stability at 37° C. greater than 3 weeks in cartridge.

The invention claimed is:

1. A composition in the form of an injectable aqueous solution, for which the pH is comprised from 6.0 to 8.0, the composition comprising at least:

a) amylin or pramlintide;

b) a co-polyamino acid bearing carboxylate charges and hydrophobic radicals Hy, the co-polyamino acid being constituted of glutamic or aspartic units and the hydrophobic radicals Hy chosen among the radicals according to formula X as defined below:

Formula X

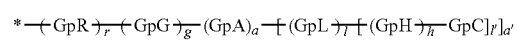

in which

GpR is chosen among the radicals according to formulas VII, VII' or VII":

Formula VII

Formula VII'

Formula VII"

identical or different GpG and GpH are chosen among the radicals according to formulas XI or XI';

Formula XI
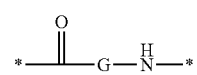

Formula XI'

GpA is chosen among the radicals according to formula VIII

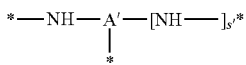

Formula VIII in which A' is chosen among the radicals according to formulas VIII', VIII" or VIII'''

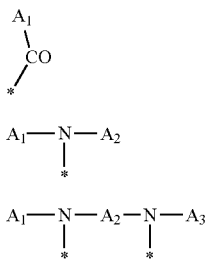

Formula VIII'

Formula VIII"

Formula VIII'''

GpL is chosen among the radicals according to formulas XII

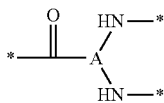

Formula XII

GpC is a radical according to formula IX:

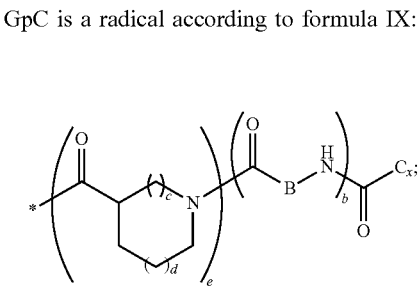

Formula IX

* indicate the attachment sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g, h or l is different from 0;
l is an integer equal to 0 or to 1 and l'=1 if l=0 and l'=2 if l=1;
r is an integer equal to 0, 1 or to 2, and
s' is an integer equal to 0 or to 1;
and if e is different from 0, then at least one of g, h or l is different from 0;
and if a=0, then l=0;
A, $A_1$, $A_2$ and $A_3$ identical or different, are linear or branched alkyl radicals comprising from 1 to 8 carbon atoms and/or substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical and/or comprising an aromatic ring, comprising from 1 to 9 carbon atoms;
$C_x$ is a monovalent, linear or branched, alkyl radical and/or comprising a cyclic part, in which x indicates the number of carbon atoms; and:
when the hydrophobic radical -Hy bears 1 -GpC, then $9 \leq x \leq 25$,
when the hydrophobic radical -Hy bears 2 -GpC, then $9 \leq x \leq 15$,
when the hydrophobic radical -Hy bears 3 -GpC, then $7 \leq x \leq 13$,
when the hydrophobic radical -Hy bears 4 -GpC, then $7 \leq x \leq 11$, and
when the hydrophobic radical -Hy bears at least 5 -GpC, then $6 \leq x \leq 11$,
G is a linear or branched divalent alkyl radical of 1 to 8 carbon atoms, the alkyl radical bearing one or more free carboxylic acid functions;
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms;
the hydrophobic radical(s) -Hy according to formula X being bound to the PLG:
via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG,
the ratio M between the number of hydrophobic radicals and the number of glutamic or aspartic units being between $0 < M \leq 0.5$;
when several hydrophobic radicals are borne by a co-polyamino acid, then they are identical or different;
the degree of polymerization DP in glutamic or aspartic units for the PLG chains is comprised from 5 to 250; and
free carboxylic acids being in the form of an alkaline cation salt chosen from the group consisting of $Na^+$ and $K^+$.

2. The composition according to claim 1, wherein the co-polyamino acid bearing carboxylate charges and hydrophobic radicals is chosen among the co-polyamino acids according to formula XXX below:

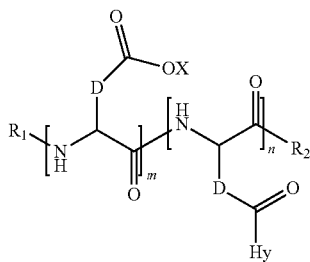

Formula XXX in which,
- D represents, independently, either a —CH$_2$— group (aspartic unit) or a —CH$_2$—CH$_2$— group (glutamic unit);
- Hy is a hydrophobic radical chosen among the hydrophobic radicals according to formulas X;
- R$_1$ is a hydrophobic radical chosen among the hydrophobic radicals according to formula X in which r=0 or r=1 and GpR is a radical according to formula VII' or VII", or a radical chosen from the group consisting of a H, a linear acyl group in C2 to C10, a branched acyl group in C3 to C10, a benzyl, a terminal "amino acid" unit and a pyroglutamate;
- R$_2$ is a hydrophobic radical chosen among the hydrophobic radicals according to formula X or an —NR'R" radical, R' and R", identical or different, being chosen from the group consisting of H, the linear, branched or cyclic alkyls in C2 to C10, benzyl and the R' and R" alkyls may together form one or more saturated, unsaturated and/or aromatic rings and/or may comprise heteroatoms, chosen from the group consisting of O, N and S;
- X represents a H or a cationic entity chosen from the group comprising the metallic cations; and
- n+m represents The degree of polymerization DP of the co-polyamino acid, that is the average number of monomeric units per co-polyamino acid chain and 5≤n+m≤250.

3. The composition according to claim 2, wherein the co-polyamino acid bearing carboxylate charges and hydrophobic radicals is chosen among the co-polyamino acids according to formula XXX, in which R$_1$=R'$_1$ and R$_2$=R'$_2$, according to formula XXXa below:

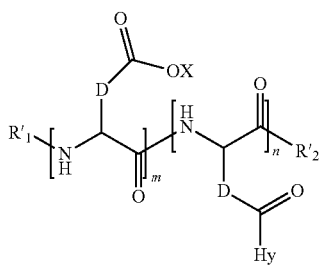

Formula XXXa in which,
- n+m represents The degree of polymerization DP of the co-polyamino acid, that is the average number of monomeric units per co-polyamino acid chain and 5≤n+m≤250;
- X represents a H or a cationic entity chosen from the group comprising the metallic cations;
- D represents, independently, either a —CH$_2$— group (aspartic unit) or a —CH$_2$—CH$_2$—group (glutamic unit);
- Hy is a hydrophobic radical chosen among the hydrophobic radicals according to formulas X;
- R'$_1$ is a radical chosen from the group consisting of a H, a linear acyl group in C2 to C10, a branched acyl group in C3 to C10, a benzyl, a terminal "amino acid" unit and a pyroglutamate; and
- R'$_2$ is a —NR'R" radical, R' and R", identical or different, being chosen in the group consisting of H, the linear, branched or cyclic alkyls in C2 to C10, benzyl and the R' and R" alkyls may together form one or more saturated, unsaturated and/or aromatic rings and/or may comprise heteroatoms, chosen from the group consisting of O, N and S.

4. The composition according to claim 2, wherein the co-polyamino acid bearing carboxylate charges and hydrophobic radicals is chosen among the co-polyamino acids according to formulas XXX, in which n=0, according to formula XXXb below:

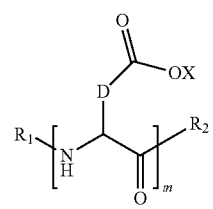

Formula XXXb in which
- m represents The degree of polymerization DP of the co-polyamino acid, that is the average number of monomeric units per co-polyamino acid chain and 5≤m≤250;
- X represents a H or a cationic entity chosen from the group comprising the metallic cations;
- D represents, independently, either a —CH$_2$— group (aspartic unit) or a —CH$_2$—CH$_2$—group (glutamic unit);
- R$_1$ is a hydrophobic radical chosen among the hydrophobic radicals according to formula X in which r=0 or r=1 and GpR is a radical according to formula VII' or VII", or a radical chosen from the group consisting of a H, a linear acyl group in C2 to C10, a branched acyl group in C3 to C10, a benzyl, a terminal "amino acid" unit and a pyroglutamate;
- R$_2$ is a hydrophobic radical chosen among the hydrophobic radicals according to formula X or an —NR'R" radical, R' and R", identical or different, being chosen from the group consisting of H, the linear, branched or cyclic alkyls in C2 to C10, benzyl and the R' and R" alkyls may together form one or more saturated, unsaturated and/or aromatic rings and/or may comprise heteroatoms, chosen from the group consisting of 0, N and S; and
- at least R$_1$ or R$_2$ is a hydrophobic radical according to formula X.

5. The composition according to claim 1, wherein the co-polyamino acid/amylin or pramlintide molar ratio is greater than or equal to 1.

6. The composition according to claim 1, wherein the amylin or pramlintide is amylin.

7. The composition according to claim 1, wherein the amylin or pramlintide is pramlintide.

8. The composition according to claim 1, further comprising a prandial insulin.

9. The composition according to claim 1, wherein the co-polyamino acid/insulin ratio is greater than or equal to 1.

10. The composition according to claim 1, wherein the composition has a stability measured by Thioflavin T (ThT) greater than that of a reference composition comprising amylin or pramlintide but not comprising a co-polyamino acid bearing carboxylate charges and Hy hydrophobic radicals.

11. A copolyaminoacid bearing carboxylate charges and hydrophobic radicals Hy, the co-polyamino acid being constituted of glutamic or aspartic units and the hydrophobic radicals Hy chosen among the radicals according to formula X as defined below:

$$*\!-\!(GpR)_r\!-\!(GpG)_g\!-\!(GpA)_a\!-\!\left[(GpL)_l\!-\!\left[(GpH)_h\!-\!GpC\right]_{l'}\right]_{a'} \quad \text{Formula X}$$

in which

GpR is chosen among the radicals according to formulas VII, VII′ or VII″:

$$*\!-\!\overset{H}{N}\!-\!R\!-\!\overset{H}{N}\!-\!* \quad \text{or} \quad \text{Formula VII}$$

$$*\!-\!\overset{O}{\underset{\|}{C}}\!-\!R\!-\!\overset{H}{N}\!-\!* \quad \text{or} \quad \text{Formula VII′}$$

$$*\!-\!\overset{O}{\underset{\|}{C}}\!-\!R\!-\!\overset{O}{\underset{\|}{C}}\!-\!* ; \quad \text{Formula VII″}$$

identical or different GpG and GpH are chosen among the radicals according to formulas XI or XI′;

$$*\!-\!\overset{O}{\underset{\|}{C}}\!-\!G\!-\!\overset{H}{N}\!-\!* \quad \text{Formula XI}$$

$$*\!-\!NH\!-\!G\!-\!NH\!-\!* \quad \text{Formula XI′}$$

GpA is chosen among the radicals according to formula VIII $$*\!-\!NH\!-\!A'\!-\![NH\!-\!]_{s'}* \quad \text{Formula VIII}$$

in which A′ is chosen among the radicals according to formulas VIII′, VIII″ or VIII‴

$$\begin{array}{c} A_1 \\ \diagdown \\ CO \\ \diagup \\ * \end{array} \quad \text{or} \quad \text{Formula VIII′}$$

$$A_1\!-\!\underset{\underset{*}{|}}{N}\!-\!A_2 \quad \text{or} \quad \text{Formula VIII″}$$

$$A_1\!-\!\underset{\underset{*}{|}}{N}\!-\!A_2\!-\!\underset{\underset{*}{|}}{N}\!-\!A_3 \quad \text{Formula VIII‴}$$

GpL is chosen among the radicals according to formulas XII $$*\!-\!\overset{O}{\underset{\|}{C}}\!-\!A\!\!\begin{array}{c} HN\!-\!* \\ \\ HN\!-\!* \end{array}, \quad \text{Formula XII}$$

GpC is a radical according to formula IX:

$$* \left( \text{...} \right)_{\!d}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\! \overset{}{_{e}} \left( \text{...} \right)_{b}\!-\!C_x; \quad \text{Formula IX}$$

* indicate the attachment sites of the different groups bound by amide functions;

a is an integer equal to 0 or to 1 and a′=1 if a=0 and a′=1, 2 or 3 if a=1;

a′ is an integer equal to 1, to 2 or to 3;

b is an integer equal to 0 or to 1;

c is an integer equal to 0 or to 1, and if c is equal to 0, then d is equal to 1 or to 2;

d is an integer equal to 0, to 1 or to 2;

e is an integer equal to 0 or to 1;

g is an integer equal to 0, to 1, to 2, to 3, to 4, to 5 or to 6;

h is an integer equal to 0, to 1, to 2, to 3, to 4, to 5 or to 6, and at least one of g, h or l is different from 0;

l is an integer equal to 0 or to 1 and l′=1 if l=0 and l′=2 if l=1;

r is an integer equal to 0, 1 or to 2, and s′ is an integer equal to 0 or to 1;

and if e is different from 0, then at least one of g, h or l is different from 0;

and if a=0, then l=0;

A, $A_1$, $A_2$ and $A_3$ identical or different, are linear or branched alkyl radicals comprising from 1 to 8 carbon atoms and/or substituted by a radical from a saturated, unsaturated or aromatic ring;

B is a radical ether or polyether, unsubstituted, comprising from 4 to 14 carbon atoms and 1 to 5 oxygen atoms, or a linear or branched alkyl radical and/or comprising an aromatic ring, comprising from 1 to 9 carbon atoms;

$C_x$ is a monovalent, linear or branched, alkyl radical and/or comprising a cyclic part, in which x indicates the number of carbon atoms; and:

when the hydrophobic radical -Hy bears 1 -GpC, then $9 \leq x \leq 25$, when the hydrophobic radical -Hy bears 2 -GpC, then $9 \leq x \leq 15$, when the hydrophobic radical -Hy bears 3 -GpC, then $7 \leq x \leq 13$, when the hydrophobic radical -Hy bears 4 -GpC, then $7 \leq x \leq 11$, and when the hydrophobic radical -Hy bears at least 5 -GpC, then $6 \leq x \leq 11$, G is a linear or branched divalent alkyl radical of 1 to 8 carbon atoms, the alkyl radical bearing one or more free carboxylic acid functions;

R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms;

the hydrophobic radicals -Hy according to formula X being bound to the PLG:

via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG, the ratio M between the number of hydrophobic radicals and the number of glutamic or aspartic units being between $0 < M \leq 0.5$;

when several hydrophobic radicals are borne by a co-polyamino acid, then they are identical or different;

the degree of polymerization DP in glutamic or aspartic units for the PLG chains is comprised from 5 to 250; and free carboxylic acids being in the form of an alkaline cation salt chosen from the group consisting of $Na^+$ and $K^+$.

12. A hydrophobic radical precursor Hy' of the hydrophobic radical -Hy according to formula X' as defined below:

Formula X'

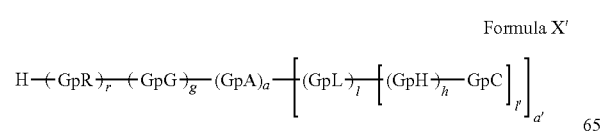

in which

GpR is chosen among the radicals according to formulas VII, VII' or VII":

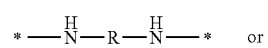
Formula VII

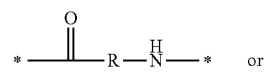
Formula VII'

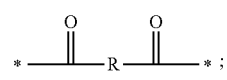
Formula VII";

identical or different GpG and GpH are chosen among the radicals according to formulas XI or XI';

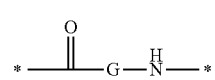
Formula XI

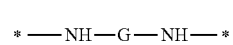
Formula XI'

GpA is chosen among the radicals according to formula VIII

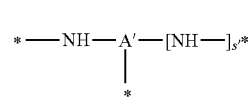
Formula VIII in which A' is chosen among the radicals according to formulas VIII', VIII" or VIII'''

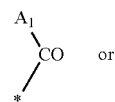
Formula VIII'

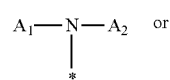
Formula VIII"

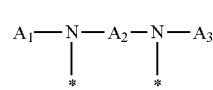
Formula VIII'''

GpL is chosen among the radicals according to formulas XII

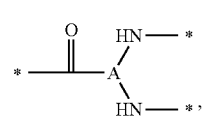
Formula XII

GpC is a radical according to formula IX:

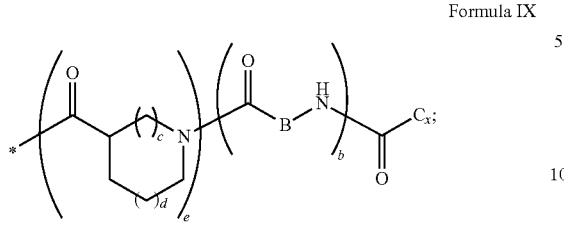

Formula IX

* indicate the attachment sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0, then d is equal to 1 or to 2;
d is an integer equal to 0, to 1 or to 2;
e is an integer equal to 0 or to 1;
g is an integer equal to 0, to 1, to 2, to 3, to 4, to 5 or to 6;
h is an integer equal to 0, to 1, to 2, to 3, to 4, to 5 or to 6, and at least one of g, h or l is different from 0;
l is an integer equal to 0 or to 1 and l'=1 if l=0 and l'=2 if l=1;
r is an integer equal to 0, 1 or to 2, and
s' is an integer equal to 0 or to 1;
and if e is different from 0, then at least one of g, h or l is different from 0;
and if a=0, then l=0;
A, $A_1$, $A_2$ and $A_3$ identical or different, are linear or branched alkyl radicals comprising from 1 to 8 carbon atoms and/or substituted by a radical from a saturated, unsaturated or aromatic ring;
B is a radical ether or polyether, unsubstituted, comprising from 4 to 14 carbon atoms and 1 to 5 oxygen atoms, or a linear or branched alkyl radical and/or comprising an aromatic ring, comprising from 1 to 9 carbon atoms;
$C_x$ is a monovalent, linear or branched, alkyl radical and/or comprising a cyclic part, in which x indicates the number of carbon atoms; and:
when the hydrophobic radical -Hy bears 1 -GpC, then $9 \leq x \leq 25$,
when the hydrophobic radical -Hy bears 2 -GpC, then $9 \leq x \leq 15$,
when the hydrophobic radical -Hy bears 3 -GpC, then $7 \leq x \leq 13$,
when the hydrophobic radical -Hy bears 4 -GpC, then $7 \leq x \leq 11$, and
when the hydrophobic radical -Hy bears at least 5 -GpC, then $6 \leq x \leq 11$,
G is a linear or branched divalent alkyl radical of 1 to 8 carbon atoms, the alkyl radical bearing one or more free carboxylic acid functions;
R is a radical chosen from the group consisting of a divalent, linear or branched alkyl radical comprising from 1 to 12 carbon atoms, a divalent, linear or branched alkyl radical comprising from 1 to 12 carbon atoms bearing one or more —$CONH_2$ functions or an unsubstituted ether or polyether radical comprising from 4 to 14 carbon atoms and 1 to 5 oxygen atoms;
the hydrophobic radical(s) -Hy according to formula X being bound to the PLG:
via a covalent bond between a carbonyl of the hydrophobic radical -Hy and a nitrogen atom borne by the PLG, thus forming an amide function resulting from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG, thus forming an amide function resulting from the reaction of an amine function of the precursor -Hy' of the hydrophobic radical -Hy and an acid function borne by the PLG,
the ratio M between the number of hydrophobic radicals and the number of glutamic or aspartic units being between $0 < M \leq 0.5$;
when several hydrophobic radicals are borne by a co-polyamino acid, then they are identical or different; and
free carboxylic acids being in the form of an alkaline cation salt chosen from the group consisting of $Na^+$ and $K^+$.

13. A method for improving the physical chemical stability of a composition according to claim 1 by adding ionic species chosen from the group of anions, cations and/or zwitterions.

* * * * *